United States Patent
Nakano et al.

(10) Patent No.: US 11,312,974 B2
(45) Date of Patent: Apr. 26, 2022

(54) GENE FOR INCREASING PLANT BIOMASS AND USE THEREFOR

(71) Applicants: JAPAN TOBACCO INC., Tokyo (JP); RIKEN, Wako (JP)

(72) Inventors: Takeshi Nakano, Saitama (JP); Tadao Asami, Saitama (JP); Tomoko Miyaji, Saitama (JP); Ayumi Yamagami, Saitama (JP); Noriko Ishikawa, Shizuoka (JP)

(73) Assignees: KANEKA CORPORATION, Osaka (JP); RIKEN, Wako (JP)

( * ) Notice: Subject to any disclaimer, the term of this patent is extended or adjusted under 35 U.S.C. 154(b) by 87 days.

(21) Appl. No.: 16/834,749

(22) Filed: Mar. 30, 2020

(65) Prior Publication Data
US 2020/0248198 A1    Aug. 6, 2020

Related U.S. Application Data

(63) Continuation of application No. 15/517,861, filed as application No. PCT/JP2015/078754 on Oct. 9, 2015, now Pat. No. 10,640,782.

(30) Foreign Application Priority Data

Oct. 10, 2014   (JP) .............................. JP2014-209154

(51) Int. Cl.
*C12N 15/82* (2006.01)
*C07K 14/415* (2006.01)
*C12Q 1/6895* (2018.01)
*A01H 1/00* (2006.01)
*C12N 5/04* (2006.01)
*C12Q 1/68* (2018.01)
*C12N 5/14* (2006.01)

(52) U.S. Cl.
CPC ........... *C12N 15/8261* (2013.01); *A01H 1/00* (2013.01); *C07K 14/415* (2013.01); *C12N 5/04* (2013.01); *C12N 5/14* (2013.01); *C12N 15/8209* (2013.01); *C12N 15/8222* (2013.01); *C12N 15/8274* (2013.01); *C12Q 1/68* (2013.01); *C12Q 1/6895* (2013.01); *C12Q 2600/13* (2013.01); *Y02A 40/146* (2018.01)

(58) Field of Classification Search
None
See application file for complete search history.

(56) References Cited

U.S. PATENT DOCUMENTS

| | | |
|---|---|---|
| 6,162,965 A | 12/2000 | Hansen |
| 2006/0123505 A1 | 6/2006 | Kikuchi et al. |
| 2011/0078818 A1 | 3/2011 | Kondo et al. |

FOREIGN PATENT DOCUMENTS

| | | |
|---|---|---|
| EP | 2361985 A1 | 8/2011 |
| WO | WO 2009/113684 A1 | 9/2009 |
| WO | WO 2011/074553 A1 | 6/2011 |

OTHER PUBLICATIONS

Alexandrov et al. (GenBank Accession No. EU957065.1; Published Dec. 10, 2008).*
Schnable et al. (GenBank Sequence Accession No. NP_001143141; Published Apr. 2017).*
Bork et al. (TIG, 12:425-427, 1996).
Doerks et al. (TIG, 14:248-250, 1998).
Guo et al. (PNAS, 101: 9205-9210, 2004).
International Search Report for PCT/JP2015/078754 (PCT/ISA/210) dated Dec. 22, 2015.
Keskin et al. (Protein Science, 13:1043-1055, 2004).
McConnell et al. (Nature, 411:709-713, 2001).
Miyaji (PhD dissertation, University of Tokyo; Published Dec. 7, 2015; English translation).
Miyaji et al. (Bioscience Biotechnology, and Biochemistry, 78:960-968; 2014; see in particular abstract).
Miyaji et al., "11. Brassinosteroid Joho Dentatsu Inshi BIL7 no Saibonai Kyokuzai Iko to Signal Dentatsu Inshi tono Sogo Sayo-Brassinosteroid signaling mutants bil7", Proceedings of Annual Meeting of Society for Chemical Regulation of Plants, 2012, vol. 47, No. Supplement, p. 28.
Miyaji et al., "33. Brassinosteroid Joho Dentatsu Inshi BIL7 no Kaku Iko Joken to Sogo Sayo Inshi no Kaiseki-Brassinosteroid signaling mutants bil7", Proceedings of Annual Meeting of Society for Chemical Regulation of Plants, Oct. 4, 2013, vol. 48, No. Supplement, p. 48.
Miyaji et al., "38. Saibomaku-Kaku Kan Iko ni yotte Shokubutsu Kakei Shincho o Sokushin suru Shinki Brassinosteroid Joho Dentatsu Inshi BIL7 no Kino Kaiseki-Brassinosteroid signaling mutants bil7", Proceedings of Annual Meeting of Society for Chemical Regulation of Plants, Oct. 1, 2014, vol. 49, No. Supplement, p. 56.

(Continued)

*Primary Examiner* — Vinod Kumar
(74) *Attorney, Agent, or Firm* — Birch, Stewart, Kolasch & Birch, LLP

(57) ABSTRACT

An object of the present invention is to identify a novel gene that effectively increases plant biomass and to provide said gene as well as techniques utilizing the same.

This invention provides a nucleic acid encoding a protein, wherein the protein comprises the amino acid sequence of SEQ ID NO:1 and an amino acid sequence having at least 25% identity or at least 75% similarity to the amino acid sequence of SEQ ID NO:7 or 11, and has an activity to increase plant biomass, as well as techniques utilizing the same.

13 Claims, 13 Drawing Sheets

Specification includes a Sequence Listing.

(56) References Cited

OTHER PUBLICATIONS

Miyaji, Hakase Ronbun(abstract), "Brassinosteroid Jo ho Dentatsu Idenshi BIL7 Oyobi BIL1 ni Kansuru Kagaku Seibutsuteki Kenkyu", University of Tokyo Gakujutsu Kikan Repository (UTokyo Repository), [online] Mar. 24, 2014, [retrieval date] Dec. 7, 2015. http://repository.dl.itc.u-tokyo.ac.jp/dspace/handle/2261/57959, 61 pages.
Ngo et al. (The Protein Folding Problem and Tertiary Structure Prediction, K. Merz., and S. Le Grand (eds.) pp. 492-495, 1994).
Nishimura et al. (Plant Cell Physiol., 41 (5):583-590, 2000).
Sasaki et al. (Gen Bank Sequence Accession No. AP004020; Published Feb. 15, 2008).
Smith et al. (Nature Biotechnology, 15:1222-1223, 1997).
Thornton et al. (Nature structural Biology, structural genomics supplement, Nov. 2000).
Wells (Biochemistry 29:8509-8517, 1990).
Written Opinion of the International Searching Authority for PCT/JP2015/078754 (PCT/ISA/237) dated Dec. 22, 2015.
Wu et al., "Brassinosteroids Regulate Grain Filling in Rice", The Plant Cell, vol. 20, Aug. 2008, pp. 2130-2145.
Xu et al. (Biotechnology and Bioengineering, 90:578-588, 2004).
Yang et al. (PNAS, 98:11438-11443, 2001).

\* cited by examiner

SEQUENCE LISTING

```
<160> NUMBER OF SEQ ID NOS: 49

<210> SEQ ID NO 1
<211> LENGTH: 167
<212> TYPE: PRT
<213> ORGANISM: Unknown
<220> FEATURE:
<223> OTHER INFORMATION: Consensus motif
<220> FEATURE:
<221> NAME/KEY: MISC_FEATURE
<222> LOCATION: (9)..(9)
<223> OTHER INFORMATION: Xaa is Phe or Tyr.
<220> FEATURE:
```

```
<221> NAME/KEY: MISC_FEATURE
<222> LOCATION: (10)..(10)
<223> OTHER INFORMATION: Xaa is Phe, Leu, Thr, or Ala.
<220> FEATURE:
<221> NAME/KEY: MISC_FEATURE
<222> LOCATION: (11)..(11)
<223> OTHER INFORMATION: Xaa is Gln, Pro, His, or Asn.
<220> FEATURE:
<221> NAME/KEY: MISC_FEATURE
<222> LOCATION: (13)..(13)
<223> OTHER INFORMATION: Xaa is Glu, Gly, Asp, Ala, or Met.
<220> FEATURE:
<221> NAME/KEY: MISC_FEATURE
<222> LOCATION: (14)..(14)
<223> OTHER INFORMATION: Xaa is Pro, Gly, Leu, or Ala.
<220> FEATURE:
<221> NAME/KEY: MISC_FEATURE
<222> LOCATION: (15)..(15)
<223> OTHER INFORMATION: Xaa is Pro, Ala, Thr, or Ser.
<220> FEATURE:
<221> NAME/KEY: MISC_FEATURE
<222> LOCATION: (17)..(17)
<223> OTHER INFORMATION: Xaa is Ala, Ile, Val, Ser, or Thr.
<220> FEATURE:
<221> NAME/KEY: MISC_FEATURE
<222> LOCATION: (18)..(18)
<223> OTHER INFORMATION: Xaa is Thr, Val, Ser, or Ala.
<220> FEATURE:
<221> NAME/KEY: MISC_FEATURE
<222> LOCATION: (19)..(19)
<223> OTHER INFORMATION: Xaa is Gln or His.
<220> FEATURE:
<221> NAME/KEY: MISC_FEATURE
<222> LOCATION: (20)..(20)
<223> OTHER INFORMATION: Xaa is Ser or Thr.
<220> FEATURE:
<221> NAME/KEY: MISC_FEATURE
<222> LOCATION: (22)..(51)
<223> OTHER INFORMATION: Xaa represents 15 to 30 arbitrary amino acid
      residues.
<220> FEATURE:
<221> NAME/KEY: MISC_FEATURE
<222> LOCATION: (56)..(56)
<223> OTHER INFORMATION: Xaa is His or Asn.
<220> FEATURE:
<221> NAME/KEY: MISC_FEATURE
<222> LOCATION: (58)..(58)
<223> OTHER INFORMATION: Xaa is Thr or Pro.
<220> FEATURE:
<221> NAME/KEY: MISC_FEATURE
<222> LOCATION: (59)..(59)
<223> OTHER INFORMATION: Xaa is Gln or Ala.
<220> FEATURE:
<221> NAME/KEY: MISC_FEATURE
<222> LOCATION: (60)..(60)
<223> OTHER INFORMATION: Xaa is Leu or Pro.
<220> FEATURE:
<221> NAME/KEY: MISC_FEATURE
<222> LOCATION: (62)..(62)
<223> OTHER INFORMATION: Xaa is Ser or Thr.
<220> FEATURE:
<221> NAME/KEY: MISC_FEATURE
<222> LOCATION: (68)..(68)
<223> OTHER INFORMATION: Xaa is Thr or Ala.
<220> FEATURE:
<221> NAME/KEY: MISC_FEATURE
<222> LOCATION: (69)..(69)
<223> OTHER INFORMATION: Xaa is Tyr or Phe.
<220> FEATURE:
<221> NAME/KEY: MISC_FEATURE
<222> LOCATION: (70)..(70)
<223> OTHER INFORMATION: Xaa is Thr, Ile, or Pro.
<220> FEATURE:
<221> NAME/KEY: MISC_FEATURE
<222> LOCATION: (72)..(72)
<223> OTHER INFORMATION: Xaa is Glu or Ala.
<220> FEATURE:
<221> NAME/KEY: MISC_FEATURE
<222> LOCATION: (75)..(75)
```

```
<223> OTHER INFORMATION: Xaa is Ser or Thr.
<220> FEATURE:
<221> NAME/KEY: MISC_FEATURE
<222> LOCATION: (78)..(78)
<223> OTHER INFORMATION: Xaa is Ile, Val, Tyr, or Phe.
<220> FEATURE:
<221> NAME/KEY: MISC_FEATURE
<222> LOCATION: (82)..(96)
<223> OTHER INFORMATION: Xaa represents 3 to 15 arbitrary amino acid
      residues.
<220> FEATURE:
<221> NAME/KEY: MISC_FEATURE
<222> LOCATION: (101)..(101)
<223> OTHER INFORMATION: Xaa is Glu or Asp.
<220> FEATURE:
<221> NAME/KEY: MISC_FEATURE
<222> LOCATION: (104)..(104)
<223> OTHER INFORMATION: Xaa is Phe or Tyr.
<220> FEATURE:
<221> NAME/KEY: MISC_FEATURE
<222> LOCATION: (106)..(155)
<223> OTHER INFORMATION: Xaa represents 20 to 50 arbitrary amino acid
      residues.
<220> FEATURE:
<221> NAME/KEY: MISC_FEATURE
<222> LOCATION: (157)..(157)
<223> OTHER INFORMATION: Xaa is Gly, Glu, or Asp.
<220> FEATURE:
<221> NAME/KEY: MISC_FEATURE
<222> LOCATION: (160)..(165)
<223> OTHER INFORMATION: Xaa represents 5 or 6 arbitrary amino acid
      residues.

<400> SEQUENCE: 1

Ala Pro Pro Ser Ser Pro Ala Ser Xaa Xaa Xaa Ser Xaa Xaa Xaa Ser
1               5                   10                  15

Xaa Xaa Xaa Xaa Pro Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Gly Pro Tyr Ala Xaa Glu Xaa Xaa Xaa Val Xaa Pro Pro
    50                  55                  60

Val Phe Ser Xaa Xaa Xaa Thr Xaa Pro Ser Xaa Ala Pro Xaa Thr Pro
65                  70                  75                  80

Pro Xaa Xaa Xaa Xaa Xaa Xaa Xaa Xaa Xaa Xaa Xaa Xaa Xaa Xaa Xaa
                85                  90                  95

Pro Ser Ser Pro Xaa Val Pro Xaa Ala Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Pro Xaa Ser Pro Xaa
145                 150                 155                 160

Xaa Xaa Xaa Xaa Xaa Ser Pro
                165

<210> SEQ ID NO 2
<211> LENGTH: 153
<212> TYPE: PRT
<213> ORGANISM: Unknown
<220> FEATURE:
<223> OTHER INFORMATION: Consensus motif
<220> FEATURE:
<221> NAME/KEY: MISC_FEATURE
<222> LOCATION: (10)..(10)
<223> OTHER INFORMATION: Xaa is Phe, Leu, or Thr.
```

-continued

```
<220> FEATURE:
<221> NAME/KEY: MISC_FEATURE
<222> LOCATION: (11)..(11)
<223> OTHER INFORMATION: Xaa is Gln, His, Pro, or Asn.
<220> FEATURE:
<221> NAME/KEY: MISC_FEATURE
<222> LOCATION: (13)..(13)
<223> OTHER INFORMATION: Xaa is Glu, Gly, Asp, or Ala.
<220> FEATURE:
<221> NAME/KEY: MISC_FEATURE
<222> LOCATION: (14)..(14)
<223> OTHER INFORMATION: Xaa is Pro, Gly, or Leu.
<220> FEATURE:
<221> NAME/KEY: MISC_FEATURE
<222> LOCATION: (15)..(15)
<223> OTHER INFORMATION: Xaa is Pro, Ala, Thr, or Ser.
<220> FEATURE:
<221> NAME/KEY: MISC_FEATURE
<222> LOCATION: (17)..(17)
<223> OTHER INFORMATION: Xaa is Ala, Val, Ile, or Thr.
<220> FEATURE:
<221> NAME/KEY: MISC_FEATURE
<222> LOCATION: (18)..(18)
<223> OTHER INFORMATION: Xaa is Thr, Ala, Val, or Ser.
<220> FEATURE:
<221> NAME/KEY: MISC_FEATURE
<222> LOCATION: (19)..(19)
<223> OTHER INFORMATION: Xaa is Gln or His.
<220> FEATURE:
<221> NAME/KEY: MISC_FEATURE
<222> LOCATION: (20)..(20)
<223> OTHER INFORMATION: Xaa is Ser or Thr.
<220> FEATURE:
<221> NAME/KEY: MISC_FEATURE
<222> LOCATION: (22)..(46)
<223> OTHER INFORMATION: Xaa represents 10 to 25 arbitrary amino acid
      residues.
<220> FEATURE:
<221> NAME/KEY: MISC_FEATURE
<222> LOCATION: (48)..(48)
<223> OTHER INFORMATION: Xaa is Ile, Val, Ala, or Met.
<220> FEATURE:
<221> NAME/KEY: MISC_FEATURE
<222> LOCATION: (49)..(49)
<223> OTHER INFORMATION: Xaa is Phe or Tyr.
<220> FEATURE:
<221> NAME/KEY: MISC_FEATURE
<222> LOCATION: (50)..(50)
<223> OTHER INFORMATION: Xaa is Ala or Thr.
<220> FEATURE:
<221> NAME/KEY: MISC_FEATURE
<222> LOCATION: (51)..(51)
<223> OTHER INFORMATION: Xaa is Ile, Val, or Thr.
<220> FEATURE:
<221> NAME/KEY: MISC_FEATURE
<222> LOCATION: (56)..(56)
<223> OTHER INFORMATION: Xaa is His or Asn.
<220> FEATURE:
<221> NAME/KEY: MISC_FEATURE
<222> LOCATION: (60)..(60)
<223> OTHER INFORMATION: Xaa is Leu or Pro.
<220> FEATURE:
<221> NAME/KEY: MISC_FEATURE
<222> LOCATION: (62)..(62)
<223> OTHER INFORMATION: Xaa is Ser or Thr.
<220> FEATURE:
<221> NAME/KEY: MISC_FEATURE
<222> LOCATION: (68)..(68)
<223> OTHER INFORMATION: Xaa is Thr or Ala.
<220> FEATURE:
<221> NAME/KEY: MISC_FEATURE
<222> LOCATION: (69)..(69)
<223> OTHER INFORMATION: Xaa is Tyr or Phe.
<220> FEATURE:
<221> NAME/KEY: MISC_FEATURE
<222> LOCATION: (70)..(70)
<223> OTHER INFORMATION: Xaa is Thr or Ile.
<220> FEATURE:
<221> NAME/KEY: MISC_FEATURE
```

```
<222> LOCATION: (75)..(75)
<223> OTHER INFORMATION: Xaa is Ser or Thr.
<220> FEATURE:
<221> NAME/KEY: MISC_FEATURE
<222> LOCATION: (78)..(78)
<223> OTHER INFORMATION: Xaa is Ile, Phe, or Tyr.
<220> FEATURE:
<221> NAME/KEY: MISC_FEATURE
<222> LOCATION: (82)..(96)
<223> OTHER INFORMATION: Xaa represents 3 to 15 arbitrary amino acid
      residues.
<220> FEATURE:
<221> NAME/KEY: MISC_FEATURE
<222> LOCATION: (101)..(101)
<223> OTHER INFORMATION: Xaa is Glu or Asp.
<220> FEATURE:
<221> NAME/KEY: MISC_FEATURE
<222> LOCATION: (104)..(104)
<223> OTHER INFORMATION: Xaa is Phe or Tyr.
<220> FEATURE:
<221> NAME/KEY: MISC_FEATURE
<222> LOCATION: (106)..(140)
<223> OTHER INFORMATION: Xaa represents 20 to 35 arbitrary amino acid
      residues.
<220> FEATURE:
<221> NAME/KEY: MISC_FEATURE
<222> LOCATION: (142)..(142)
<223> OTHER INFORMATION: Xaa is Gly, Glu, or Asp.
<220> FEATURE:
<221> NAME/KEY: MISC_FEATURE
<222> LOCATION: (145)..(149)
<223> OTHER INFORMATION: Xaa represents 3 to 5 arbitrary amino acid
      residues.
<220> FEATURE:
<221> NAME/KEY: MISC_FEATURE
<222> LOCATION: (151)..(151)
<223> OTHER INFORMATION: Xaa is Ile or Arg.

<400> SEQUENCE: 2

Ala Pro Pro Ser Ser Pro Ala Ser Phe Xaa Xaa Ser Xaa Xaa Xaa Ser
1               5                   10                  15

Xaa Xaa Xaa Xaa Pro Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Ser Xaa
            35                  40                  45

Xaa Xaa Xaa Gly Pro Tyr Ala Xaa Glu Thr Gln Xaa Val Xaa Pro Pro
    50                  55                  60

Val Phe Ser Xaa Xaa Xaa Thr Glu Pro Ser Xaa Ala Pro Xaa Thr Pro
65                  70                  75                  80

Pro Xaa Xaa Xaa Xaa Xaa Xaa Xaa Xaa Xaa Xaa Xaa Xaa Xaa Xaa Xaa
            85                  90                  95

Pro Ser Ser Pro Xaa Val Pro Xaa Ala Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Pro Xaa Ser Pro
            130                 135                 140

Xaa Xaa Xaa Xaa Xaa Leu Xaa Ser Pro
145                 150

<210> SEQ ID NO 3
<211> LENGTH: 480
<212> TYPE: PRT
<213> ORGANISM: Unknown
<220> FEATURE:
<223> OTHER INFORMATION: Consensus motif
<220> FEATURE:
<221> NAME/KEY: MISC_FEATURE
```

```
<222> LOCATION: (2)..(2)
<223> OTHER INFORMATION: Xaa is Arg or Gln.
<220> FEATURE:
<221> NAME/KEY: MISC_FEATURE
<222> LOCATION: (5)..(14)
<223> OTHER INFORMATION: Xaa represents 3 to 10 arbitrary amino acid
      residues.
<220> FEATURE:
<221> NAME/KEY: MISC_FEATURE
<222> LOCATION: (16)..(16)
<223> OTHER INFORMATION: Xaa is Val or Ser.
<220> FEATURE:
<221> NAME/KEY: MISC_FEATURE
<222> LOCATION: (17)..(17)
<223> OTHER INFORMATION: Xaa is Phe or Val.
<220> FEATURE:
<221> NAME/KEY: MISC_FEATURE
<222> LOCATION: (20)..(20)
<223> OTHER INFORMATION: Xaa is Ile or Val.
<220> FEATURE:
<221> NAME/KEY: MISC_FEATURE
<222> LOCATION: (25)..(25)
<223> OTHER INFORMATION: Xaa is Ser or Val.
<220> FEATURE:
<221> NAME/KEY: MISC_FEATURE
<222> LOCATION: (28)..(28)
<223> OTHER INFORMATION: Xaa is Ala or Val.
<220> FEATURE:
<221> NAME/KEY: MISC_FEATURE
<222> LOCATION: (29)..(29)
<223> OTHER INFORMATION: Xaa is Ser or Thr.
<220> FEATURE:
<221> NAME/KEY: MISC_FEATURE
<222> LOCATION: (30)..(30)
<223> OTHER INFORMATION: Xaa is Ser or Ala.
<220> FEATURE:
<221> NAME/KEY: MISC_FEATURE
<222> LOCATION: (31)..(31)
<223> OTHER INFORMATION: Xaa is Asp or Glu.
<220> FEATURE:
<221> NAME/KEY: MISC_FEATURE
<222> LOCATION: (32)..(32)
<223> OTHER INFORMATION: Xaa is Asp or Ser.
<220> FEATURE:
<221> NAME/KEY: MISC_FEATURE
<222> LOCATION: (34)..(43)
<223> OTHER INFORMATION: Xaa represents 5 to 10 arbitrary amino acid
      residues.
<220> FEATURE:
<221> NAME/KEY: MISC_FEATURE
<222> LOCATION: (47)..(47)
<223> OTHER INFORMATION: Xaa is Trp or Ala.
<220> FEATURE:
<221> NAME/KEY: MISC_FEATURE
<222> LOCATION: (48)..(48)
<223> OTHER INFORMATION: Xaa is Asn or Asp.
<220> FEATURE:
<221> NAME/KEY: MISC_FEATURE
<222> LOCATION: (49)..(49)
<223> OTHER INFORMATION: Xaa is Arg or Trp.
<220> FEATURE:
<221> NAME/KEY: MISC_FEATURE
<222> LOCATION: (50)..(50)
<223> OTHER INFORMATION: Xaa is Trp or Leu.
<220> FEATURE:
<221> NAME/KEY: MISC_FEATURE
<222> LOCATION: (52)..(52)
<223> OTHER INFORMATION: Xaa is Leu or Val.
<220> FEATURE:
<221> NAME/KEY: MISC_FEATURE
<222> LOCATION: (53)..(53)
<223> OTHER INFORMATION: Xaa is Leu or Tyr.
<220> FEATURE:
<221> NAME/KEY: MISC_FEATURE
<222> LOCATION: (54)..(54)
<223> OTHER INFORMATION: Xaa is Lys or Phe.
<220> FEATURE:
<221> NAME/KEY: MISC_FEATURE
<222> LOCATION: (59)..(59)
```

```
<223> OTHER INFORMATION: Xaa is Ser or Gln.
<220> FEATURE:
<221> NAME/KEY: MISC_FEATURE
<222> LOCATION: (60)..(60)
<223> OTHER INFORMATION: Xaa is Arg or Lys.
<220> FEATURE:
<221> NAME/KEY: MISC_FEATURE
<222> LOCATION: (61)..(61)
<223> OTHER INFORMATION: Xaa is Gln or Asn.
<220> FEATURE:
<221> NAME/KEY: MISC_FEATURE
<222> LOCATION: (62)..(62)
<223> OTHER INFORMATION: Xaa is Arg or Gly.
<220> FEATURE:
<221> NAME/KEY: MISC_FEATURE
<222> LOCATION: (63)..(63)
<223> OTHER INFORMATION: Xaa is Lys or Arg.
<220> FEATURE:
<221> NAME/KEY: MISC_FEATURE
<222> LOCATION: (66)..(66)
<223> OTHER INFORMATION: Xaa is Gly or Ser.
<220> FEATURE:
<221> NAME/KEY: MISC_FEATURE
<222> LOCATION: (67)..(67)
<223> OTHER INFORMATION: Xaa is Asn or His.
<220> FEATURE:
<221> NAME/KEY: MISC_FEATURE
<222> LOCATION: (68)..(68)
<223> OTHER INFORMATION: Xaa is Ser or Ala.
<220> FEATURE:
<221> NAME/KEY: MISC_FEATURE
<222> LOCATION: (75)..(99)
<223> OTHER INFORMATION: Xaa represents 20 to 25 arbitrary amino acid
      residues.
<220> FEATURE:
<221> NAME/KEY: MISC_FEATURE
<222> LOCATION: (102)..(102)
<223> OTHER INFORMATION: Xaa is Ile or Val.
<220> FEATURE:
<221> NAME/KEY: MISC_FEATURE
<222> LOCATION: (112)..(112)
<223> OTHER INFORMATION: Xaa is Phe or Leu.
<220> FEATURE:
<221> NAME/KEY: MISC_FEATURE
<222> LOCATION: (115)..(115)
<223> OTHER INFORMATION: Xaa is Glu or Gly.
<220> FEATURE:
<221> NAME/KEY: MISC_FEATURE
<222> LOCATION: (116)..(116)
<223> OTHER INFORMATION: Xaa is Pro or Gly.
<220> FEATURE:
<221> NAME/KEY: MISC_FEATURE
<222> LOCATION: (117)..(117)
<223> OTHER INFORMATION: Xaa is Pro or Ala.
<220> FEATURE:
<221> NAME/KEY: MISC_FEATURE
<222> LOCATION: (119)..(119)
<223> OTHER INFORMATION: Xaa is Ala or Ile.
<220> FEATURE:
<221> NAME/KEY: MISC_FEATURE
<222> LOCATION: (120)..(120)
<223> OTHER INFORMATION: Xaa is Thr or Val.
<220> FEATURE:
<221> NAME/KEY: MISC_FEATURE
<222> LOCATION: (126)..(126)
<223> OTHER INFORMATION: Xaa is Ile or Ala.
<220> FEATURE:
<221> NAME/KEY: MISC_FEATURE
<222> LOCATION: (127)..(127)
<223> OTHER INFORMATION: Xaa is Leu or Pro.
<220> FEATURE:
<221> NAME/KEY: MISC_FEATURE
<222> LOCATION: (133)..(133)
<223> OTHER INFORMATION: Xaa is Pro or Ser.
<220> FEATURE:
<221> NAME/KEY: MISC_FEATURE
<222> LOCATION: (134)..(134)
<223> OTHER INFORMATION: Xaa is Cys or Pro.
<220> FEATURE:
```

```
<221> NAME/KEY: MISC_FEATURE
<222> LOCATION: (136)..(145)
<223> OTHER INFORMATION: Xaa represents 1 to 10 arbitrary amino acid
      residues.
<220> FEATURE:
<221> NAME/KEY: MISC_FEATURE
<222> LOCATION: (168)..(168)
<223> OTHER INFORMATION: Xaa is Thr or Ala.
<220> FEATURE:
<221> NAME/KEY: MISC_FEATURE
<222> LOCATION: (169)..(169)
<223> OTHER INFORMATION: Xaa is Tyr or Phe.
<220> FEATURE:
<221> NAME/KEY: MISC_FEATURE
<222> LOCATION: (175)..(175)
<223> OTHER INFORMATION: Xaa is Ser or Thr.
<220> FEATURE:
<221> NAME/KEY: MISC_FEATURE
<222> LOCATION: (178)..(178)
<223> OTHER INFORMATION: Xaa is Ile or Phe.
<220> FEATURE:
<221> NAME/KEY: MISC_FEATURE
<222> LOCATION: (182)..(186)
<223> OTHER INFORMATION: Xaa represents 1 to 5 arbitrary amino acid
      residues.
<220> FEATURE:
<221> NAME/KEY: MISC_FEATURE
<222> LOCATION: (188)..(188)
<223> OTHER INFORMATION: Xaa is Ile or Val.
<220> FEATURE:
<221> NAME/KEY: MISC_FEATURE
<222> LOCATION: (189)..(189)
<223> OTHER INFORMATION: Xaa is Tyr or His.
<220> FEATURE:
<221> NAME/KEY: MISC_FEATURE
<222> LOCATION: (193)..(197)
<223> OTHER INFORMATION: Xaa represents 0 to 5 arbitrary amino acid
      residues.
<220> FEATURE:
<221> NAME/KEY: MISC_FEATURE
<222> LOCATION: (205)..(205)
<223> OTHER INFORMATION: Xaa is Phe or Tyr.
<220> FEATURE:
<221> NAME/KEY: MISC_FEATURE
<222> LOCATION: (207)..(207)
<223> OTHER INFORMATION: Xaa is Gln or Lys.
<220> FEATURE:
<221> NAME/KEY: MISC_FEATURE
<222> LOCATION: (209)..(209)
<223> OTHER INFORMATION: Xaa is Phe or Leu.
<220> FEATURE:
<221> NAME/KEY: MISC_FEATURE
<222> LOCATION: (210)..(210)
<223> OTHER INFORMATION: Xaa is Asn or Thr.
<220> FEATURE:
<221> NAME/KEY: MISC_FEATURE
<222> LOCATION: (212)..(231)
<223> OTHER INFORMATION: Xaa represents 10 to 20 arbitrary amino acid
      residues.
<220> FEATURE:
<221> NAME/KEY: MISC_FEATURE
<222> LOCATION: (233)..(233)
<223> OTHER INFORMATION: Xaa is Phe or Leu.
<220> FEATURE:
<221> NAME/KEY: MISC_FEATURE
<222> LOCATION: (235)..(235)
<223> OTHER INFORMATION: Xaa is Phe or Ser.
<220> FEATURE:
<221> NAME/KEY: MISC_FEATURE
<222> LOCATION: (238)..(238)
<223> OTHER INFORMATION: Xaa is Leu or Ile.
<220> FEATURE:
<221> NAME/KEY: MISC_FEATURE
<222> LOCATION: (239)..(239)
<223> OTHER INFORMATION: Xaa is Pro or Tyr.
<220> FEATURE:
<221> NAME/KEY: MISC_FEATURE
<222> LOCATION: (241)..(241)
<223> OTHER INFORMATION: Xaa is Gly or Glu.
```

```
-continued

<220> FEATURE:
<221> NAME/KEY: MISC_FEATURE
<222> LOCATION: (244)..(244)
<223> OTHER INFORMATION: Xaa is Leu or Ile.
<220> FEATURE:
<221> NAME/KEY: MISC_FEATURE
<222> LOCATION: (246)..(246)
<223> OTHER INFORMATION: Xaa is Gln or Arg.
<220> FEATURE:
<221> NAME/KEY: MISC_FEATURE
<222> LOCATION: (252)..(256)
<223> OTHER INFORMATION: Xaa represents 1 to 5 arbitrary amino acid
      residues.
<220> FEATURE:
<221> NAME/KEY: MISC_FEATURE
<222> LOCATION: (259)..(259)
<223> OTHER INFORMATION: Xaa is Pro or Thr.
<220> FEATURE:
<221> NAME/KEY: MISC_FEATURE
<222> LOCATION: (260)..(260)
<223> OTHER INFORMATION: Xaa is Thr or Cys.
<220> FEATURE:
<221> NAME/KEY: MISC_FEATURE
<222> LOCATION: (266)..(275)
<223> OTHER INFORMATION: Xaa represents 1 to 10 arbitrary amino acid
      residues.
<220> FEATURE:
<221> NAME/KEY: MISC_FEATURE
<222> LOCATION: (277)..(277)
<223> OTHER INFORMATION: Xaa is Leu or Thr.
<220> FEATURE:
<221> NAME/KEY: MISC_FEATURE
<222> LOCATION: (280)..(280)
<223> OTHER INFORMATION: Xaa is His or Ser.
<220> FEATURE:
<221> NAME/KEY: MISC_FEATURE
<222> LOCATION: (282)..(282)
<223> OTHER INFORMATION: Xaa is Gln or Pro.
<220> FEATURE:
<221> NAME/KEY: MISC_FEATURE
<222> LOCATION: (284)..(284)
<223> OTHER INFORMATION: Xaa is Ser or Arg.
<220> FEATURE:
<221> NAME/KEY: MISC_FEATURE
<222> LOCATION: (285)..(285)
<223> OTHER INFORMATION: Xaa is Asp or Glu.
<220> FEATURE:
<221> NAME/KEY: MISC_FEATURE
<222> LOCATION: (289)..(289)
<223> OTHER INFORMATION: Xaa is Leu or Ile.
<220> FEATURE:
<221> NAME/KEY: MISC_FEATURE
<222> LOCATION: (291)..(310)
<223> OTHER INFORMATION: Xaa represents 3 to 20 arbitrary amino acid
      residues.
<220> FEATURE:
<221> NAME/KEY: MISC_FEATURE
<222> LOCATION: (312)..(341)
<223> OTHER INFORMATION: Xaa represents 10 to 30 arbitrary amino acid
      residues.
<220> FEATURE:
<221> NAME/KEY: MISC_FEATURE
<222> LOCATION: (343)..(347)
<223> OTHER INFORMATION: Xaa represents 1 to 5 arbitrary amino acid
      residues.
<220> FEATURE:
<221> NAME/KEY: MISC_FEATURE
<222> LOCATION: (351)..(351)
<223> OTHER INFORMATION: Xaa is Asp or Glu.
<220> FEATURE:
<221> NAME/KEY: MISC_FEATURE
<222> LOCATION: (353)..(353)
<223> OTHER INFORMATION: Xaa is Asp or Thr.
<220> FEATURE:
<221> NAME/KEY: MISC_FEATURE
<222> LOCATION: (354)..(354)
<223> OTHER INFORMATION: Xaa is Ala or Val.
<220> FEATURE:
<221> NAME/KEY: MISC_FEATURE
```

```
<222> LOCATION: (355)..(355)
<223> OTHER INFORMATION: Xaa is Asp or Glu.
<220> FEATURE:
<221> NAME/KEY: MISC_FEATURE
<222> LOCATION: (356)..(356)
<223> OTHER INFORMATION: Xaa is His or Asp.
<220> FEATURE:
<221> NAME/KEY: MISC_FEATURE
<222> LOCATION: (358)..(358)
<223> OTHER INFORMATION: Xaa is Ile or Ala.
<220> FEATURE:
<221> NAME/KEY: MISC_FEATURE
<222> LOCATION: (361)..(361)
<223> OTHER INFORMATION: Xaa is Val or Leu.
<220> FEATURE:
<221> NAME/KEY: MISC_FEATURE
<222> LOCATION: (362)..(362)
<223> OTHER INFORMATION: Xaa is Asp or Glu.
<220> FEATURE:
<221> NAME/KEY: MISC_FEATURE
<222> LOCATION: (363)..(363)
<223> OTHER INFORMATION: Xaa is Gln or Lys.
<220> FEATURE:
<221> NAME/KEY: MISC_FEATURE
<222> LOCATION: (365)..(389)
<223> OTHER INFORMATION: Xaa represents 3 to 25 arbitrary amino acid
      residues.
<220> FEATURE:
<221> NAME/KEY: MISC_FEATURE
<222> LOCATION: (391)..(391)
<223> OTHER INFORMATION: Xaa is Glu or Arg.
<220> FEATURE:
<221> NAME/KEY: MISC_FEATURE
<222> LOCATION: (392)..(392)
<223> OTHER INFORMATION: Xaa is Ala or Glu.
<220> FEATURE:
<221> NAME/KEY: MISC_FEATURE
<222> LOCATION: (394)..(394)
<223> OTHER INFORMATION: Xaa is Ser or Asn.
<220> FEATURE:
<221> NAME/KEY: MISC_FEATURE
<222> LOCATION: (396)..(420)
<223> OTHER INFORMATION: Xaa represents 5 to 25 arbitrary amino acid
      residues.
<220> FEATURE:
<221> NAME/KEY: MISC_FEATURE
<222> LOCATION: (423)..(423)
<223> OTHER INFORMATION: Xaa is Gly or Arg.
<220> FEATURE:
<221> NAME/KEY: MISC_FEATURE
<222> LOCATION: (424)..(424)
<223> OTHER INFORMATION: Xaa is Ser or Lys.
<220> FEATURE:
<221> NAME/KEY: MISC_FEATURE
<222> LOCATION: (425)..(425)
<223> OTHER INFORMATION: Xaa is Asn or Ala.
<220> FEATURE:
<221> NAME/KEY: MISC_FEATURE
<222> LOCATION: (429)..(429)
<223> OTHER INFORMATION: Xaa is Asn or Lys.
<220> FEATURE:
<221> NAME/KEY: MISC_FEATURE
<222> LOCATION: (431)..(445)
<223> OTHER INFORMATION: Xaa represents 5 to 15 arbitrary amino acid
      residues.
<220> FEATURE:
<221> NAME/KEY: MISC_FEATURE
<222> LOCATION: (447)..(447)
<223> OTHER INFORMATION: Xaa is Asp or Gly.
<220> FEATURE:
<221> NAME/KEY: MISC_FEATURE
<222> LOCATION: (448)..(448)
<223> OTHER INFORMATION: Xaa is Glu or Ser.
<220> FEATURE:
<221> NAME/KEY: MISC_FEATURE
<222> LOCATION: (449)..(449)
<223> OTHER INFORMATION: Xaa is His or Asp.
<220> FEATURE:
<221> NAME/KEY: MISC_FEATURE
```

```
<222> LOCATION: (450)..(450)
<223> OTHER INFORMATION: Xaa is Arg or Trp.
<220> FEATURE:
<221> NAME/KEY: MISC_FEATURE
<222> LOCATION: (451)..(451)
<223> OTHER INFORMATION: Xaa is Ser or Trp.
<220> FEATURE:
<221> NAME/KEY: MISC_FEATURE
<222> LOCATION: (453)..(453)
<223> OTHER INFORMATION: Xaa is Ser or Asn.
<220> FEATURE:
<221> NAME/KEY: MISC_FEATURE
<222> LOCATION: (454)..(454)
<223> OTHER INFORMATION: Xaa is Pro or Glu.
<220> FEATURE:
<221> NAME/KEY: MISC_FEATURE
<222> LOCATION: (456)..(470)
<223> OTHER INFORMATION: Xaa represents 5 to 15 arbitrary amino acid
      residues.
<220> FEATURE:
<221> NAME/KEY: MISC_FEATURE
<222> LOCATION: (477)..(477)
<223> OTHER INFORMATION: Xaa is Met or Ala.
<220> FEATURE:
<221> NAME/KEY: MISC_FEATURE
<222> LOCATION: (479)..(479)
<223> OTHER INFORMATION: Xaa is Ser or Pro.

<400> SEQUENCE: 3

Met Xaa Ser Gly Xaa Xaa Xaa Xaa Xaa Xaa Xaa Xaa Xaa Asn Xaa
1               5                   10                  15

Xaa Asp Thr Xaa Asn Ala Ala Ala Xaa Ala Ile Xaa Xaa Xaa Xaa
                20                  25                  30

Arg Xaa Xaa Xaa Xaa Xaa Xaa Xaa Xaa Xaa Arg Lys Trp Xaa Xaa
                35                  40                  45

Xaa Xaa Ser Xaa Xaa Xaa Cys Phe Gly Ser Xaa Xaa Xaa Xaa Arg
            50                  55                  60

Ile Xaa Xaa Xaa Val Leu Val Pro Glu Pro Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Pro Phe Xaa Ala Pro Pro Ser Ser Pro Ala Ser Phe Xaa
            100                 105                 110

Gln Ser Xaa Xaa Xaa Ser Xaa Xaa Gln Ser Pro Val Gly Xaa Xaa Ser
            115                 120                 125

Phe Ser Pro Leu Xaa Xaa Asn Xaa Xaa Xaa Xaa Xaa Xaa Xaa Xaa
130                 135                 140

Xaa Pro Ser Ile Phe Ala Ile Gly Pro Tyr Ala His Glu Thr Gln Leu
145                 150                 155                 160

Val Ser Pro Pro Val Phe Ser Xaa Xaa Thr Thr Glu Pro Ser Xaa Ala
                165                 170                 175

Pro Xaa Thr Pro Pro Xaa Xaa Xaa Xaa Xaa Ser Xaa Xaa Leu Thr Thr
            180                 185                 190

Xaa Xaa Xaa Xaa Xaa Pro Ser Ser Pro Glu Val Pro Xaa Ala Xaa Leu
            195                 200                 205

Xaa Xaa Ser Xaa Xaa Xaa Xaa Xaa Xaa Xaa Xaa Xaa Xaa Xaa Xaa
            210                 215                 220

Xaa Xaa Xaa Xaa Xaa Xaa Glu Xaa Gln Xaa Tyr Gln Xaa Pro
225                 230                 235                 240

Xaa Ser Pro Xaa Gly Xaa Leu Ile Ser Pro Ser Xaa Xaa Xaa Xaa
            245                 250                 255

Ser Gly Xaa Xaa Ser Pro Phe Pro Asp Xaa Xaa Xaa Xaa Xaa Xaa
```

```
                260                 265                 270
Xaa Xaa Xaa Ser Xaa Phe Pro Xaa Phe Xaa Val Xaa Xaa Pro Pro Lys
            275                 280                 285

Xaa Leu Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Gly Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa His Xaa Xaa Xaa Xaa Val Ser Phe Xaa Leu
            340                 345                 350

Xaa Xaa Xaa Xaa Val Xaa Arg Cys Xaa Xaa Xaa Lys Xaa Xaa Xaa
            355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Pro Xaa Xaa Ser Xaa Asp Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Ser Leu Xaa Xaa Xaa Lys Glu Phe Xaa Phe Xaa
            420                 425                 430

Xaa Xaa Xaa Xaa Xaa Xaa Xaa Xaa Xaa Xaa Xaa Xaa Val Xaa Xaa
            435                 440                 445

Xaa Xaa Xaa Ala Xaa Xaa Lys Xaa Xaa Xaa Xaa Xaa Xaa Xaa Xaa
    450                 455                 460

Xaa Xaa Xaa Xaa Xaa Xaa Trp Ser Phe Phe Pro Val Xaa Gln Xaa Gly
465                 470                 475                 480

<210> SEQ ID NO 4
<211> LENGTH: 468
<212> TYPE: PRT
<213> ORGANISM: Unknown
<220> FEATURE:
<223> OTHER INFORMATION: Consensus motif
<220> FEATURE:
<221> NAME/KEY: MISC_FEATURE
<222> LOCATION: (3)..(5)
<223> OTHER INFORMATION: Xaa represents 0 to 3 arbitrary amino acid
      residues.
<220> FEATURE:
<221> NAME/KEY: MISC_FEATURE
<222> LOCATION: (10)..(14)
<223> OTHER INFORMATION: Xaa represents 0 to 5 arbitrary amino acid
      residues.
<220> FEATURE:
<221> NAME/KEY: MISC_FEATURE
<222> LOCATION: (17)..(17)
<223> OTHER INFORMATION: Xaa is Val or Thr.
<220> FEATURE:
<221> NAME/KEY: MISC_FEATURE
<222> LOCATION: (18)..(18)
<223> OTHER INFORMATION: Xaa is Phe or Leu.
<220> FEATURE:
<221> NAME/KEY: MISC_FEATURE
<222> LOCATION: (19)..(19)
<223> OTHER INFORMATION: Xaa is Asp or Glu.
<220> FEATURE:
<221> NAME/KEY: MISC_FEATURE
<222> LOCATION: (26)..(26)
<223> OTHER INFORMATION: Xaa is Ser or Thr.
<220> FEATURE:
<221> NAME/KEY: MISC_FEATURE
<222> LOCATION: (27)..(27)
<223> OTHER INFORMATION: Xaa is Ala or Val.
<220> FEATURE:
```

-continued

```
<221> NAME/KEY: MISC_FEATURE
<222> LOCATION: (31)..(31)
<223> OTHER INFORMATION: Xaa is Ser or Val.
<220> FEATURE:
<221> NAME/KEY: MISC_FEATURE
<222> LOCATION: (32)..(32)
<223> OTHER INFORMATION: Xaa is Asp or Glu.
<220> FEATURE:
<221> NAME/KEY: MISC_FEATURE
<222> LOCATION: (33)..(33)
<223> OTHER INFORMATION: Xaa is Asp or Asn.
<220> FEATURE:
<221> NAME/KEY: MISC_FEATURE
<222> LOCATION: (36)..(36)
<223> OTHER INFORMATION: Xaa is His or Asp.
<220> FEATURE:
<221> NAME/KEY: MISC_FEATURE
<222> LOCATION: (38)..(38)
<223> OTHER INFORMATION: Xaa is Ser or Pro.
<220> FEATURE:
<221> NAME/KEY: MISC_FEATURE
<222> LOCATION: (39)..(39)
<223> OTHER INFORMATION: Xaa is Ser or His.
<220> FEATURE:
<221> NAME/KEY: MISC_FEATURE
<222> LOCATION: (41)..(41)
<223> OTHER INFORMATION: Xaa is Ile or His.
<220> FEATURE:
<221> NAME/KEY: MISC_FEATURE
<222> LOCATION: (42)..(42)
<223> OTHER INFORMATION: Xaa is His or Val.
<220> FEATURE:
<221> NAME/KEY: MISC_FEATURE
<222> LOCATION: (43)..(43)
<223> OTHER INFORMATION: Xaa is Lys or Gln.
<220> FEATURE:
<221> NAME/KEY: MISC_FEATURE
<222> LOCATION: (45)..(45)
<223> OTHER INFORMATION: Xaa is Arg or Lys.
<220> FEATURE:
<221> NAME/KEY: MISC_FEATURE
<222> LOCATION: (46)..(46)
<223> OTHER INFORMATION: Xaa is Lys or Ser.
<220> FEATURE:
<221> NAME/KEY: MISC_FEATURE
<222> LOCATION: (48)..(48)
<223> OTHER INFORMATION: Xaa is Trp or Gly.
<220> FEATURE:
<221> NAME/KEY: MISC_FEATURE
<222> LOCATION: (50)..(50)
<223> OTHER INFORMATION: Xaa is Arg or Trp.
<220> FEATURE:
<221> NAME/KEY: MISC_FEATURE
<222> LOCATION: (51)..(51)
<223> OTHER INFORMATION: Xaa is Trp or Leu.
<220> FEATURE:
<221> NAME/KEY: MISC_FEATURE
<222> LOCATION: (53)..(53)
<223> OTHER INFORMATION: Xaa is Leu or Ile.
<220> FEATURE:
<221> NAME/KEY: MISC_FEATURE
<222> LOCATION: (54)..(54)
<223> OTHER INFORMATION: Xaa is Leu or Tyr.
<220> FEATURE:
<221> NAME/KEY: MISC_FEATURE
<222> LOCATION: (55)..(55)
<223> OTHER INFORMATION: Xaa is Lys or Trp.
<220> FEATURE:
<221> NAME/KEY: MISC_FEATURE
<222> LOCATION: (59)..(59)
<223> OTHER INFORMATION: Xaa is Ser or His.
<220> FEATURE:
<221> NAME/KEY: MISC_FEATURE
<222> LOCATION: (60)..(60)
<223> OTHER INFORMATION: Xaa is Ser or Arg.
<220> FEATURE:
<221> NAME/KEY: MISC_FEATURE
<222> LOCATION: (61)..(61)
<223> OTHER INFORMATION: Xaa is Arg or Lys.
```

-continued

```
<220> FEATURE:
<221> NAME/KEY: MISC_FEATURE
<222> LOCATION: (62)..(62)
<223> OTHER INFORMATION: Xaa is Gln or Asn.
<220> FEATURE:
<221> NAME/KEY: MISC_FEATURE
<222> LOCATION: (64)..(64)
<223> OTHER INFORMATION: Xaa is Lys or Gln.
<220> FEATURE:
<221> NAME/KEY: MISC_FEATURE
<222> LOCATION: (68)..(68)
<223> OTHER INFORMATION: Xaa is Asn or His.
<220> FEATURE:
<221> NAME/KEY: MISC_FEATURE
<222> LOCATION: (69)..(69)
<223> OTHER INFORMATION: Xaa is Ser or Ala.
<220> FEATURE:
<221> NAME/KEY: MISC_FEATURE
<222> LOCATION: (75)..(75)
<223> OTHER INFORMATION: Xaa is Pro or Arg.
<220> FEATURE:
<221> NAME/KEY: MISC_FEATURE
<222> LOCATION: (76)..(76)
<223> OTHER INFORMATION: Xaa is Val or Ile.
<220> FEATURE:
<221> NAME/KEY: MISC_FEATURE
<222> LOCATION: (77)..(77)
<223> OTHER INFORMATION: Xaa is Ser or Pro.
<220> FEATURE:
<221> NAME/KEY: MISC_FEATURE
<222> LOCATION: (78)..(78)
<223> OTHER INFORMATION: Xaa is Met or Ser.
<220> FEATURE:
<221> NAME/KEY: MISC_FEATURE
<222> LOCATION: (79)..(79)
<223> OTHER INFORMATION: Xaa is Ser or Gly.
<220> FEATURE:
<221> NAME/KEY: MISC_FEATURE
<222> LOCATION: (80)..(80)
<223> OTHER INFORMATION: Xaa is Ser or Thr.
<220> FEATURE:
<221> NAME/KEY: MISC_FEATURE
<222> LOCATION: (81)..(81)
<223> OTHER INFORMATION: Xaa is Ser or Asp.
<220> FEATURE:
<221> NAME/KEY: MISC_FEATURE
<222> LOCATION: (83)..(83)
<223> OTHER INFORMATION: Xaa is Ser or Ala.
<220> FEATURE:
<221> NAME/KEY: MISC_FEATURE
<222> LOCATION: (85)..(99)
<223> OTHER INFORMATION: Xaa represents 5 to 15 arbitrary amino acid
      residues.
<220> FEATURE:
<221> NAME/KEY: MISC_FEATURE
<222> LOCATION: (101)..(101)
<223> OTHER INFORMATION: Xaa is Thr or Ile.
<220> FEATURE:
<221> NAME/KEY: MISC_FEATURE
<222> LOCATION: (102)..(102)
<223> OTHER INFORMATION: Xaa is Thr or Pro.
<220> FEATURE:
<221> NAME/KEY: MISC_FEATURE
<222> LOCATION: (103)..(103)
<223> OTHER INFORMATION: Xaa is Leu or Phe.
<220> FEATURE:
<221> NAME/KEY: MISC_FEATURE
<222> LOCATION: (104)..(104)
<223> OTHER INFORMATION: Xaa is Pro or His.
<220> FEATURE:
<221> NAME/KEY: MISC_FEATURE
<222> LOCATION: (106)..(106)
<223> OTHER INFORMATION: Xaa is Ile or Val.
<220> FEATURE:
<221> NAME/KEY: MISC_FEATURE
<222> LOCATION: (116)..(116)
<223> OTHER INFORMATION: Xaa is Phe or Leu.
<220> FEATURE:
<221> NAME/KEY: MISC_FEATURE
```

```
<222> LOCATION: (117)..(117)
<223> OTHER INFORMATION: Xaa is Gln or His.
<220> FEATURE:
<221> NAME/KEY: MISC_FEATURE
<222> LOCATION: (123)..(123)
<223> OTHER INFORMATION: Xaa is Ala or Val.
<220> FEATURE:
<221> NAME/KEY: MISC_FEATURE
<222> LOCATION: (124)..(124)
<223> OTHER INFORMATION: Xaa is Thr or Ala.
<220> FEATURE:
<221> NAME/KEY: MISC_FEATURE
<222> LOCATION: (128)..(128)
<223> OTHER INFORMATION: Xaa is Val or Ser.
<220> FEATURE:
<221> NAME/KEY: MISC_FEATURE
<222> LOCATION: (129)..(129)
<223> OTHER INFORMATION: Xaa is Gly or Ala.
<220> FEATURE:
<221> NAME/KEY: MISC_FEATURE
<222> LOCATION: (133)..(133)
<223> OTHER INFORMATION: Xaa is Phe or Leu.
<220> FEATURE:
<221> NAME/KEY: MISC_FEATURE
<222> LOCATION: (134)..(134)
<223> OTHER INFORMATION: Xaa is Ser or Thr.
<220> FEATURE:
<221> NAME/KEY: MISC_FEATURE
<222> LOCATION: (136)..(145)
<223> OTHER INFORMATION: Xaa represents 1 to 10 arbitrary amino acid
      residues.
<220> FEATURE:
<221> NAME/KEY: MISC_FEATURE
<222> LOCATION: (168)..(168)
<223> OTHER INFORMATION: Xaa is Tyr or Phe.
<220> FEATURE:
<221> NAME/KEY: MISC_FEATURE
<222> LOCATION: (174)..(174)
<223> OTHER INFORMATION: Xaa is Ser or Thr.
<220> FEATURE:
<221> NAME/KEY: MISC_FEATURE
<222> LOCATION: (177)..(177)
<223> OTHER INFORMATION: Xaa is Ile or Phe.
<220> FEATURE:
<221> NAME/KEY: MISC_FEATURE
<222> LOCATION: (181)..(195)
<223> OTHER INFORMATION: Xaa represents 3 to 15 arbitrary amino acid
      residues.
<220> FEATURE:
<221> NAME/KEY: MISC_FEATURE
<222> LOCATION: (209)..(209)
<223> OTHER INFORMATION: Xaa is Phe or Leu.
<220> FEATURE:
<221> NAME/KEY: MISC_FEATURE
<222> LOCATION: (210)..(210)
<223> OTHER INFORMATION: Xaa is Asn or Asp.
<220> FEATURE:
<221> NAME/KEY: MISC_FEATURE
<222> LOCATION: (211)..(211)
<223> OTHER INFORMATION: Xaa is Ser or Pro.
<220> FEATURE:
<221> NAME/KEY: MISC_FEATURE
<222> LOCATION: (213)..(213)
<223> OTHER INFORMATION: Xaa is His or Asn.
<220> FEATURE:
<221> NAME/KEY: MISC_FEATURE
<222> LOCATION: (214)..(214)
<223> OTHER INFORMATION: Xaa is Gln or Lys.
<220> FEATURE:
<221> NAME/KEY: MISC_FEATURE
<222> LOCATION: (215)..(215)
<223> OTHER INFORMATION: Xaa is Thr or Asn.
<220> FEATURE:
<221> NAME/KEY: MISC_FEATURE
<222> LOCATION: (216)..(216)
<223> OTHER INFORMATION: Xaa is Gly or Ser.
<220> FEATURE:
<221> NAME/KEY: MISC_FEATURE
<222> LOCATION: (217)..(217)
```

```
<223> OTHER INFORMATION: Xaa is Ser or Glu.
<220> FEATURE:
<221> NAME/KEY: MISC_FEATURE
<222> LOCATION: (218)..(218)
<223> OTHER INFORMATION: Xaa is Tyr or Thr.
<220> FEATURE:
<221> NAME/KEY: MISC_FEATURE
<222> LOCATION: (219)..(219)
<223> OTHER INFORMATION: Xaa is Gly or Tyr.
<220> FEATURE:
<221> NAME/KEY: MISC_FEATURE
<222> LOCATION: (220)..(220)
<223> OTHER INFORMATION: Xaa is Tyr or Gln.
<220> FEATURE:
<221> NAME/KEY: MISC_FEATURE
<222> LOCATION: (221)..(221)
<223> OTHER INFORMATION: Xaa is Lys or Arg.
<220> FEATURE:
<221> NAME/KEY: MISC_FEATURE
<222> LOCATION: (223)..(229)
<223> OTHER INFORMATION: Xaa represents 3 to 7 arbitrary amino acid
      residues.
<220> FEATURE:
<221> NAME/KEY: MISC_FEATURE
<222> LOCATION: (231)..(231)
<223> OTHER INFORMATION: Xaa is Glu or Asp.
<220> FEATURE:
<221> NAME/KEY: MISC_FEATURE
<222> LOCATION: (233)..(233)
<223> OTHER INFORMATION: Xaa is Gln or His.
<220> FEATURE:
<221> NAME/KEY: MISC_FEATURE
<222> LOCATION: (234)..(234)
<223> OTHER INFORMATION: Xaa is Phe or Ser.
<220> FEATURE:
<221> NAME/KEY: MISC_FEATURE
<222> LOCATION: (238)..(238)
<223> OTHER INFORMATION: Xaa is Pro or His.
<220> FEATURE:
<221> NAME/KEY: MISC_FEATURE
<222> LOCATION: (243)..(243)
<223> OTHER INFORMATION: Xaa is Leu or Val.
<220> FEATURE:
<221> NAME/KEY: MISC_FEATURE
<222> LOCATION: (250)..(259)
<223> OTHER INFORMATION: Xaa represents 1 to 10 arbitrary amino acid
      residues.
<220> FEATURE:
<221> NAME/KEY: MISC_FEATURE
<222> LOCATION: (261)..(261)
<223> OTHER INFORMATION: Xaa is Gly or Ser.
<220> FEATURE:
<221> NAME/KEY: MISC_FEATURE
<222> LOCATION: (262)..(262)
<223> OTHER INFORMATION: Xaa is Pro or Thr.
<220> FEATURE:
<221> NAME/KEY: MISC_FEATURE
<222> LOCATION: (263)..(263)
<223> OTHER INFORMATION: Xaa is Thr or Ser.
<220> FEATURE:
<221> NAME/KEY: MISC_FEATURE
<222> LOCATION: (269)..(278)
<223> OTHER INFORMATION: Xaa represents 1 to 10 arbitrary amino acid
      residues.
<220> FEATURE:
<221> NAME/KEY: MISC_FEATURE
<222> LOCATION: (281)..(281)
<223> OTHER INFORMATION: Xaa is Phe or Leu.
<220> FEATURE:
<221> NAME/KEY: MISC_FEATURE
<222> LOCATION: (282)..(282)
<223> OTHER INFORMATION: Xaa is Pro or Leu.
<220> FEATURE:
<221> NAME/KEY: MISC_FEATURE
<222> LOCATION: (283)..(283)
<223> OTHER INFORMATION: Xaa is His or Asn.
<220> FEATURE:
<221> NAME/KEY: MISC_FEATURE
<222> LOCATION: (286)..(286)
```

```
<223> OTHER INFORMATION: Xaa is Val or Thr.
<220> FEATURE:
<221> NAME/KEY: MISC_FEATURE
<222> LOCATION: (287)..(287)
<223> OTHER INFORMATION: Xaa is Ser or Asp.
<220> FEATURE:
<221> NAME/KEY: MISC_FEATURE
<222> LOCATION: (289)..(298)
<223> OTHER INFORMATION: Xaa represents 3 to 10 arbitrary amino acid
      residues.
<220> FEATURE:
<221> NAME/KEY: MISC_FEATURE
<222> LOCATION: (300)..(300)
<223> OTHER INFORMATION: Xaa is Pro or His.
<220> FEATURE:
<221> NAME/KEY: MISC_FEATURE
<222> LOCATION: (301)..(301)
<223> OTHER INFORMATION: Xaa is Lys or Gln.
<220> FEATURE:
<221> NAME/KEY: MISC_FEATURE
<222> LOCATION: (302)..(302)
<223> OTHER INFORMATION: Xaa is Thr or Gly.
<220> FEATURE:
<221> NAME/KEY: MISC_FEATURE
<222> LOCATION: (303)..(303)
<223> OTHER INFORMATION: Xaa is Ala or Ser.
<220> FEATURE:
<221> NAME/KEY: MISC_FEATURE
<222> LOCATION: (305)..(305)
<223> OTHER INFORMATION: Xaa is Val or Ser.
<220> FEATURE:
<221> NAME/KEY: MISC_FEATURE
<222> LOCATION: (306)..(306)
<223> OTHER INFORMATION: Xaa is Thr or Leu.
<220> FEATURE:
<221> NAME/KEY: MISC_FEATURE
<222> LOCATION: (309)..(318)
<223> OTHER INFORMATION: Xaa represents 1 to 10 arbitrary amino acid
      residues.
<220> FEATURE:
<221> NAME/KEY: MISC_FEATURE
<222> LOCATION: (320)..(320)
<223> OTHER INFORMATION: Xaa is Lys or Ala.
<220> FEATURE:
<221> NAME/KEY: MISC_FEATURE
<222> LOCATION: (321)..(321)
<223> OTHER INFORMATION: Xaa is Ile or Ser.
<220> FEATURE:
<221> NAME/KEY: MISC_FEATURE
<222> LOCATION: (322)..(322)
<223> OTHER INFORMATION: Xaa is Val or Phe.
<220> FEATURE:
<221> NAME/KEY: MISC_FEATURE
<222> LOCATION: (323)..(323)
<223> OTHER INFORMATION: Xaa is Pro or Leu.
<220> FEATURE:
<221> NAME/KEY: MISC_FEATURE
<222> LOCATION: (325)..(325)
<223> OTHER INFORMATION: Xaa is His or Ser.
<220> FEATURE:
<221> NAME/KEY: MISC_FEATURE
<222> LOCATION: (326)..(326)
<223> OTHER INFORMATION: Xaa is Lys or His.
<220> FEATURE:
<221> NAME/KEY: MISC_FEATURE
<222> LOCATION: (327)..(327)
<223> OTHER INFORMATION: Xaa is Pro or Trp.
<220> FEATURE:
<221> NAME/KEY: MISC_FEATURE
<222> LOCATION: (330)..(330)
<223> OTHER INFORMATION: Xaa is Phe or Ile.
<220> FEATURE:
<221> NAME/KEY: MISC_FEATURE
<222> LOCATION: (331)..(331)
<223> OTHER INFORMATION: Xaa is Asp or Glu.
<220> FEATURE:
<221> NAME/KEY: MISC_FEATURE
<222> LOCATION: (332)..(332)
<223> OTHER INFORMATION: Xaa is Leu or Val.
```

```
<220> FEATURE:
<221> NAME/KEY: MISC_FEATURE
<222> LOCATION: (333)..(333)
<223> OTHER INFORMATION: Xaa is Asp or Ser.
<220> FEATURE:
<221> NAME/KEY: MISC_FEATURE
<222> LOCATION: (335)..(335)
<223> OTHER INFORMATION: Xaa is Asp or Gln.
<220> FEATURE:
<221> NAME/KEY: MISC_FEATURE
<222> LOCATION: (336)..(336)
<223> OTHER INFORMATION: Xaa is His or Glu.
<220> FEATURE:
<221> NAME/KEY: MISC_FEATURE
<222> LOCATION: (338)..(338)
<223> OTHER INFORMATION: Xaa is Ile or Phe.
<220> FEATURE:
<221> NAME/KEY: MISC_FEATURE
<222> LOCATION: (339)..(339)
<223> OTHER INFORMATION: Xaa is Arg or Asn.
<220> FEATURE:
<221> NAME/KEY: MISC_FEATURE
<222> LOCATION: (342)..(356)
<223> OTHER INFORMATION: Xaa represents 1 to 15 arbitrary amino acid
      residues.
<220> FEATURE:
<221> NAME/KEY: MISC_FEATURE
<222> LOCATION: (359)..(359)
<223> OTHER INFORMATION: Xaa is Arg or Lys.
<220> FEATURE:
<221> NAME/KEY: MISC_FEATURE
<222> LOCATION: (361)..(361)
<223> OTHER INFORMATION: Xaa is Thr or Asp.
<220> FEATURE:
<221> NAME/KEY: MISC_FEATURE
<222> LOCATION: (362)..(362)
<223> OTHER INFORMATION: Xaa is Phe or Ala.
<220> FEATURE:
<221> NAME/KEY: MISC_FEATURE
<222> LOCATION: (364)..(378)
<223> OTHER INFORMATION: Xaa represents 0 to 15 arbitrary amino acid
      residues.
<220> FEATURE:
<221> NAME/KEY: MISC_FEATURE
<222> LOCATION: (380)..(380)
<223> OTHER INFORMATION: Xaa is Ala or Thr.
<220> FEATURE:
<221> NAME/KEY: MISC_FEATURE
<222> LOCATION: (381)..(381)
<223> OTHER INFORMATION: Xaa is Ser or Pro.
<220> FEATURE:
<221> NAME/KEY: MISC_FEATURE
<222> LOCATION: (384)..(398)
<223> OTHER INFORMATION: Xaa represents 1 to 15 arbitrary amino acid
      residues.
<220> FEATURE:
<221> NAME/KEY: MISC_FEATURE
<222> LOCATION: (400)..(400)
<223> OTHER INFORMATION: Xaa is Ser or Arg.
<220> FEATURE:
<221> NAME/KEY: MISC_FEATURE
<222> LOCATION: (401)..(401)
<223> OTHER INFORMATION: Xaa is Met or Val.
<220> FEATURE:
<221> NAME/KEY: MISC_FEATURE
<222> LOCATION: (402)..(402)
<223> OTHER INFORMATION: Xaa is Asn or His.
<220> FEATURE:
<221> NAME/KEY: MISC_FEATURE
<222> LOCATION: (404)..(413)
<223> OTHER INFORMATION: Xaa represents 5 to 10 arbitrary amino acid
      residues.
<220> FEATURE:
<221> NAME/KEY: MISC_FEATURE
<222> LOCATION: (419)..(419)
<223> OTHER INFORMATION: Xaa is Gly or Asp.
<220> FEATURE:
<221> NAME/KEY: MISC_FEATURE
<222> LOCATION: (420)..(420)
```

```
<223> OTHER INFORMATION: Xaa is Thr or Asn.
<220> FEATURE:
<221> NAME/KEY: MISC_FEATURE
<222> LOCATION: (421)..(421)
<223> OTHER INFORMATION: Xaa is Asp or Ala.
<220> FEATURE:
<221> NAME/KEY: MISC_FEATURE
<222> LOCATION: (423)..(432)
<223> OTHER INFORMATION: Xaa represents 1 to 10 arbitrary amino acid
      residues.
<220> FEATURE:
<221> NAME/KEY: MISC_FEATURE
<222> LOCATION: (434)..(434)
<223> OTHER INFORMATION: Xaa is Thr or Val.
<220> FEATURE:
<221> NAME/KEY: MISC_FEATURE
<222> LOCATION: (435)..(435)
<223> OTHER INFORMATION: Xaa is Val or Ala.
<220> FEATURE:
<221> NAME/KEY: MISC_FEATURE
<222> LOCATION: (437)..(446)
<223> OTHER INFORMATION: Xaa represents 1 to 10 arbitrary amino acid
      residues.
<220> FEATURE:
<221> NAME/KEY: MISC_FEATURE
<222> LOCATION: (449)..(455)
<223> OTHER INFORMATION: Xaa represents 1 to 7 arbitrary amino acid
      residues.
<220> FEATURE:
<221> NAME/KEY: MISC_FEATURE
<222> LOCATION: (458)..(458)
<223> OTHER INFORMATION: Xaa is Asp or Asn.
<220> FEATURE:
<221> NAME/KEY: MISC_FEATURE
<222> LOCATION: (464)..(464)
<223> OTHER INFORMATION: Xaa is Val or Met.
<220> FEATURE:
<221> NAME/KEY: MISC_FEATURE
<222> LOCATION: (465)..(465)
<223> OTHER INFORMATION: Xaa is Met or Ile.
<220> FEATURE:
<221> NAME/KEY: MISC_FEATURE
<222> LOCATION: (466)..(466)
<223> OTHER INFORMATION: Xaa is Gln or Arg.
<220> FEATURE:
<221> NAME/KEY: MISC_FEATURE
<222> LOCATION: (467)..(467)
<223> OTHER INFORMATION: Xaa is Ser or Pro.

<400> SEQUENCE: 4

Met Arg Xaa Xaa Xaa Gly Ala Asn Gly Xaa Xaa Xaa Xaa Xaa Asn Asn
1               5                   10                  15

Xaa Xaa Xaa Thr Ile Asn Ala Ala Ala Xaa Xaa Ile Ala Ser Xaa Xaa
            20                  25                  30

Xaa Arg Leu Xaa Gln Xaa Xaa Pro Xaa Xaa Xaa Lys Xaa Xaa Trp Xaa
        35                  40                  45

Asn Xaa Xaa Ser Xaa Xaa Xaa Cys Phe Gly Xaa Xaa Xaa Xaa Arg Xaa
    50                  55                  60

Arg Ile Gly Xaa Xaa Val Leu Val Pro Glu Xaa Xaa Xaa Xaa Xaa Xaa
65                  70                  75                  80

Xaa Asn Xaa Thr Xaa Xaa Xaa Xaa Xaa Xaa Xaa Xaa Xaa Xaa Xaa Xaa
            85                  90                  95

Xaa Xaa Xaa Ile Xaa Xaa Xaa Xaa Phe Xaa Ala Pro Pro Ser Ser Pro
            100                 105                 110

Ala Ser Phe Xaa Xaa Ser Glu Pro Pro Ser Xaa Xaa Gln Ser Pro Xaa
            115                 120                 125

Xaa Ile Leu Ser Xaa Xaa Pro Xaa Xaa Xaa Xaa Xaa Xaa Xaa Xaa Xaa
            130                 135                 140

Xaa Ser Ile Phe Ala Ile Gly Pro Tyr Ala His Glu Thr Gln Leu Val
```

```
            145                 150                 155                 160
Ser Pro Pro Val Phe Ser Thr Xaa Thr Thr Glu Pro Ser Xaa Ala Pro
                165                 170                 175

Xaa Thr Pro Pro Xaa Xaa Xaa Xaa Xaa Xaa Xaa Xaa Xaa Xaa Xaa Xaa
            180                 185                 190

Xaa Xaa Xaa Thr Thr Pro Ser Ser Pro Glu Val Pro Phe Ala Gln Leu
            195                 200                 205

Xaa Xaa Xaa Asn Xaa Xaa Xaa Xaa Xaa Xaa Xaa Xaa Phe Xaa Xaa
        210                 215                 220

Xaa Xaa Xaa Xaa Xaa Tyr Xaa Phe Xaa Xaa Tyr Gln Leu Xaa Pro Gly
225                 230                 235                 240

Ser Pro Xaa Gly Gln Leu Ile Ser Pro Xaa Xaa Xaa Xaa Xaa Xaa
            245                 250                 255

Xaa Xaa Xaa Ser Xaa Xaa Xaa Ser Pro Phe Pro Asp Xaa Xaa Xaa Xaa
            260                 265                 270

Xaa Xaa Xaa Xaa Xaa Xaa Ser Leu Xaa Xaa Xaa Phe Gln Xaa Xaa Asp
            275                 280                 285

Xaa Xaa Xaa Xaa Xaa Xaa Xaa Xaa Ser Xaa Xaa Xaa Xaa Gly
        290                 295                 300

Xaa Xaa Thr Pro Xaa Xaa Xaa Xaa Xaa Xaa Xaa Xaa Gln Xaa
305                 310                 315                 320

Xaa Xaa Xaa Pro Xaa Xaa Xaa Val Ser Xaa Xaa Xaa Ala Xaa Xaa
            325                 330                 335

Val Xaa Xaa Cys Val Xaa Xaa Xaa Xaa Xaa Xaa Xaa Xaa Xaa
            340                 345                 350

Xaa Xaa Xaa Xaa Lys Leu Xaa Thr Xaa Xaa Pro Xaa Xaa Xaa Xaa Xaa
            355                 360                 365

Xaa Xaa Xaa Xaa Xaa Xaa Xaa Xaa Glu Xaa Xaa Ser Asp Xaa
            370                 375                 380

Xaa Xaa Xaa Xaa Xaa Xaa Xaa Xaa Xaa Xaa Xaa Xaa Glu Xaa
385                 390                 395                 400

Xaa Xaa His Xaa Xaa Xaa Xaa Xaa Xaa Xaa Xaa Xaa Lys Glu Phe
            405                 410                 415

Asn Phe Xaa Xaa Xaa Glu Xaa Xaa Xaa Xaa Xaa Xaa Xaa Xaa
            420                 425                 430

Leu Xaa Xaa Asp Xaa Xaa Xaa Xaa Xaa Xaa Xaa Xaa Ala Ser
            435                 440                 445

Xaa Xaa Xaa Xaa Xaa Xaa Xaa Ser Asn Xaa Trp Ser Phe Phe Pro Xaa
            450                 455                 460

Xaa Xaa Xaa Gly
465

<210> SEQ ID NO 5
<211> LENGTH: 444
<212> TYPE: PRT
<213> ORGANISM: Unknown
<220> FEATURE:
<223> OTHER INFORMATION: Consensus motif
<220> FEATURE:
<221> NAME/KEY: MISC_FEATURE
<222> LOCATION: (5)..(5)
<223> OTHER INFORMATION: Xaa is Ser or Gly.
<220> FEATURE:
<221> NAME/KEY: MISC_FEATURE
<222> LOCATION: (6)..(6)
<223> OTHER INFORMATION: Xaa is Glu or Asp.
<220> FEATURE:
<221> NAME/KEY: MISC_FEATURE
```

```
<222> LOCATION: (34)..(34)
<223> OTHER INFORMATION: Xaa is Gln or Pro.
<220> FEATURE:
<221> NAME/KEY: MISC_FEATURE
<222> LOCATION: (37)..(37)
<223> OTHER INFORMATION: Xaa is Pro or Gln.
<220> FEATURE:
<221> NAME/KEY: MISC_FEATURE
<222> LOCATION: (44)..(44)
<223> OTHER INFORMATION: Xaa is Trp or Arg.
<220> FEATURE:
<221> NAME/KEY: MISC_FEATURE
<222> LOCATION: (59)..(63)
<223> OTHER INFORMATION: Xaa represents 0 to 5 arbitrary amino acid
      residues.
<220> FEATURE:
<221> NAME/KEY: MISC_FEATURE
<222> LOCATION: (65)..(65)
<223> OTHER INFORMATION: Xaa is Ile or Val.
<220> FEATURE:
<221> NAME/KEY: MISC_FEATURE
<222> LOCATION: (66)..(66)
<223> OTHER INFORMATION: Xaa is Ser or Asn.
<220> FEATURE:
<221> NAME/KEY: MISC_FEATURE
<222> LOCATION: (69)..(69)
<223> OTHER INFORMATION: Xaa is Val or Ala.
<220> FEATURE:
<221> NAME/KEY: MISC_FEATURE
<222> LOCATION: (75)..(75)
<223> OTHER INFORMATION: Xaa is Leu or Ala.
<220> FEATURE:
<221> NAME/KEY: MISC_FEATURE
<222> LOCATION: (77)..(77)
<223> OTHER INFORMATION: Xaa is Pro or Gln.
<220> FEATURE:
<221> NAME/KEY: MISC_FEATURE
<222> LOCATION: (83)..(83)
<223> OTHER INFORMATION: Xaa is Met or Ala.
<220> FEATURE:
<221> NAME/KEY: MISC_FEATURE
<222> LOCATION: (84)..(84)
<223> OTHER INFORMATION: Xaa is Pro or Ala.
<220> FEATURE:
<221> NAME/KEY: MISC_FEATURE
<222> LOCATION: (88)..(88)
<223> OTHER INFORMATION: Xaa is Ile or Asn.
<220> FEATURE:
<221> NAME/KEY: MISC_FEATURE
<222> LOCATION: (111)..(111)
<223> OTHER INFORMATION: Xaa is Gly or Glu.
<220> FEATURE:
<221> NAME/KEY: MISC_FEATURE
<222> LOCATION: (112)..(112)
<223> OTHER INFORMATION: Xaa is Gly or Pro.
<220> FEATURE:
<221> NAME/KEY: MISC_FEATURE
<222> LOCATION: (113)..(113)
<223> OTHER INFORMATION: Xaa is Ala or Thr.
<220> FEATURE:
<221> NAME/KEY: MISC_FEATURE
<222> LOCATION: (120)..(124)
<223> OTHER INFORMATION: Xaa represents 0 to 5 arbitrary amino acid
      residues.
<220> FEATURE:
<221> NAME/KEY: MISC_FEATURE
<222> LOCATION: (128)..(128)
<223> OTHER INFORMATION: Xaa is Ser or Ala.
<220> FEATURE:
<221> NAME/KEY: MISC_FEATURE
<222> LOCATION: (137)..(137)
<223> OTHER INFORMATION: Xaa is Pro or Gln.
<220> FEATURE:
<221> NAME/KEY: MISC_FEATURE
<222> LOCATION: (207)..(207)
<223> OTHER INFORMATION: Xaa is Ala or Gly.
<220> FEATURE:
<221> NAME/KEY: MISC_FEATURE
<222> LOCATION: (209)..(209)
```

```
<223> OTHER INFORMATION: Xaa is Thr or Ala.
<220> FEATURE:
<221> NAME/KEY: MISC_FEATURE
<222> LOCATION: (211)..(215)
<223> OTHER INFORMATION: Xaa represents 0 to 5 arbitrary amino acid
      residues.
<220> FEATURE:
<221> NAME/KEY: MISC_FEATURE
<222> LOCATION: (220)..(220)
<223> OTHER INFORMATION: Xaa is Gln or Pro.
<220> FEATURE:
<221> NAME/KEY: MISC_FEATURE
<222> LOCATION: (221)..(221)
<223> OTHER INFORMATION: Xaa is Ile or Asn.
<220> FEATURE:
<221> NAME/KEY: MISC_FEATURE
<222> LOCATION: (224)..(224)
<223> OTHER INFORMATION: Xaa is Glu or Asp.
<220> FEATURE:
<221> NAME/KEY: MISC_FEATURE
<222> LOCATION: (236)..(236)
<223> OTHER INFORMATION: Xaa is Ala or Gly.
<220> FEATURE:
<221> NAME/KEY: MISC_FEATURE
<222> LOCATION: (241)..(241)
<223> OTHER INFORMATION: Xaa is Cys or Ser.
<220> FEATURE:
<221> NAME/KEY: MISC_FEATURE
<222> LOCATION: (249)..(249)
<223> OTHER INFORMATION: Xaa is Val or Met.
<220> FEATURE:
<221> NAME/KEY: MISC_FEATURE
<222> LOCATION: (251)..(251)
<223> OTHER INFORMATION: Xaa is Thr or Ala.
<220> FEATURE:
<221> NAME/KEY: MISC_FEATURE
<222> LOCATION: (256)..(256)
<223> OTHER INFORMATION: Xaa is Thr or Ala.
<220> FEATURE:
<221> NAME/KEY: MISC_FEATURE
<222> LOCATION: (257)..(257)
<223> OTHER INFORMATION: Xaa is Phe or Leu.
<220> FEATURE:
<221> NAME/KEY: MISC_FEATURE
<222> LOCATION: (258)..(258)
<223> OTHER INFORMATION: Xaa is Pro or Arg.
<220> FEATURE:
<221> NAME/KEY: MISC_FEATURE
<222> LOCATION: (259)..(259)
<223> OTHER INFORMATION: Xaa is Ser or Leu.
<220> FEATURE:
<221> NAME/KEY: MISC_FEATURE
<222> LOCATION: (274)..(274)
<223> OTHER INFORMATION: Xaa is Ile or Val.
<220> FEATURE:
<221> NAME/KEY: MISC_FEATURE
<222> LOCATION: (294)..(294)
<223> OTHER INFORMATION: Xaa is His or Gln.
<220> FEATURE:
<221> NAME/KEY: MISC_FEATURE
<222> LOCATION: (310)..(310)
<223> OTHER INFORMATION: Xaa is Asn or Pro.
<220> FEATURE:
<221> NAME/KEY: MISC_FEATURE
<222> LOCATION: (312)..(312)
<223> OTHER INFORMATION: Xaa is Asp or Glu.
<220> FEATURE:
<221> NAME/KEY: MISC_FEATURE
<222> LOCATION: (337)..(337)
<223> OTHER INFORMATION: Xaa is Asn or Ala.
<220> FEATURE:
<221> NAME/KEY: MISC_FEATURE
<222> LOCATION: (339)..(339)
<223> OTHER INFORMATION: Xaa is Asn or Ser.
<220> FEATURE:
<221> NAME/KEY: MISC_FEATURE
<222> LOCATION: (341)..(341)
<223> OTHER INFORMATION: Xaa is Glu or Asp.
<220> FEATURE:
```

```
<221> NAME/KEY: MISC_FEATURE
<222> LOCATION: (343)..(343)
<223> OTHER INFORMATION: Xaa is Ala or Gly.
<220> FEATURE:
<221> NAME/KEY: MISC_FEATURE
<222> LOCATION: (344)..(344)
<223> OTHER INFORMATION: Xaa is Ala or Thr.
<220> FEATURE:
<221> NAME/KEY: MISC_FEATURE
<222> LOCATION: (348)..(348)
<223> OTHER INFORMATION: Xaa is Arg or His.
<220> FEATURE:
<221> NAME/KEY: MISC_FEATURE
<222> LOCATION: (350)..(350)
<223> OTHER INFORMATION: Xaa is Val or Ala.
<220> FEATURE:
<221> NAME/KEY: MISC_FEATURE
<222> LOCATION: (354)..(354)
<223> OTHER INFORMATION: Xaa is Asn or Ser.
<220> FEATURE:
<221> NAME/KEY: MISC_FEATURE
<222> LOCATION: (357)..(361)
<223> OTHER INFORMATION: Xaa represents 0 to 5 arbitrary amino acid
      residues.
<220> FEATURE:
<221> NAME/KEY: MISC_FEATURE
<222> LOCATION: (363)..(363)
<223> OTHER INFORMATION: Xaa is Pro or His.
<220> FEATURE:
<221> NAME/KEY: MISC_FEATURE
<222> LOCATION: (368)..(368)
<223> OTHER INFORMATION: Xaa is Asp or Glu.
<220> FEATURE:
<221> NAME/KEY: MISC_FEATURE
<222> LOCATION: (369)..(369)
<223> OTHER INFORMATION: Xaa is Thr or Ala.
<220> FEATURE:
<221> NAME/KEY: MISC_FEATURE
<222> LOCATION: (374)..(374)
<223> OTHER INFORMATION: Xaa is Cys or Tyr.
<220> FEATURE:
<221> NAME/KEY: MISC_FEATURE
<222> LOCATION: (378)..(378)
<223> OTHER INFORMATION: Xaa is Thr or Ser.
<220> FEATURE:
<221> NAME/KEY: MISC_FEATURE
<222> LOCATION: (394)..(394)
<223> OTHER INFORMATION: Xaa is Lys or Leu.
<220> FEATURE:
<221> NAME/KEY: MISC_FEATURE
<222> LOCATION: (399)..(399)
<223> OTHER INFORMATION: Xaa is Lys or Asn.
<220> FEATURE:
<221> NAME/KEY: MISC_FEATURE
<222> LOCATION: (405)..(405)
<223> OTHER INFORMATION: Xaa is Ala or Val.
<220> FEATURE:
<221> NAME/KEY: MISC_FEATURE
<222> LOCATION: (406)..(406)
<223> OTHER INFORMATION: Xaa is Pro or Gly.
<220> FEATURE:
<221> NAME/KEY: MISC_FEATURE
<222> LOCATION: (425)..(425)
<223> OTHER INFORMATION: Xaa is Ile or Met.
<220> FEATURE:
<221> NAME/KEY: MISC_FEATURE
<222> LOCATION: (427)..(427)
<223> OTHER INFORMATION: Xaa is Ser or Thr.
<220> FEATURE:
<221> NAME/KEY: MISC_FEATURE
<222> LOCATION: (430)..(430)
<223> OTHER INFORMATION: Xaa is Arg or Lys.
<220> FEATURE:
<221> NAME/KEY: MISC_FEATURE
<222> LOCATION: (432)..(432)
<223> OTHER INFORMATION: Xaa is Ser or Asn.
<220> FEATURE:
<221> NAME/KEY: MISC_FEATURE
<222> LOCATION: (436)..(436)
```

```
<223> OTHER INFORMATION: Xaa is Phe or His.
<220> FEATURE:
<221> NAME/KEY: MISC_FEATURE
<222> LOCATION: (439)..(439)
<223> OTHER INFORMATION: Xaa is Ala or Val.

<400> SEQUENCE: 5

Met Gln Ser Gly Xaa Xaa Met Arg Pro Val His Asn Ser Val Asp Thr
1               5                   10                  15

Val Asn Ala Ala Ala Val Ala Ile Val Thr Ala Glu Ser Arg Thr Gln
            20                  25                  30

Pro Xaa Ala Glu Xaa Arg Arg Lys Trp Ala Asp Xaa Leu Ser Val Tyr
        35                  40                  45

Phe Cys Phe Gly Ser Gln Lys Asn Gly Arg Xaa Xaa Xaa Xaa Xaa Arg
50                  55                  60

Xaa Xaa His Ala Xaa Leu Val Pro Glu Pro Xaa Pro Xaa Arg Thr Asp
65                  70                  75                  80

Ala Pro Xaa Xaa Glu Ile Pro Xaa His Pro Pro Pro Val Phe Pro
            85                  90                  95

Phe Val Ala Pro Pro Ser Ser Pro Ala Ser Phe Leu Gln Ser Xaa Xaa
            100                 105                 110

Xaa Ser Ile Val Gln Ser Pro Xaa Xaa Xaa Xaa Gly Ala Pro Xaa
    115                 120                 125

Phe Ser Pro Leu Ser Pro Asn Ser Xaa Ser Pro Thr Gly Pro Pro Ser
130                 135                 140

Ile Phe Ala Ile Gly Pro Tyr Ala His Glu Thr Gln Leu Val Ser Pro
145                 150                 155                 160

Pro Val Phe Ser Ala Phe Thr Thr Glu Pro Ser Thr Ala Pro Phe Thr
                165                 170                 175

Pro Pro Pro Glu Ser Val His Leu Thr Thr Pro Ser Ser Pro Glu Val
            180                 185                 190

Pro Tyr Ala Lys Leu Leu Thr Ser Ile Asn Asn Ser Lys Asn Xaa Glu
        195                 200                 205

Xaa Gly Xaa Xaa Xaa Xaa Xaa Leu Gln Ser Tyr Xaa Xaa Tyr Pro Xaa
    210                 215                 220

Ser Pro Ile Gly Arg Leu Ile Ser Pro Ser Xaa Cys Ser Gly Thr
225                 230                 235                 240

Xaa Ser Pro Phe Pro Asp Pro Glu Xaa Gln Xaa Ser Ser Arg Ser Xaa
                245                 250                 255

Xaa Xaa Xaa Phe Pro Val Arg Glu Pro Pro Lys Ile Leu Asp Gly Glu
        260                 265                 270

Gly Xaa Ala Thr Gln Lys Leu Ile Pro Arg His Met Arg Asn Gly Gly
    275                 280                 285

Ser Leu Leu Asp Gly Xaa Ile Ser Ala Ala Val Pro Val Val Asp Phe
290                 295                 300

Ser Ala Arg Leu Gln Xaa Asn Xaa His Ala Met Asp His Arg Val Ser
305                 310                 315                 320

Phe Glu Leu Thr Val Glu Asp Val Ala Arg Cys Leu Glu Lys Lys Thr
                325                 330                 335

Xaa Ile Xaa Gly Xaa Ser Xaa Xaa Ala Ser Phe Xaa Leu Xaa Pro Thr
        340                 345                 350

Gly Xaa Gly Asp Xaa Xaa Xaa Xaa His Xaa Arg Glu Ser Asn Xaa
    355                 360                 365

Xaa Arg Ala Gly Leu Xaa Val Asp Glu Xaa Tyr His Asp Leu Pro Glu
370                 375                 380
```

```
Lys Ala Arg Arg Ser Leu Ser Leu Arg Xaa Ala Lys Glu Phe Xaa Phe
385                 390                 395                 400

Asn Asn Val Asp Xaa Xaa Ser Val Glu Pro Ser Val Gly Ser Asp Trp
                405                 410                 415

Trp Ala Asn Glu Lys Val Ala Gly Xaa Thr Xaa Glu Pro Xaa Lys Xaa
            420                 425                 430

Trp Ser Phe Xaa Pro Val Xaa Gln Pro Gly Val Ser
        435                 440

<210> SEQ ID NO 6
<211> LENGTH: 1524
<212> TYPE: DNA
<213> ORGANISM: Arabidopsis thaliana
<220> FEATURE:
<221> NAME/KEY: CDS
<222> LOCATION: (182)..(1258)

<400> SEQUENCE: 6
```

| | |
|---|---|
| attcccagaa atttcggggt tacgtgtcgc tttatttgta aaacgatttt tcagattttg | 60 |
| attgttaaag aagctttctg tgtattattt ttgattttta ctagagaaaa actcgaatgc | 120 |
| tctgttttgt tctctcgaga aaattctcag actcagagaa aagtaaaaac agagaagaaa | 180 |

```
g atg aga agc ggt gct aat gga aac aac gtt ttc gat act ata aac gca       229
  Met Arg Ser Gly Ala Asn Gly Asn Asn Val Phe Asp Thr Ile Asn Ala
  1               5                   10                  15 gct gct tct gct att gct tct tct gat gat cgt ctt cat caa tct tct       277
Ala Ala Ser Ala Ile Ala Ser Ser Asp Asp Arg Leu His Gln Ser Ser
            20                  25                  30 ccg att cat aag aag aga aaa tgg tgg aat cga tgg agt ctg ttg aaa       325
Pro Ile His Lys Lys Arg Lys Trp Trp Asn Arg Trp Ser Leu Leu Lys
        35                  40                  45 tgt ttc gga tct tca aga caa aga aaa cga ata gga aac tcg gtt ctt       373
Cys Phe Gly Ser Ser Arg Gln Arg Lys Arg Ile Gly Asn Ser Val Leu
    50                  55                  60 gtt cct gaa ccg gta tca atg tct tct tca aat tca aca aca tca aat       421
Val Pro Glu Pro Val Ser Met Ser Ser Ser Asn Ser Thr Thr Ser Asn
65                  70                  75                  80 tcc ggt tat cgt tcg gtt atc aca aca ctt cct ttt ata gct cca cct       469
Ser Gly Tyr Arg Ser Val Ile Thr Thr Leu Pro Phe Ile Ala Pro Pro
                85                  90                  95 tca tct cca gct tca ttt ttc caa tca gag cca cct tct gct aca caa       517
Ser Ser Pro Ala Ser Phe Phe Gln Ser Glu Pro Pro Ser Ala Thr Gln
            100                 105                 110 tca cct gtt gga atc ctc tct ttt agt cct ttg cct tgt aac aac cgt       565
Ser Pro Val Gly Ile Leu Ser Phe Ser Pro Leu Pro Cys Asn Asn Arg
        115                 120                 125 cct tcc atc ttc gcc att gga cct tac gct cat gaa act caa ttg gta       613
Pro Ser Ile Phe Ala Ile Gly Pro Tyr Ala His Glu Thr Gln Leu Val
    130                 135                 140 tct cct ccg gtt ttc tca act tac act act gaa cca tct tca gct cca       661
Ser Pro Pro Val Phe Ser Thr Tyr Thr Thr Glu Pro Ser Ser Ala Pro
145                 150                 155                 160 atc aca cct cct ctt gat gac tca tct atc tac tta acc acc aca aca       709
Ile Thr Pro Pro Leu Asp Asp Ser Ser Ile Tyr Leu Thr Thr Thr Thr
                165                 170                 175 cct tct tca cct gaa gtg cct ttt gct cag ctc ttt aac tcg aac cat       757
Pro Ser Ser Pro Glu Val Pro Phe Ala Gln Leu Phe Asn Ser Asn His
            180                 185                 190 caa acc ggt agc tat ggt tat aag ttc cca atg tct tct agt tat gag       805
Gln Thr Gly Ser Tyr Gly Tyr Lys Phe Pro Met Ser Ser Ser Tyr Glu
```

```
Gln Thr Gly Ser Tyr Gly Tyr Lys Phe Pro Met Ser Ser Tyr Glu
            195                 200                 205 ttt cag ttt tac caa ctt cct cct ggt agt cca ctt ggt cag ctt att        853
Phe Gln Phe Tyr Gln Leu Pro Pro Gly Ser Pro Leu Gly Gln Leu Ile
210                 215                 220 tcc ccg agc cct ggt tct ggt cca act tct cct ttt ccc gat gga gaa        901
Ser Pro Ser Pro Gly Ser Gly Pro Thr Ser Pro Phe Pro Asp Gly Glu
225                 230                 235                 240 acc tcg ctg ttc cct cac ttt caa gtc tct gat cct cca aaa ctg ttg        949
Thr Ser Leu Phe Pro His Phe Gln Val Ser Asp Pro Pro Lys Leu Leu
            245                 250                 255 agt cca aag act gct ggt gtt aca act cct tgt aaa gag cag aag att        997
Ser Pro Lys Thr Ala Gly Val Thr Thr Pro Cys Lys Glu Gln Lys Ile
        260                 265                 270 gta aga ccg cat aaa ccg gtt tca ttc gat ctt gat gct gat cat gtc       1045
Val Arg Pro His Lys Pro Val Ser Phe Asp Leu Asp Ala Asp His Val
        275                 280                 285 att aga tgc gtg gat cag aag cta aga aca acg ttc cct gaa gca tca       1093
Ile Arg Cys Val Asp Gln Lys Leu Arg Thr Thr Phe Pro Glu Ala Ser
290                 295                 300 tca gat caa gaa tca atg aat cat tcg tct ctc ggg tcc aat aag gaa       1141
Ser Asp Gln Glu Ser Met Asn His Ser Ser Leu Gly Ser Asn Lys Glu
305                 310                 315                 320 ttc aat ttc ggc acg gat gag aaa cat ttg acc gtt gat gaa cat aga       1189
Phe Asn Phe Gly Thr Asp Glu Lys His Leu Thr Val Asp Glu His Arg
            325                 330                 335 tca gct tcg ccg aag aac agc aat gat tgg tct ttt ttc cct gtg atg       1237
Ser Ala Ser Pro Lys Asn Ser Asn Asp Trp Ser Phe Phe Pro Val Met
        340                 345                 350 cag tca ggt aca cta agc taa ccttcatcag aagaatagaa atctgaaatt          1288
Gln Ser Gly Thr Leu Ser
            355 tagatatcga ttcggacaaa tatcttgttc aagattcaag aacaattata gaattttag      1348 atgattctgt tcaggatctt aaggatattt tcttgtctct cttttggtt ttgtaataaa      1408 tatttggcat cgttagttgt tgtatatggc tactctttat gtagtttttt gttttttgtga   1468 atacacattt gatcgcattt gtaaataaaa tttaatcagt ttcttcggag aaattc         1524

<210> SEQ ID NO 7
<211> LENGTH: 358
<212> TYPE: PRT
<213> ORGANISM: Arabidopsis thaliana

<400> SEQUENCE: 7

Met Arg Ser Gly Ala Asn Gly Asn Asn Val Phe Asp Thr Ile Asn Ala
1               5                   10                  15

Ala Ala Ser Ala Ile Ala Ser Ser Asp Asp Arg Leu His Gln Ser Ser
            20                  25                  30

Pro Ile His Lys Lys Arg Lys Trp Trp Asn Arg Trp Ser Leu Leu Lys
        35                  40                  45

Cys Phe Gly Ser Ser Arg Gln Arg Lys Arg Ile Gly Asn Ser Val Leu
    50                  55                  60

Val Pro Glu Pro Val Ser Met Ser Ser Asn Ser Thr Ser Asn
65                  70                  75                  80

Ser Gly Tyr Arg Ser Val Ile Thr Thr Leu Pro Phe Ile Ala Pro Pro
                85                  90                  95

Ser Ser Pro Ala Ser Phe Phe Gln Ser Glu Pro Pro Ser Ala Thr Gln
            100                 105                 110
```

Ser Pro Val Gly Ile Leu Ser Phe Ser Pro Leu Pro Cys Asn Asn Arg
        115                 120                 125

Pro Ser Ile Phe Ala Ile Gly Pro Tyr Ala His Glu Thr Gln Leu Val
        130                 135                 140

Ser Pro Pro Val Phe Ser Thr Tyr Thr Thr Glu Pro Ser Ser Ala Pro
145                 150                 155                 160

Ile Thr Pro Pro Leu Asp Asp Ser Ser Ile Tyr Leu Thr Thr Thr Thr
                165                 170                 175

Pro Ser Ser Pro Glu Val Pro Phe Ala Gln Leu Phe Asn Ser Asn His
                180                 185                 190

Gln Thr Gly Ser Tyr Gly Tyr Lys Phe Pro Met Ser Ser Tyr Glu
        195                 200                 205

Phe Gln Phe Tyr Gln Leu Pro Pro Gly Ser Pro Leu Gly Gln Leu Ile
        210                 215                 220

Ser Pro Ser Pro Gly Ser Gly Pro Thr Ser Pro Phe Pro Asp Gly Glu
225                 230                 235                 240

Thr Ser Leu Phe Pro His Phe Gln Val Ser Asp Pro Pro Lys Leu Leu
                245                 250                 255

Ser Pro Lys Thr Ala Gly Val Thr Thr Pro Cys Lys Glu Gln Lys Ile
                260                 265                 270

Val Arg Pro His Lys Pro Val Ser Phe Asp Leu Asp Ala Asp His Val
        275                 280                 285

Ile Arg Cys Val Asp Gln Lys Leu Arg Thr Thr Phe Pro Glu Ala Ser
        290                 295                 300

Ser Asp Gln Glu Ser Met Asn His Ser Ser Leu Gly Ser Asn Lys Glu
305                 310                 315                 320

Phe Asn Phe Gly Thr Asp Glu Lys His Leu Thr Val Asp Glu His Arg
                325                 330                 335

Ser Ala Ser Pro Lys Asn Ser Asn Asp Trp Ser Phe Phe Pro Val Met
                340                 345                 350

Gln Ser Gly Thr Leu Ser
        355

<210> SEQ ID NO 8
<211> LENGTH: 1909
<212> TYPE: DNA
<213> ORGANISM: Glycine max
<220> FEATURE:
<221> NAME/KEY: CDS
<222> LOCATION: (193)..(1431)

<400> SEQUENCE: 8
tatacacaac aagctcgtac cataggatat acaaactata cagagattga ttttattttc    60
aattgatctc ttagcaaaac aaacatttgt caagtatcaa ctttcacgcc tctacgattt   120
caagcttgtt tgttttggg tatgtagtaa atctagaaaa atctgctttt gtaaagaaaa   180
aaggtactag ag atg aga ggt gct aat gga ggc gct gtg aac aac act ttg    231
         Met Arg Gly Ala Asn Gly Gly Ala Val Asn Asn Thr Leu
           1               5                   10 gag act atc aac gct gct gca act gtc atc gct tcc gtc gag aat cgc    279
Glu Thr Ile Asn Ala Ala Ala Thr Val Ile Ala Ser Val Glu Asn Arg
    15                  20                  25 ctt gat caa ccc cat cct cac gtc cag aag aaa agc tgg gga aac tgg    327
Leu Asp Gln Pro His Pro His Val Gln Lys Lys Ser Trp Gly Asn Trp
30                  35                  40                  45 tta agc ata tat tgg tgt ttt gga cat cgc aaa aac cga cag cgc att    375

```
Leu Ser Ile Tyr Trp Cys Phe Gly His Arg Lys Asn Arg Gln Arg Ile
             50              55                  60 ggg cat gca gtc ctt gtt ccc gaa aga ata cct tct ggc aca gat aat       423
Gly His Ala Val Leu Val Pro Glu Arg Ile Pro Ser Gly Thr Asp Asn
             65              70                  75 gca aca gta aat tca aca caa gca cct att atc cca ttc cac ttc gtt       471
Ala Thr Val Asn Ser Thr Gln Ala Pro Ile Ile Pro Phe His Phe Val
             80              85                  90 gca cct ccc tca tct cct gca tct ttc ctt cac tca gaa cct cct tca       519
Ala Pro Pro Ser Ser Pro Ala Ser Phe Leu His Ser Glu Pro Pro Ser
    95                  100                 105 gtt gca caa tcc cca agt gct ata cta tct ctc act ccc ggt ggt cct       567
Val Ala Gln Ser Pro Ser Ala Ile Leu Ser Leu Thr Pro Gly Gly Pro
110                 115                 120                 125 ttc tct atc ttt gcc att gga cct tat gcc cac gaa aca caa tta gtt       615
Phe Ser Ile Phe Ala Ile Gly Pro Tyr Ala His Glu Thr Gln Leu Val
                130                 135                 140 tca cca cct gtt ttc tca aca ttc acc aca gaa cca tca acc gct cct       663
Ser Pro Pro Val Phe Ser Thr Phe Thr Thr Glu Pro Ser Thr Ala Pro
            145                 150                 155 ttc act ccc cct cct gaa tct aac cac ttg act aca cct tct tca cct       711
Phe Thr Pro Pro Pro Glu Ser Asn His Leu Thr Thr Pro Ser Ser Pro
            160                 165                 170 gaa gtg cca ttt gct caa ctg ctt gac ccc aac aac aaa aat agt gaa       759
Glu Val Pro Phe Ala Gln Leu Leu Asp Pro Asn Asn Lys Asn Ser Glu
            175                 180                 185 acc tat cag agg ttc caa ata cct cag tat gat ttc cac tct tat cag       807
Thr Tyr Gln Arg Phe Gln Ile Pro Gln Tyr Asp Phe His Ser Tyr Gln
190                 195                 200                 205 ctt cat ccc gga agc ccg gtt ggt caa ctc att tca cca aga tct gct       855
Leu His Pro Gly Ser Pro Val Gly Gln Leu Ile Ser Pro Arg Ser Ala
                210                 215                 220 ttc tca gct tct agc aca tca tct cct ttc cct gac act gac act gag       903
Phe Ser Ala Ser Ser Thr Ser Ser Pro Phe Pro Asp Thr Asp Thr Glu
            225                 230                 235 ttt aat tct cgc gcc tcc ctc ctc ctt aac ttt caa aca gat gat aaa       951
Phe Asn Ser Arg Ala Ser Leu Leu Leu Asn Phe Gln Thr Asp Asp Lys
            240                 245                 250 ctg tct act aat gaa aac cat aag tca cat caa ggt tct ggc tct cta       999
Leu Ser Thr Asn Glu Asn His Lys Ser His Gln Gly Ser Gly Ser Leu
255                 260                 265 acc cca gat tct ata aga tcc aca act caa gct agt ttt ctt cca agt       1047
Thr Pro Asp Ser Ile Arg Ser Thr Thr Gln Ala Ser Phe Leu Pro Ser
270                 275                 280                 285 cac tgg gtc tct att gaa gtg tct gcc caa gaa gta ttc aat tgt gtg       1095
His Trp Val Ser Ile Glu Val Ser Ala Gln Glu Val Phe Asn Cys Val
                290                 295                 300 gaa aac aag gca gtg gca tgg act aaa cca ctt tca aaa ctc aaa act       1143
Glu Asn Lys Ala Val Ala Trp Thr Lys Pro Leu Ser Lys Leu Lys Thr
            305                 310                 315 gat gca ccg gga gaa gat aat tca aga gaa gtc ctt gtc atc gaa act       1191
Asp Ala Pro Gly Glu Asp Asn Ser Arg Glu Val Leu Val Ile Glu Thr
            320                 325                 330 ccc agt gat gca cca caa cag acc gct gac gat gga gat gtg gaa aga       1239
Pro Ser Asp Ala Pro Gln Gln Thr Ala Asp Asp Gly Asp Val Glu Arg
335                 340                 345 gtt cat cat aag gat gaa tgt ata aca ttt tct gct gct aaa gaa ttc       1287
Val His His Lys Asp Glu Cys Ile Thr Phe Ser Ala Ala Lys Glu Phe
350                 355                 360                 365
```

-continued

```
aac ttt gat aat gca gaa gga ggg gat tct cct act cct aat tta gtt    1335
Asn Phe Asp Asn Ala Glu Gly Gly Asp Ser Pro Thr Pro Asn Leu Val
                370                 375                 380 gct gac tgg tgg gct aag gag aaa gtt gca agc aag gaa gga gga tcc    1383
Ala Asp Trp Trp Ala Lys Glu Lys Val Ala Ser Lys Glu Gly Gly Ser
            385                 390                 395 tct aat aat tgg tct ttc ttc cca atg att cga ccc ggt gtt ggt taa    1431
Ser Asn Asn Trp Ser Phe Phe Pro Met Ile Arg Pro Gly Val Gly
            400                 405                 410 tcgccaataa ggactcactt agtttagtga ctttcactta acatagcctt gctggaattt    1491 gacattttt  tttttttata aaaaaaattg tgcaattgtg tcacagcagc caacaccagt    1551
acaccacccc tgctaaattg aatcataggc aactaagaat tttacattgg tagatctaac    1611
aaatagaaag gtggagataa ttttgcagac tagctataaa ttttgcaggt aaacctactt    1671
tggattagga atggctttac atttataaca tctccattct ccacacccgt tctttatcct    1731
ttttgtttgt aagtgtaata cagttgtcat caacacattg gttaccaata accaatgatg    1791
attttgattt ttgactatga tgtgtttttt tattgcccct tgccttgact gtaattgtag    1851
gaatgcaatt gcagaacttg gagaagggga ggaaaccttg tgtgaaacat tttagcaa      1909
```

<210> SEQ ID NO 9
<211> LENGTH: 412
<212> TYPE: PRT
<213> ORGANISM: Glycine max

<400> SEQUENCE: 9

```
Met Arg Gly Ala Asn Gly Gly Ala Val Asn Asn Thr Leu Glu Thr Ile
1               5                   10                  15

Asn Ala Ala Ala Thr Val Ile Ala Ser Val Glu Asn Arg Leu Asp Gln
            20                  25                  30

Pro His Pro His Val Gln Lys Lys Ser Trp Gly Asn Trp Leu Ser Ile
        35                  40                  45

Tyr Trp Cys Phe Gly His Arg Lys Asn Arg Gln Arg Ile Gly His Ala
    50                  55                  60

Val Leu Val Pro Glu Arg Ile Pro Ser Gly Thr Asp Asn Ala Thr Val
65                  70                  75                  80

Asn Ser Thr Gln Ala Pro Ile Ile Pro Phe His Phe Val Ala Pro Pro
                85                  90                  95

Ser Ser Pro Ala Ser Phe Leu His Ser Glu Pro Ser Val Ala Gln
            100                 105                 110

Ser Pro Ser Ala Ile Leu Ser Leu Thr Pro Gly Gly Pro Phe Ser Ile
        115                 120                 125

Phe Ala Ile Gly Pro Tyr Ala His Glu Thr Gln Leu Val Ser Pro Pro
    130                 135                 140

Val Phe Ser Thr Phe Thr Thr Glu Pro Ser Thr Ala Pro Phe Thr Pro
145                 150                 155                 160

Pro Pro Glu Ser Asn His Leu Thr Thr Pro Ser Ser Pro Glu Val Pro
                165                 170                 175

Phe Ala Gln Leu Leu Asp Pro Asn Asn Lys Asn Ser Glu Thr Tyr Gln
            180                 185                 190

Arg Phe Gln Ile Pro Gln Tyr Asp Phe His Ser Tyr Gln Leu His Pro
        195                 200                 205

Gly Ser Pro Val Gly Gln Leu Ile Ser Pro Arg Ser Ala Phe Ser Ala
    210                 215                 220

Ser Ser Thr Ser Ser Pro Phe Pro Asp Thr Asp Thr Glu Phe Asn Ser
```

```
                225                 230                 235                 240
        Arg Ala Ser Leu Leu Asn Phe Gln Thr Asp Asp Lys Leu Ser Thr
                        245                 250                 255

Asn Glu Asn His Lys Ser His Gln Gly Ser Gly Ser Leu Thr Pro Asp
                        260                 265                 270

Ser Ile Arg Ser Thr Thr Gln Ala Ser Phe Leu Pro Ser His Trp Val
                        275                 280                 285

Ser Ile Glu Val Ser Ala Gln Glu Val Phe Asn Cys Val Glu Asn Lys
                        290                 295                 300

Ala Val Ala Trp Thr Lys Pro Leu Ser Lys Leu Lys Thr Asp Ala Pro
        305                 310                 315                 320

Gly Glu Asp Asn Ser Arg Glu Val Leu Val Ile Glu Thr Pro Ser Asp
                        325                 330                 335

Ala Pro Gln Gln Thr Ala Asp Asp Gly Asp Val Glu Arg Val His His
                        340                 345                 350

Lys Asp Glu Cys Ile Thr Phe Ser Ala Ala Lys Glu Phe Asn Phe Asp
                        355                 360                 365

Asn Ala Glu Gly Gly Asp Ser Pro Thr Pro Asn Leu Val Ala Asp Trp
                        370                 375                 380

Trp Ala Lys Glu Lys Val Ala Ser Lys Glu Gly Gly Ser Ser Asn Asn
        385                 390                 395                 400

Trp Ser Phe Phe Pro Met Ile Arg Pro Gly Val Gly
                        405                 410

<210> SEQ ID NO 10
<211> LENGTH: 2049
<212> TYPE: DNA
<213> ORGANISM: Oryza sativa
<220> FEATURE:
<221> NAME/KEY: CDS
<222> LOCATION: (416)..(1702)

<400> SEQUENCE: 10
gtcttgtgct tctctcttcc ccggcagcgc gtccatcgaa gtagtagcat actactctct        60
actcctctcc tctcctctcc tccgctttgg tttgctccga tctgcagcga gagcgggagg       120
tcgtcgccgg cgaggaggcg cggcggagga atcctctcct tcctcttctt ggtctgcgag       180
taaagctcgg ccgccgccgg cgacgaactg gtttggggag agccacgtac ggcgccgcct       240
cgaatcgaat cgaattggag gttgatttga ctcgttggtt ggagcgctcc atcgattaag       300
cagacggagt catgcttctt ctttgggtat aaaagtttgg atctcggagg ctcgattcaa       360
tctctggagt gggaacaatc gtttgctcgt ggtcgtggga tagctcctct gcgag atg       418
                                                                Met
                                                                1 cag agt ggg agc gag atg aga ccc gtg cac aac agt gtc gac acg gtg        466
Gln Ser Gly Ser Glu Met Arg Pro Val His Asn Ser Val Asp Thr Val
        5                   10                  15 aac gcg gct gct gtt gcc att gtt aca gcc gag agc cgc acg caa cct        514
Asn Ala Ala Ala Val Ala Ile Val Thr Ala Glu Ser Arg Thr Gln Pro
            20                  25                  30 cag gca gag ccg cga aga aaa tgg gct gat tgg ttg agt gtg tac ttc        562
Gln Ala Glu Pro Arg Arg Lys Trp Ala Asp Trp Leu Ser Val Tyr Phe
        35                  40                  45 tgc ttt gga tca cag aaa aat ggc cga cgc atc agc cat gct gtt ctt        610
Cys Phe Gly Ser Gln Lys Asn Gly Arg Arg Ile Ser His Ala Val Leu
50                  55                  60                  65 gtc cca gaa cct tta cct ccg agg aca gat gca cct atg cca gaa att        658
```

```
                Val Pro Glu Pro Leu Pro Pro Arg Thr Asp Ala Pro Met Pro Glu Ile
                                    70                  75                  80 cca atc cat ccg cca ccc ccg gta ttc ccc ttt gtc gca cct cca tcc             706
Pro Ile His Pro Pro Pro Val Phe Pro Phe Val Ala Pro Pro Ser
            85                  90                  95 tct cct gct tct ttt ctc caa tca gga ggt gca tct att gta caa tca             754
Ser Pro Ala Ser Phe Leu Gln Ser Gly Gly Ala Ser Ile Val Gln Ser
            100                 105                 110 cct gtt ggt gct cca tct ttt tcg cct ctc tcg cca aat tct cca tcc             802
Pro Val Gly Ala Pro Ser Phe Ser Pro Leu Ser Pro Asn Ser Pro Ser
115                 120                 125 ccc act ggg cca ccg tcc atc ttt gct atc gga cca tat gca cat gag             850
Pro Thr Gly Pro Pro Ser Ile Phe Ala Ile Gly Pro Tyr Ala His Glu
130                 135                 140                 145 aca cag cta gtc tct cct cct gtc ttc tca gcc ttc aca act gaa cct             898
Thr Gln Leu Val Ser Pro Pro Val Phe Ser Ala Phe Thr Thr Glu Pro
                150                 155                 160 tca aca gct cct ttc act ccc cca cca gag tct gtg cat ctg aca acc             946
Ser Thr Ala Pro Phe Thr Pro Pro Pro Glu Ser Val His Leu Thr Thr
                165                 170                 175 cct tcc tca cca gag gtg cca tat gca aag cta ctt acc tca atc aac             994
Pro Ser Ser Pro Glu Val Pro Tyr Ala Lys Leu Leu Thr Ser Ile Asn
            180                 185                 190 aac agc aaa aat gct gaa aca ggt gag ctt cag tca tac cag att tac             1042
Asn Ser Lys Asn Ala Glu Thr Gly Glu Leu Gln Ser Tyr Gln Ile Tyr
195                 200                 205 cct gag agc cca ata gga cgt ctg ata tct cca agc tca gct tgt tca             1090
Pro Glu Ser Pro Ile Gly Arg Leu Ile Ser Pro Ser Ser Ala Cys Ser
210                 215                 220                 225 ggg act tgc tct cca ttt cct gac cct gag gtg cag act tcc tca cgt             1138
Gly Thr Cys Ser Pro Phe Pro Asp Pro Glu Val Gln Thr Ser Ser Arg
                230                 235                 240 tcc aca ttc ccc tca ttc cca gtt cgt gag cct cca aag ata ctg gat             1186
Ser Thr Phe Pro Ser Phe Pro Val Arg Glu Pro Pro Lys Ile Leu Asp
                245                 250                 255 ggc gag gga att gca aca cag aag ttg ata cct cgc cat atg cgc aat             1234
Gly Glu Gly Ile Ala Thr Gln Lys Leu Ile Pro Arg His Met Arg Asn
            260                 265                 270 ggc ggt tct ctc ttg gat gga cat att tct gct gct gta cca gtc gta             1282
Gly Gly Ser Leu Leu Asp Gly His Ile Ser Ala Ala Val Pro Val Val
275                 280                 285 gac ttc tct gcc cga ctt caa aat aat gat cat gct atg gat cat cgg             1330
Asp Phe Ser Ala Arg Leu Gln Asn Asn Asp His Ala Met Asp His Arg
290                 295                 300                 305 gtt tca ttt gag tta aca gta gaa gat gta gct cgc tgt ctt gag aag             1378
Val Ser Phe Glu Leu Thr Val Glu Asp Val Ala Arg Cys Leu Glu Lys
                310                 315                 320 aaa acc aac att aat ggg gag tct gct gca gct tct ttt cgc ctt gtg             1426
Lys Thr Asn Ile Asn Gly Glu Ser Ala Ala Ala Ser Phe Arg Leu Val
                325                 330                 335 ccc acc ggt aac gga gat cac att cat ccc aga gaa tcg aat gat aca             1474
Pro Thr Gly Asn Gly Asp His Ile His Pro Arg Glu Ser Asn Asp Thr
            340                 345                 350 aga gca ggg cta tgt gtt gat gaa aca tac cat gat ctg cct gag aaa             1522
Arg Ala Gly Leu Cys Val Asp Glu Thr Tyr His Asp Leu Pro Glu Lys
355                 360                 365 gca cgg cgc tcc ttg tcc ctt cgt aag gct aaa gaa ttc aag ttc aac             1570
Ala Arg Arg Ser Leu Ser Leu Arg Lys Ala Lys Glu Phe Lys Phe Asn
370                 375                 380                 385
```

-continued

| | | | | | | | | | | | | | | | | |
|---|---|---|---|---|---|---|---|---|---|---|---|---|---|---|---|---|
| aat | gtt | gat | gct | cct | agt | gtg | gag | ccg | agc | gtt | gga | tca | gac | tgg | tgg | 1618 |
| Asn | Val | Asp | Ala | Pro | Ser | Val | Glu | Pro | Ser | Val | Gly | Ser | Asp | Trp | Trp | |
| | | | 390 | | | | | 395 | | | | | 400 | | | |
| gca | aac | gag | aaa | gtt | gct | ggg | atc | aca | tca | gag | cca | agg | aaa | agc | tgg | 1666 |
| Ala | Asn | Glu | Lys | Val | Ala | Gly | Ile | Thr | Ser | Glu | Pro | Arg | Lys | Ser | Trp | |
| | | | 405 | | | | | 410 | | | | | 415 | | | |
| tcc | ttc | ttc | cca | gtg | gca | cag | cca | ggg | gtc | agc | taa | cagttgcact | | | | 1712 |
| Ser | Phe | Phe | Pro | Val | Ala | Gln | Pro | Gly | Val | Ser | | | | | | |
| | | | 420 | | | | | 425 | | | | | | | | | gaccataatc ttacaagatg aagaaataag cttctgtcat ttttgctcct gctgtttctc  1772 agttccccag ataccatcat cataactgca ggagatgcaa acttatgcaa aatattccag  1832 ttttagcggt aagttggagt tagttagtaa ctcagtgtcc agctaatatc atcataagat  1892 actaaaggtg atgcagattc tggaacctgt tgttataaaa ccataatact tccatggtgt  1952 agcgtctgtt gtatcctcct taactgactg gctgttctga tactgatgct gtttatgtac  2012 ataataaact agcgaaaaga gtagaactct tcctagc  2049

<210> SEQ ID NO 11
<211> LENGTH: 428
<212> TYPE: PRT
<213> ORGANISM: Oryza sativa

<400> SEQUENCE: 11

Met Gln Ser Gly Ser Glu Met Arg Pro Val His Asn Ser Val Asp Thr
1               5                   10                  15

Val Asn Ala Ala Val Ala Ile Val Thr Ala Glu Ser Arg Thr Gln
            20                  25                  30

Pro Gln Ala Glu Pro Arg Arg Lys Trp Ala Asp Trp Leu Ser Val Tyr
        35                  40                  45

Phe Cys Phe Gly Ser Gln Lys Asn Gly Arg Arg Ile Ser His Ala Val
    50                  55                  60

Leu Val Pro Glu Pro Leu Pro Pro Arg Thr Asp Ala Pro Met Pro Glu
65                  70                  75                  80

Ile Pro Ile His Pro Pro Pro Val Phe Pro Phe Val Ala Pro Pro
                85                  90                  95

Ser Ser Pro Ala Ser Phe Leu Gln Ser Gly Ala Ser Ile Val Gln
            100                 105                 110

Ser Pro Val Gly Ala Pro Ser Phe Ser Pro Leu Ser Pro Asn Ser Pro
        115                 120                 125

Ser Pro Thr Gly Pro Pro Ser Ile Phe Ala Ile Gly Pro Tyr Ala His
    130                 135                 140

Glu Thr Gln Leu Val Ser Pro Pro Val Phe Ser Ala Phe Thr Thr Glu
145                 150                 155                 160

Pro Ser Thr Ala Pro Phe Thr Pro Pro Glu Ser Val His Leu Thr
                165                 170                 175

Thr Pro Ser Ser Pro Glu Val Pro Tyr Ala Lys Leu Leu Thr Ser Ile
            180                 185                 190

Asn Asn Ser Lys Asn Ala Glu Thr Gly Glu Leu Gln Ser Tyr Gln Ile
        195                 200                 205

Tyr Pro Glu Ser Pro Ile Gly Arg Leu Ile Ser Pro Ser Ser Ala Cys
    210                 215                 220

Ser Gly Thr Cys Ser Pro Phe Pro Asp Pro Glu Val Gln Thr Ser Ser
225                 230                 235                 240

Arg Ser Thr Phe Pro Ser Phe Pro Val Arg Glu Pro Pro Lys Ile Leu
                245                 250                 255

```
Asp Gly Glu Gly Ile Ala Thr Gln Lys Leu Ile Pro Arg His Met Arg
            260                 265                 270

Asn Gly Gly Ser Leu Leu Asp Gly His Ile Ser Ala Ala Val Pro Val
        275                 280                 285

Val Asp Phe Ser Ala Arg Leu Gln Asn Asn Asp His Ala Met Asp His
    290                 295                 300

Arg Val Ser Phe Glu Leu Thr Val Glu Asp Val Ala Arg Cys Leu Glu
305                 310                 315                 320

Lys Lys Thr Asn Ile Asn Gly Glu Ser Ala Ala Ala Ser Phe Arg Leu
                325                 330                 335

Val Pro Thr Gly Asn Gly Asp His Ile His Pro Arg Glu Ser Asn Asp
            340                 345                 350

Thr Arg Ala Gly Leu Cys Val Asp Glu Thr Tyr His Asp Leu Pro Glu
        355                 360                 365

Lys Ala Arg Arg Ser Leu Ser Leu Arg Lys Ala Lys Glu Phe Lys Phe
    370                 375                 380

Asn Asn Val Asp Ala Pro Ser Val Glu Pro Ser Val Gly Ser Asp Trp
385                 390                 395                 400

Trp Ala Asn Glu Lys Val Ala Gly Ile Thr Ser Glu Pro Arg Lys Ser
                405                 410                 415

Trp Ser Phe Phe Pro Val Ala Gln Pro Gly Val Ser
            420                 425

<210> SEQ ID NO 12
<211> LENGTH: 2131
<212> TYPE: DNA
<213> ORGANISM: Zea mays
<220> FEATURE:
<221> NAME/KEY: CDS
<222> LOCATION: (359)..(1651)

<400> SEQUENCE: 12
gcactccctc cctgcccctg ttctctctct cgtggcgacg gcgacggcga cgactgggcg      60
gccgttgctg ccgccctact cgccaggcgc ccaggtattc ttcggcccct tcgccggcga     120
cgagtgtcac caggttcctc gtctccggaa cgcagtgcaa agcagatcga tctcggccca     180 gcagggggcct cacgacttga ctcccaaggg ctcccaacct tgcaggctga ctcgatctct     240
ttggtttcgt ggaccgtgat cagactccag ggctggatcg tgtttcttcc agtgtgcaag     300
cttggatctc gtaggtctgg tttagaaagg accgtgcttg ctctttgctg ccgcaatc       358 atg cag agt ggg ggc gac atg agg cct gtg cac aac agt gtc gat aca       406
Met Gln Ser Gly Gly Asp Met Arg Pro Val His Asn Ser Val Asp Thr
1               5                   10                  15 gtt aac gct gct gct gtt gcc atc gtc acc gcg gag agc cgc aca cag       454
Val Asn Ala Ala Ala Val Ala Ile Val Thr Ala Glu Ser Arg Thr Gln
            20                  25                  30 cct cct gct gaa cag aga agg aaa tgg gct gac cgg ttg agc gtg tac       502
Pro Pro Ala Glu Gln Arg Arg Lys Trp Ala Asp Arg Leu Ser Val Tyr
        35                  40                  45 ttc tgc ttt gga tca cag aag aat ggc cgg cgc atg cgt gtc aac cat       550
Phe Cys Phe Gly Ser Gln Lys Asn Gly Arg Arg Met Arg Val Asn His
    50                  55                  60 gcc gca ctt gtc cca gaa cct gca cct caa agg aca gat gcg cct gca       598
Ala Ala Leu Val Pro Glu Pro Ala Pro Gln Arg Thr Asp Ala Pro Ala
65                  70                  75                  80 gca gaa att cca aac cac cca ccg cct cct gtg ttc ccc ttt gtg gca       646
Ala Glu Ile Pro Asn His Pro Pro Pro Val Phe Pro Phe Val Ala
```

```
                    85                  90                  95
ccg cca tcc tct cct gct tct ttc ctt caa tca gaa ccc aca tca atc      694
Pro Pro Ser Ser Pro Ala Ser Phe Leu Gln Ser Glu Pro Thr Ser Ile
            100                 105                 110 gta caa tca cca agg gct gga gct cca gct ttt tcg ccc ctc tca cca      742
Val Gln Ser Pro Arg Ala Gly Ala Pro Ala Phe Ser Pro Leu Ser Pro
        115                 120                 125 aat tcc caa tcc ccg acg ggg cca cca tcc atc ttt gct att ggg ccg      790
Asn Ser Gln Ser Pro Thr Gly Pro Pro Ser Ile Phe Ala Ile Gly Pro
130                 135                 140 tat gca cat gag aca caa ctc gtc tcg cct cca gtg ttc tcg gcc ttc      838
Tyr Ala His Glu Thr Gln Leu Val Ser Pro Pro Val Phe Ser Ala Phe
145                 150                 155                 160 aca act gaa cca tca act gcc cct ttc act cct cct ccg gag tct gtc      886
Thr Thr Glu Pro Ser Thr Ala Pro Phe Thr Pro Pro Pro Glu Ser Val
                165                 170                 175 cat ctg aca acc cct tcc tct cca gag gtc cca tat gca aag ctt ctg      934
His Leu Thr Thr Pro Ser Ser Pro Glu Val Pro Tyr Ala Lys Leu Leu
            180                 185                 190 aca tcg atc aac aat agc aag aat ggt gaa gca ggg ggt gat ctc cag      982
Thr Ser Ile Asn Asn Ser Lys Asn Gly Glu Ala Gly Gly Asp Leu Gln
        195                 200                 205 tcg tat cca aac tac cca gac agc cca att ggg cgc ctg ata tct cca     1030
Ser Tyr Pro Asn Tyr Pro Asp Ser Pro Ile Gly Arg Leu Ile Ser Pro
    210                 215                 220 agc tcg ggc tgt tct ggc aca tcc tcc cca ttc cct gac cct gag atg     1078
Ser Ser Gly Cys Ser Gly Thr Ser Ser Pro Phe Pro Asp Pro Glu Met
225                 230                 235                 240 cag gct tct tca cgc agc gct tta cgc ttg ttc cca gtt cgt gag ccc     1126
Gln Ala Ser Ser Arg Ser Ala Leu Arg Leu Phe Pro Val Arg Glu Pro
                245                 250                 255 cct aag ata ttg gat ggc gag ggc gtt gcg aca cag aag ttg ata cct     1174
Pro Lys Ile Leu Asp Gly Glu Gly Val Ala Thr Gln Lys Leu Ile Pro
            260                 265                 270 cgc cat atg cgc aac ggt ggg tcc ctc ttg gat ggc cag atc tca gca     1222
Arg His Met Arg Asn Gly Gly Ser Leu Leu Asp Gly Gln Ile Ser Ala
        275                 280                 285 gct gta cca gtt gtg gac ttc tct gcc cga ctt caa ccc aac gag cac     1270
Ala Val Pro Val Val Asp Phe Ser Ala Arg Leu Gln Pro Asn Glu His
    290                 295                 300 gca atg gat cac cgg gtg tca ttc gag ttg acc gtc gaa gat gtc gcg     1318
Ala Met Asp His Arg Val Ser Phe Glu Leu Thr Val Glu Asp Val Ala
305                 310                 315                 320 cgc tgc ctt gag aag aag act gca atc tcc ggg gat tct ggc acg gca     1366
Arg Cys Leu Glu Lys Lys Thr Ala Ile Ser Gly Asp Ser Gly Thr Ala
                325                 330                 335 tca ttc cac ctt gca ccg acc ggc agc ggc gac cac cac aga gaa tcc     1414
Ser Phe His Leu Ala Pro Thr Gly Ser Gly Asp His His Arg Glu Ser
            340                 345                 350 aac gag gca agg gca ggg ctc tac gtc gac gaa tca tac cat gac ttg     1462
Asn Glu Ala Arg Ala Gly Leu Tyr Val Asp Glu Ser Tyr His Asp Leu
        355                 360                 365 ccc gag aaa gcg agg cgg tcc ctg tcc ctg cgc ctg gcc aaa gag ttc     1510
Pro Glu Lys Ala Arg Arg Ser Leu Ser Leu Arg Leu Ala Lys Glu Phe
    370                 375                 380 aat ttc aac aac gtc gac gtc ggt agc gtg gag ccg agc gtg gga tcc     1558
Asn Phe Asn Asn Val Asp Val Gly Ser Val Glu Pro Ser Val Gly Ser
385                 390                 395                 400 gac tgg tgg gcg aac gag aaa gtc gcc ggg atg aca act gag cca aaa     1606
```

```
Asp Trp Trp Ala Asn Glu Lys Val Ala Gly Met Thr Thr Glu Pro Lys
            405                 410                 415 aag aac tgg tct ttc cac ccg gtg gtg cag cct ggg gtc agc taa          1651
Lys Asn Trp Ser Phe His Pro Val Val Gln Pro Gly Val Ser
            420                 425                 430 cctttgcact gaccataatg atcttataca gggatgaagg aattagcttc ttctgcttct    1711
gcttctgctt cagtggtcga ttccttaggg atgacttgcc agcttgttct aaacatgcag    1771
ctagtggtaa gttctggatt tagatagtaa taagtaatgg ggtgtccacc gtctaatatc    1831
gtcatgggat actaaaggtt tttattctgg gagatgtgac aaaccgcaaa ctctttggtt    1891
aggggtcggt cggaactgtc ctgttcgtct gttttatcct gataccggtg ctgtgttgtg    1951
tatgtacata atgaagtagt tttttaaaa aaaagtcaat taaaagggta gaacagtttc     2011
cttcgataag ttgccagatg ctaccaaatt gcttgtgatt gttccctgcc cgttcatgat    2071
attgttatta cagaatttgt gagagaggaa acttctggga tttttctgaa aaaaaaaaa    2131
```

<210> SEQ ID NO 13
<211> LENGTH: 430
<212> TYPE: PRT
<213> ORGANISM: Zea mays

<400> SEQUENCE: 13

```
Met Gln Ser Gly Gly Asp Met Arg Pro Val His Asn Ser Val Asp Thr
1               5                   10                  15

Val Asn Ala Ala Ala Val Ala Ile Val Thr Ala Glu Ser Arg Thr Gln
            20                  25                  30

Pro Pro Ala Glu Gln Arg Arg Lys Trp Ala Asp Arg Leu Ser Val Tyr
        35                  40                  45

Phe Cys Phe Gly Ser Gln Lys Asn Gly Arg Arg Met Arg Val Asn His
    50                  55                  60

Ala Ala Leu Val Pro Glu Pro Ala Pro Gln Arg Thr Asp Ala Pro Ala
65                  70                  75                  80

Ala Glu Ile Pro Asn His Pro Pro Pro Val Phe Pro Phe Val Ala
                85                  90                  95

Pro Pro Ser Ser Pro Ala Ser Phe Leu Gln Ser Glu Pro Thr Ser Ile
            100                 105                 110

Val Gln Ser Pro Arg Ala Gly Ala Pro Ala Phe Ser Pro Leu Ser Pro
        115                 120                 125

Asn Ser Gln Ser Pro Thr Gly Pro Pro Ser Ile Phe Ala Ile Gly Pro
    130                 135                 140

Tyr Ala His Glu Thr Gln Leu Val Ser Pro Val Phe Ser Ala Phe
145                 150                 155                 160

Thr Thr Glu Pro Ser Thr Ala Pro Phe Thr Pro Pro Glu Ser Val
                165                 170                 175

His Leu Thr Thr Pro Ser Ser Pro Glu Val Pro Tyr Ala Lys Leu Leu
            180                 185                 190

Thr Ser Ile Asn Asn Ser Lys Asn Gly Glu Ala Gly Asp Leu Gln
        195                 200                 205

Ser Tyr Pro Asn Tyr Pro Asp Ser Pro Ile Gly Arg Leu Ile Ser Pro
    210                 215                 220

Ser Ser Gly Cys Ser Gly Thr Ser Ser Pro Phe Pro Asp Pro Glu Met
225                 230                 235                 240

Gln Ala Ser Ser Arg Ser Ala Leu Arg Leu Phe Pro Val Arg Glu Pro
                245                 250                 255
```

-continued

```
Pro Lys Ile Leu Asp Gly Glu Gly Val Ala Thr Gln Lys Leu Ile Pro
            260                 265                 270

Arg His Met Arg Asn Gly Gly Ser Leu Leu Asp Gly Gln Ile Ser Ala
        275                 280                 285

Ala Val Pro Val Val Asp Phe Ser Ala Arg Leu Gln Pro Asn Glu His
    290                 295                 300

Ala Met Asp His Arg Val Ser Phe Glu Leu Thr Val Glu Asp Val Ala
305                 310                 315                 320

Arg Cys Leu Glu Lys Lys Thr Ala Ile Ser Gly Asp Ser Gly Thr Ala
                325                 330                 335

Ser Phe His Leu Ala Pro Thr Gly Ser Gly Asp His His Arg Glu Ser
            340                 345                 350

Asn Glu Ala Arg Ala Gly Leu Tyr Val Asp Glu Ser Tyr His Asp Leu
        355                 360                 365

Pro Glu Lys Ala Arg Arg Ser Leu Ser Leu Arg Leu Ala Lys Glu Phe
    370                 375                 380

Asn Phe Asn Asn Val Asp Val Gly Ser Val Glu Pro Ser Val Gly Ser
385                 390                 395                 400

Asp Trp Trp Ala Asn Glu Lys Val Ala Gly Met Thr Thr Glu Pro Lys
                405                 410                 415

Lys Asn Trp Ser Phe His Pro Val Val Gln Pro Gly Val Ser
            420                 425                 430

<210> SEQ ID NO 14
<211> LENGTH: 1029
<212> TYPE: DNA
<213> ORGANISM: Raphanus sativus
<220> FEATURE:
<221> NAME/KEY: CDS
<222> LOCATION: (1)..(1029)

<400> SEQUENCE: 14 atg aga ggc ggc gcg agt gga aac aac gtt ttg gag act ata aac gca      48
Met Arg Gly Gly Ala Ser Gly Asn Asn Val Leu Glu Thr Ile Asn Ala
1               5                   10                  15 gcc gct act gcg ttc gct tcc tct gat gat cgt gtt cat cac caa cct      96
Ala Ala Thr Ala Phe Ala Ser Ser Asp Asp Arg Val His His Gln Pro
            20                  25                  30 tcc ccg att cat aga aga aaa cga atc ggg aaa gct gct ctt gct cct     144
Ser Pro Ile His Arg Arg Lys Arg Ile Gly Lys Ala Ala Leu Ala Pro
        35                  40                  45 gaa ccg gtt cct acc gat tcc aca tcc aat tcc ggt tat cgt tcg gtt     192
Glu Pro Val Pro Thr Asp Ser Thr Ser Asn Ser Gly Tyr Arg Ser Val
    50                  55                  60 atg acg gct ctt cct ttc ata gcc cca cct tcc tct cca gct tcc ttc     240
Met Thr Ala Leu Pro Phe Ile Ala Pro Pro Ser Ser Pro Ala Ser Phe
65                  70                  75                  80 ttc caa tca gaa cct cct tcc gct aca cag tca cct gta ggg atc ctc     288
Phe Gln Ser Glu Pro Pro Ser Ala Thr Gln Ser Pro Val Gly Ile Leu
                85                  90                  95 tcc ttt agt cct cta cct tct aac agc cac aac aac aac aac aac agc     336
Ser Phe Ser Pro Leu Pro Ser Asn Ser His Asn Asn Asn Asn Asn Ser
            100                 105                 110 gaa gaa cgt cct tcg atc ttc gcc atc gga cct tac gct cac gaa cct     384
Glu Glu Arg Pro Ser Ile Phe Ala Ile Gly Pro Tyr Ala His Glu Pro
        115                 120                 125 cag ctg gtt tct cct ccg gtt ttc tct act tac aca acc gaa ccg tct     432
Gln Leu Val Ser Pro Pro Val Phe Ser Thr Tyr Thr Thr Glu Pro Ser
    130                 135                 140
```

| | |
|---|---|
| tca gct ccg gtc acg ccg cct ctc gac gag tct ttc tac tta acc acc<br>Ser Ala Pro Val Thr Pro Pro Leu Asp Glu Ser Phe Tyr Leu Thr Thr<br>145                    150                    155                    160 | 480 |
| acc aca ccg tct tcg cct gaa gtc cct ttc gct cag ctc ttt aac tcc<br>Thr Thr Pro Ser Ser Pro Glu Val Pro Phe Ala Gln Leu Phe Asn Ser<br>                  165                    170                    175 | 528 |
| agc agt aac tac ggt gtc agg tct ccg gtg tct aac tac gag ttt cag<br>Ser Ser Asn Tyr Gly Val Arg Ser Pro Val Ser Asn Tyr Glu Phe Gln<br>        180                    185                    190 | 576 |
| ttt tac caa ctt cct ccc ggt agt cca ctc gct cag ctt atc tcc ccc<br>Phe Tyr Gln Leu Pro Pro Gly Ser Pro Leu Ala Gln Leu Ile Ser Pro<br>            195                    200                    205 | 624 |
| agc tcg gtt atg tcc ggt tct ggt gcg act tct ccg ttt cct gac gga<br>Ser Ser Val Met Ser Gly Ser Gly Ala Thr Ser Pro Phe Pro Asp Gly<br>        210                    215                    220 | 672 |
| ctc gct cag ttt caa gtc tct gat cca cca aag ctg ctg agc cct ggt<br>Leu Ala Gln Phe Gln Val Ser Asp Pro Pro Lys Leu Leu Ser Pro Gly<br>225                    230                    235                    240 | 720 |
| aaa ctg cgt tgc tcc aag tct gtt aca act cct aaa gag cag aac aag<br>Lys Leu Arg Cys Ser Lys Ser Val Thr Thr Pro Lys Glu Gln Asn Lys<br>                  245                    250                    255 | 768 |
| att gtg aga ccg aac aaa ccg gtt tcg ttc gat ctt gat gcg gat cat<br>Ile Val Arg Pro Asn Lys Pro Val Ser Phe Asp Leu Asp Ala Asp His<br>        260                    265                    270 | 816 |
| ttc att aga tgc gtt gat aag aag ctg aga aca acg ttc cct gaa gcg<br>Phe Ile Arg Cys Val Asp Lys Lys Leu Arg Thr Thr Phe Pro Glu Ala<br>            275                    280                    285 | 864 |
| tct gat caa gaa gca gct caa cat tcc tcc tcc gga tcc aat aaa gaa<br>Ser Asp Gln Glu Ala Ala Gln His Ser Ser Ser Gly Ser Asn Lys Glu<br>290                    295                    300 | 912 |
| ttc gat ttc ggc acc acc gat gag ata cat ttg acc ggt gat gat gag<br>Phe Asp Phe Gly Thr Thr Asp Glu Ile His Leu Thr Gly Asp Asp Glu<br>305                    310                    315                    320 | 960 |
| cat aga gat tcg acc aag aac agc agc gat tgg tcc ttc cct gtg atg<br>His Arg Asp Ser Thr Lys Asn Ser Ser Asp Trp Ser Phe Pro Val Met<br>                  325                    330                    335 | 1008 |
| caa tca ggc aca ctt agc taa<br>Gln Ser Gly Thr Leu Ser<br>        340 | 1029 |

```
<210> SEQ ID NO 15
<211> LENGTH: 342
<212> TYPE: PRT
<213> ORGANISM: Raphanus sativus

<400> SEQUENCE: 15
```

Met Arg Gly Gly Ala Ser Gly Asn Asn Val Leu Glu Thr Ile Asn Ala
1                 5                      10                    15

Ala Ala Thr Ala Phe Ala Ser Ser Asp Asp Arg Val His His Gln Pro
                20                    25                    30

Ser Pro Ile His Arg Arg Lys Arg Ile Gly Lys Ala Ala Leu Ala Pro
        35                    40                    45

Glu Pro Val Pro Thr Asp Ser Thr Ser Asn Ser Gly Tyr Arg Ser Val
50                    55                    60

Met Thr Ala Leu Pro Phe Ile Ala Pro Pro Ser Ser Pro Ala Ser Phe
65                 70                    75                    80

Phe Gln Ser Glu Pro Pro Ser Ala Thr Gln Ser Pro Val Gly Ile Leu
                85                    90                    95

```
Ser Phe Ser Pro Leu Pro Ser Asn Ser His Asn Asn Asn Asn Ser
            100                 105                 110

Glu Glu Arg Pro Ser Ile Phe Ala Ile Gly Pro Tyr Ala His Glu Pro
        115                 120                 125

Gln Leu Val Ser Pro Pro Val Phe Ser Thr Tyr Thr Thr Glu Pro Ser
    130                 135                 140

Ser Ala Pro Val Thr Pro Pro Leu Asp Glu Ser Phe Tyr Leu Thr Thr
145                 150                 155                 160

Thr Thr Pro Ser Ser Pro Glu Val Pro Phe Ala Gln Leu Phe Asn Ser
                165                 170                 175

Ser Ser Asn Tyr Gly Val Arg Ser Pro Val Ser Asn Tyr Glu Phe Gln
            180                 185                 190

Phe Tyr Gln Leu Pro Pro Gly Ser Pro Leu Ala Gln Leu Ile Ser Pro
        195                 200                 205

Ser Ser Val Met Ser Gly Ser Gly Ala Thr Ser Pro Phe Pro Asp Gly
    210                 215                 220

Leu Ala Gln Phe Gln Val Ser Asp Pro Lys Leu Leu Ser Pro Gly
225                 230                 235                 240

Lys Leu Arg Cys Ser Lys Ser Val Thr Thr Pro Lys Glu Gln Asn Lys
                245                 250                 255

Ile Val Arg Pro Asn Lys Pro Val Ser Phe Asp Leu Asp Ala Asp His
            260                 265                 270

Phe Ile Arg Cys Val Asp Lys Lys Leu Arg Thr Thr Phe Pro Glu Ala
        275                 280                 285

Ser Asp Gln Glu Ala Ala Gln His Ser Ser Gly Ser Asn Lys Glu
    290                 295                 300

Phe Asp Phe Gly Thr Thr Asp Glu Ile His Leu Thr Gly Asp Glu
305                 310                 315                 320

His Arg Asp Ser Thr Lys Asn Ser Ser Asp Trp Ser Phe Pro Val Met
                325                 330                 335

Gln Ser Gly Thr Leu Ser
            340

<210> SEQ ID NO 16
<211> LENGTH: 2350
<212> TYPE: DNA
<213> ORGANISM: Populus trichocarpa
<220> FEATURE:
<221> NAME/KEY: CDS
<222> LOCATION: (298)..(1821)

<400> SEQUENCE: 16
ggaaaagagt taatgggatt aaaaacaaca acaagagga taagaaccgt agagaagaga      60
gagtgtgcat gttttcgtt tcatgatct gaaaaacag aacacaactc aacacttctc      120
ttctgttctg ttctgctgtc ttgtttttttt tttgttttt tttttaaaca aaaatctctt    180
cttttttcac ttctttatc taagaaaaca gcagccctct ttggttttgg tatgaattta    240
attccctgca tgtgttttat gggtggtgat gtttgctgtt gttgttgtta atcaaag       297 atg aga agt gtc aat aat agc agc atc gaa acc gtt aac gcc gct gct     345
Met Arg Ser Val Asn Asn Ser Ser Ile Glu Thr Val Asn Ala Ala Ala
1               5                   10                  15 acc gcc atc gtc tcc gcc gag tct cgt gtc cag cca tcc tct tct tct     393
Thr Ala Ile Val Ser Ala Glu Ser Arg Val Gln Pro Ser Ser Ser Ser
            20                  25                  30 gtt caa aaa aga agg tgg gga ggc tgc tgg agt ctc tac tgg tgt ttt     441
Val Gln Lys Arg Arg Trp Gly Gly Cys Trp Ser Leu Tyr Trp Cys Phe
```

-continued

|  |  |  |  |  |  |  |  |  |  |  |  |  |  |  |  |
|---|---|---|---|---|---|---|---|---|---|---|---|---|---|---|---|

```
                    35                    40                    45
ggt tct cac ggt tct cac aag aat agc aag cga att ggt cat gct gtc    489
Gly Ser His Gly Ser His Lys Asn Ser Lys Arg Ile Gly His Ala Val
         50                  55                  60 ctt gtt cct gaa cca gaa gta cca gga gca gta tcc tct tca act gaa    537
Leu Val Pro Glu Pro Glu Val Pro Gly Ala Val Ser Ser Ser Thr Glu
 65                  70                  75                  80 aat cag act cag tca act ccc att ctg ctg ccc ttt att gct cct ccc    585
Asn Gln Thr Gln Ser Thr Pro Ile Leu Leu Pro Phe Ile Ala Pro Pro
                 85                  90                  95 tct tct cct gct tct ttc ctc cag tct gat ccc cct tcc tcc act caa    633
Ser Ser Pro Ala Ser Phe Leu Gln Ser Asp Pro Pro Ser Ser Thr Gln
             100                 105                 110 tca cca gca gga ttg ctc tct ctc acg tcc ctc tcg gcg aat gct tat    681
Ser Pro Ala Gly Leu Leu Ser Leu Thr Ser Leu Ser Ala Asn Ala Tyr
         115                 120                 125 tcc cca cgc gga cct gca tcc att ttt gcc ata ggc cct tat gca cat    729
Ser Pro Arg Gly Pro Ala Ser Ile Phe Ala Ile Gly Pro Tyr Ala His
     130                 135                 140 gaa acc cag cta gtc aca cca cct gtg ttt tct gct ttc acc act gag    777
Glu Thr Gln Leu Val Thr Pro Pro Val Phe Ser Ala Phe Thr Thr Glu
145                 150                 155                 160 cca tcc act gct cca ttc act ccc cct ccg gag tct gtt caa ctt act    825
Pro Ser Thr Ala Pro Phe Thr Pro Pro Pro Glu Ser Val Gln Leu Thr
                165                 170                 175 aca cct tca tct cct gaa gtg cca ttt gct caa ctc ttg acg tcc tct    873
Thr Pro Ser Ser Pro Glu Val Pro Phe Ala Gln Leu Leu Thr Ser Ser
            180                 185                 190 ctg gaa cgt gct cga aga aat agt ggc ccc aat caa aag ttt tcg tta    921
Leu Glu Arg Ala Arg Arg Asn Ser Gly Pro Asn Gln Lys Phe Ser Leu
        195                 200                 205 tct cac tat gaa ttt cag tca tat cat ctg tac cca gga agc cca ggt    969
Ser His Tyr Glu Phe Gln Ser Tyr His Leu Tyr Pro Gly Ser Pro Gly
    210                 215                 220 ggt caa atc atc tca cca gga tca gca atc tcg aat tca ggt acc tct    1017
Gly Gln Ile Ile Ser Pro Gly Ser Ala Ile Ser Asn Ser Gly Thr Ser
225                 230                 235                 240 tct ccg ttc ccc gat aga cat cct atg ctt gag ttc cga atg ggt gag    1065
Ser Pro Phe Pro Asp Arg His Pro Met Leu Glu Phe Arg Met Gly Glu
                245                 250                 255 gct ccc aag ctc ctg ggc ttc gaa cat ttt agt act cgt aaa tgg ggt    1113
Ala Pro Lys Leu Leu Gly Phe Glu His Phe Ser Thr Arg Lys Trp Gly
            260                 265                 270 tca aga ttg ggt tct gga tct ttg aca ccg gat gcg act cca gat ggc    1161
Ser Arg Leu Gly Ser Gly Ser Leu Thr Pro Asp Ala Thr Pro Asp Gly
        275                 280                 285 atg gga tta tcc agg ctc ggt tcc ggt acg gtg acc cca gat ggc atg    1209
Met Gly Leu Ser Arg Leu Gly Ser Gly Thr Val Thr Pro Asp Gly Met
    290                 295                 300 ggg cta tcg agg ctc tgt tct gga act gcc act cca gat ggt gcg ggc    1257
Gly Leu Ser Arg Leu Cys Ser Gly Thr Ala Thr Pro Asp Gly Ala Gly
305                 310                 315                 320 ctg cgt tca agg ctt ggc tca gga act ttg acc cct gat tgc ttc gtg    1305
Leu Arg Ser Arg Leu Gly Ser Gly Thr Leu Thr Pro Asp Cys Phe Val
                325                 330                 335 cct gcc tcg caa att ggt ttc ctt ttg gag aac caa att tct gag gtt    1353
Pro Ala Ser Gln Ile Gly Phe Leu Leu Glu Asn Gln Ile Ser Glu Val
            340                 345                 350 gca tca ctt acc aac tca gaa aat gga tca aaa acc gaa gaa aat gtg    1401
```

```
                Ala Ser Leu Thr Asn Ser Glu Asn Gly Ser Lys Thr Glu Asn Val
                            355                 360                 365 gtt cac cac aga gtc tcc ttt gag ttg agc ggt gaa gag gtt gcg cgt           1449
Val His His Arg Val Ser Phe Glu Leu Ser Gly Glu Glu Val Ala Arg
    370                 375                 380 tgt ctt gaa att aag tca gtg gca tcc act aga act ttc cca gag tat           1497
Cys Leu Glu Ile Lys Ser Val Ala Ser Thr Arg Thr Phe Pro Glu Tyr
385                 390                 395                 400 cca cag gac acc atg ccc gaa gac cca gtg aga ggt gat agg tta gca           1545
Pro Gln Asp Thr Met Pro Glu Asp Pro Val Arg Gly Asp Arg Leu Ala
                405                 410                 415 atg aat ggt gaa cgt tgc tta caa aac ggg gaa gct tcc agt gaa atg           1593
Met Asn Gly Glu Arg Cys Leu Gln Asn Gly Glu Ala Ser Ser Glu Met
            420                 425                 430 cct gag aaa aat tca gaa gaa aca gaa gag gat cac gtc tat aga aag           1641
Pro Glu Lys Asn Ser Glu Glu Thr Glu Glu Asp His Val Tyr Arg Lys
        435                 440                 445 cat cga tcc atc act ctt ggg tca ata aaa gag ttt aac ttt gat aac           1689
His Arg Ser Ile Thr Leu Gly Ser Ile Lys Glu Phe Asn Phe Asp Asn
    450                 455                 460 tct aaa gga gaa gtc tct gat aag cct gct atc agc tct gag tgg tgg           1737
Ser Lys Gly Glu Val Ser Asp Lys Pro Ala Ile Ser Ser Glu Trp Trp
465                 470                 475                 480 gca aat gaa acg att gct ggg aag gaa gct aga cct gcc aac agc tgg           1785
Ala Asn Glu Thr Ile Ala Gly Lys Glu Ala Arg Pro Ala Asn Ser Trp
                485                 490                 495 act ttc ttt cct ctg cta cag cca gag gtc agc tga cattacaatc                1831
Thr Phe Phe Pro Leu Leu Gln Pro Glu Val Ser
            500                 505 atgaaaaaaa gacctctctt ccatatttgg acagtgaagc aaatatgttg tattgaaagc         1891
tagcctgtga gatgcaagtc caaagccagc actgttttgg aaactctgat taccatagtc         1951
tgcaatcaca tgattgaagg atagatttca cagtactatt ttctcaagtg accaaaagca         2011
caaattctta gaggaagtag tttgtaggga tccttggtgt gggcactgat agatcattct         2071 ttttttatc ttttccttat tttagttaca caaaaatagc atttgcatat aggtattgta          2131
ctctggatat ttttttcttt tccttttcc ttttcatgtg taataataag agaatttggt          2191
ttccttcgac aggtgccctc actatagtga ttcggtgtct ctgtggctgt atatgcccct         2251
cctcgtcttg tttctgcagg ttctctcgtt atagaatcct gatgaattga ttatatatat         2311
tagaaagata agtttgatat tgatctatct acatttttta                               2350

<210> SEQ ID NO 17
<211> LENGTH: 507
<212> TYPE: PRT
<213> ORGANISM: Populus trichocarpa

<400> SEQUENCE: 17

Met Arg Ser Val Asn Asn Ser Ser Ile Glu Thr Val Asn Ala Ala Ala
1               5                   10                  15

Thr Ala Ile Val Ser Ala Glu Ser Arg Val Gln Pro Ser Ser Ser Ser
            20                  25                  30

Val Gln Lys Arg Trp Gly Gly Cys Trp Ser Leu Tyr Trp Cys Phe
        35                  40                  45

Gly Ser His Gly Ser His Lys Asn Ser Lys Arg Ile Gly His Ala Val
    50                  55                  60

Leu Val Pro Glu Pro Glu Val Pro Gly Ala Val Ser Ser Ser Thr Glu
65                  70                  75                  80
```

-continued

```
Asn Gln Thr Gln Ser Thr Pro Ile Leu Leu Pro Phe Ile Ala Pro Pro
                85                  90                  95

Ser Ser Pro Ala Ser Phe Leu Gln Ser Asp Pro Pro Ser Ser Thr Gln
            100                 105                 110

Ser Pro Ala Gly Leu Leu Ser Leu Thr Ser Leu Ser Ala Asn Ala Tyr
        115                 120                 125

Ser Pro Arg Gly Pro Ala Ser Ile Phe Ala Ile Gly Pro Tyr Ala His
    130                 135                 140

Glu Thr Gln Leu Val Thr Pro Pro Val Phe Ser Ala Phe Thr Thr Glu
145                 150                 155                 160

Pro Ser Thr Ala Pro Phe Thr Pro Pro Glu Ser Val Gln Leu Thr
                165                 170                 175

Thr Pro Ser Ser Pro Glu Val Pro Phe Ala Gln Leu Leu Thr Ser Ser
                180                 185                 190

Leu Glu Arg Ala Arg Arg Asn Ser Gly Pro Asn Gln Lys Phe Ser Leu
            195                 200                 205

Ser His Tyr Glu Phe Gln Ser Tyr His Leu Tyr Pro Gly Ser Pro Gly
        210                 215                 220

Gly Gln Ile Ile Ser Pro Gly Ser Ala Ile Ser Asn Ser Gly Thr Ser
225                 230                 235                 240

Ser Pro Phe Pro Asp Arg His Pro Met Leu Glu Phe Arg Met Gly Glu
                245                 250                 255

Ala Pro Lys Leu Leu Gly Phe Glu His Phe Ser Thr Arg Lys Trp Gly
                260                 265                 270

Ser Arg Leu Gly Ser Gly Ser Leu Thr Pro Asp Ala Thr Pro Asp Gly
            275                 280                 285

Met Gly Leu Ser Arg Leu Gly Ser Gly Thr Val Thr Pro Asp Gly Met
        290                 295                 300

Gly Leu Ser Arg Leu Cys Ser Gly Thr Ala Thr Pro Asp Gly Ala Gly
305                 310                 315                 320

Leu Arg Ser Arg Leu Gly Ser Gly Thr Leu Thr Pro Asp Cys Phe Val
                325                 330                 335

Pro Ala Ser Gln Ile Gly Phe Leu Leu Glu Asn Gln Ile Ser Glu Val
                340                 345                 350

Ala Ser Leu Thr Asn Ser Glu Asn Gly Ser Lys Thr Glu Glu Asn Val
            355                 360                 365

Val His His Arg Val Ser Phe Glu Leu Ser Gly Glu Glu Val Ala Arg
        370                 375                 380

Cys Leu Glu Ile Lys Ser Val Ala Ser Thr Arg Thr Phe Pro Glu Tyr
385                 390                 395                 400

Pro Gln Asp Thr Met Pro Glu Asp Pro Val Arg Gly Asp Arg Leu Ala
                405                 410                 415

Met Asn Gly Glu Arg Cys Leu Gln Asn Gly Glu Ala Ser Ser Glu Met
            420                 425                 430

Pro Glu Lys Asn Ser Glu Glu Thr Glu Glu Asp His Val Tyr Arg Lys
        435                 440                 445

His Arg Ser Ile Thr Leu Gly Ser Ile Lys Glu Phe Asn Phe Asp Asn
    450                 455                 460

Ser Lys Gly Glu Val Ser Asp Lys Pro Ala Ile Ser Ser Glu Trp Trp
465                 470                 475                 480

Ala Asn Glu Thr Ile Ala Gly Lys Glu Ala Arg Pro Ala Asn Ser Trp
                485                 490                 495
```

```
Thr Phe Phe Pro Leu Leu Gln Pro Glu Val Ser
        500                 505
```

<210> SEQ ID NO 18
<211> LENGTH: 1523
<212> TYPE: DNA
<213> ORGANISM: Vitis vinifera
<220> FEATURE:
<221> NAME/KEY: CDS
<222> LOCATION: (177)..(1523)

<400> SEQUENCE: 18

```
gaatctcgtg tgattttcgt tttcccgatc ggactcacag ctccatatcg gaatctcgcc    60
ggaaaacttg ctgtttctta tggtgaattt taagcacaca tagccggaat tagaagtttt   120
agttgtcgga ggaggtttga gttggaaata gggggatttt gtgatttata aggaag atg   179
                                                               Met
                                                                 1 aga agt gtg aat aat agc gta gag act ata aac gcc gcg gcc act gcg    227
Arg Ser Val Asn Asn Ser Val Glu Thr Ile Asn Ala Ala Ala Thr Ala
          5                  10                  15 atc gtc tcg gcc gag agt cga gtc cag ccg act acg gtt cag aag aga    275
Ile Val Ser Ala Glu Ser Arg Val Gln Pro Thr Thr Val Gln Lys Arg
     20                  25                  30 aga tgg ggt agc tgc ttg agt tta tac tgg tgc ttt gga tct cat aga    323
Arg Trp Gly Ser Cys Leu Ser Leu Tyr Trp Cys Phe Gly Ser His Arg
 35                  40                  45 cac agc aag cga ata ggt cat gct gtt ctt gtt cct gaa cca atg gtg    371
His Ser Lys Arg Ile Gly His Ala Val Leu Val Pro Glu Pro Met Val
 50                  55                  60                  65 cca gga gct gtc gct cct gct tct gaa aac ctg aac ctc tca acc agc    419
Pro Gly Ala Val Ala Pro Ala Ser Glu Asn Leu Asn Leu Ser Thr Ser
                 70                  75                  80 att gta ctg cct ttc att gca cct ccc tct tct cct gca tct ttc ctc    467
Ile Val Leu Pro Phe Ile Ala Pro Pro Ser Ser Pro Ala Ser Phe Leu
             85                  90                  95 caa tca gat cct ccg tcc tcc act cag tca cca gct gga ttt cta tcc    515
Gln Ser Asp Pro Pro Ser Ser Thr Gln Ser Pro Ala Gly Phe Leu Ser
        100                 105                 110 ctc act gcc ctt tct gtc aat gcc tat tcc cca agt ggt cct gcc tcc    563
Leu Thr Ala Leu Ser Val Asn Ala Tyr Ser Pro Ser Gly Pro Ala Ser
    115                 120                 125 atg ttt gcc att ggc cct tat gcc cat gaa act caa cta gtc tca cca    611
Met Phe Ala Ile Gly Pro Tyr Ala His Glu Thr Gln Leu Val Ser Pro
130                 135                 140                 145 cct gta ttt tct acc ttc ccc aca gag cca tcg act gct cct ttt act    659
Pro Val Phe Ser Thr Phe Pro Thr Glu Pro Ser Thr Ala Pro Phe Thr
                150                 155                 160 ccc cct cca gaa tct gtg caa tta act acg cct tca tca cct gaa gtt    707
Pro Pro Pro Glu Ser Val Gln Leu Thr Thr Pro Ser Ser Pro Glu Val
            165                 170                 175 cca ttt gct cag ctg ctg aca tct tca ctg gac cgc tct cga agg aac    755
Pro Phe Ala Gln Leu Leu Thr Ser Ser Leu Asp Arg Ser Arg Arg Asn
        180                 185                 190 agt gga acc aat cag aag ttg tca ctg tcc aat tat gaa ttc cag cct    803
Ser Gly Thr Asn Gln Lys Leu Ser Leu Ser Asn Tyr Glu Phe Gln Pro
    195                 200                 205 tat cag cta tac cca gaa agc cca gtt ggc cac ctt ata tca cca ata    851
Tyr Gln Leu Tyr Pro Glu Ser Pro Val Gly His Leu Ile Ser Pro Ile
210                 215                 220                 225 tca aat tct ggt acc tct tct cct ttc cca gat aga cgc cca att gta    899
```

```
Ser Asn Ser Gly Thr Ser Ser Pro Phe Pro Asp Arg Arg Pro Ile Val
            230                 235                 240 gag gct ccc aag ctc ttg ggt ttt gaa cat ttt tcc acc cgc aga tgg     947
Glu Ala Pro Lys Leu Leu Gly Phe Glu His Phe Ser Thr Arg Arg Trp
            245                 250                 255 ggt tca agg ctg ggt tct gga tct ttg aca cca gat ggt gca ggg cct     995
Gly Ser Arg Leu Gly Ser Gly Ser Leu Thr Pro Asp Gly Ala Gly Pro
        260                 265                 270 gcc tcc cga gac agt ttc ctt ctg gag aac cag atc tct gag gtg gca    1043
Ala Ser Arg Asp Ser Phe Leu Leu Glu Asn Gln Ile Ser Glu Val Ala
    275                 280                 285 tcc ctt gcc aac tct gag agt gga tct caa aat ggt gaa act gta atc    1091
Ser Leu Ala Asn Ser Glu Ser Gly Ser Gln Asn Gly Glu Thr Val Ile
290                 295                 300                 305 gat cat agg gtc tca ttt gag ttg gct ggt gaa gat gtt gca gtt tgt    1139
Asp His Arg Val Ser Phe Glu Leu Ala Gly Glu Asp Val Ala Val Cys
            310                 315                 320 gtt gaa aag aaa cca gtg gca tca gct gaa acc gtc caa aac act ctt    1187
Val Glu Lys Lys Pro Val Ala Ser Ala Glu Thr Val Gln Asn Thr Leu
            325                 330                 335 cag gat ata gtt gaa gaa ggc gaa att gaa aga gaa aga gat ggg att    1235
Gln Asp Ile Val Glu Glu Gly Glu Ile Glu Arg Glu Arg Asp Gly Ile
        340                 345                 350 tca gag agt aca gaa aat tgt tgt gag ttc tgt gtc gga gaa gct ctt    1283
Ser Glu Ser Thr Glu Asn Cys Cys Glu Phe Cys Val Gly Glu Ala Leu
    355                 360                 365 aaa gct gcg tcc gag aaa gct tca gct gaa gga gag gaa gag cag tgc    1331
Lys Ala Ala Ser Glu Lys Ala Ser Ala Glu Gly Glu Glu Glu Gln Cys
370                 375                 380                 385 cat aaa aag cat cct ccg atc aga cat ggt tca atc aaa gag ttc aat    1379
His Lys Lys His Pro Pro Ile Arg His Gly Ser Ile Lys Glu Phe Asn
            390                 395                 400 ttt gac aac aca aag gga gaa gtc tca gcc aag ccg aac atc atc ggt    1427
Phe Asp Asn Thr Lys Gly Glu Val Ser Ala Lys Pro Asn Ile Ile Gly
            405                 410                 415 tct gag tgg tgg gta aac gaa aag gtt gtc ggg aaa gga aca ggg ccc    1475
Ser Glu Trp Trp Val Asn Glu Lys Val Val Gly Lys Gly Thr Gly Pro
        420                 425                 430 caa acc aac tgg act ttc ttc cca ttg ctg cag ccc gga atc agt tga    1523
Gln Thr Asn Trp Thr Phe Phe Pro Leu Leu Gln Pro Gly Ile Ser
    435                 440                 445

<210> SEQ ID NO 19
<211> LENGTH: 448
<212> TYPE: PRT
<213> ORGANISM: Vitis vinifera

<400> SEQUENCE: 19

Met Arg Ser Val Asn Asn Ser Val Glu Thr Ile Asn Ala Ala Thr
1               5                   10                  15

Ala Ile Val Ser Ala Glu Ser Arg Val Gln Pro Thr Thr Val Gln Lys
            20                  25                  30

Arg Arg Trp Gly Ser Cys Leu Ser Leu Tyr Trp Cys Phe Gly Ser His
        35                  40                  45

Arg His Ser Lys Arg Ile Gly His Ala Val Leu Val Pro Glu Pro Met
    50                  55                  60

Val Pro Gly Ala Val Ala Pro Ala Ser Glu Asn Leu Asn Leu Ser Thr
65                  70                  75                  80

Ser Ile Val Leu Pro Phe Ile Ala Pro Pro Ser Ser Pro Ala Ser Phe
```

```
                    85                  90                  95
Leu Gln Ser Asp Pro Ser Thr Gln Ser Pro Ala Gly Phe Leu
                100                 105                 110

Ser Leu Thr Ala Leu Ser Val Asn Ala Tyr Ser Pro Ser Gly Pro Ala
                115                 120                 125

Ser Met Phe Ala Ile Gly Pro Tyr Ala His Glu Thr Gln Leu Val Ser
        130                 135                 140

Pro Pro Val Phe Ser Thr Phe Pro Thr Glu Pro Ser Thr Ala Pro Phe
145                 150                 155                 160

Thr Pro Pro Pro Glu Ser Val Gln Leu Thr Thr Pro Ser Ser Pro Glu
                165                 170                 175

Val Pro Phe Ala Gln Leu Leu Thr Ser Ser Leu Asp Arg Ser Arg Arg
                180                 185                 190

Asn Ser Gly Thr Asn Gln Lys Leu Ser Leu Ser Asn Tyr Glu Phe Gln
                195                 200                 205

Pro Tyr Gln Leu Tyr Pro Glu Ser Pro Val Gly His Leu Ile Ser Pro
        210                 215                 220

Ile Ser Asn Ser Gly Thr Ser Ser Pro Phe Pro Asp Arg Arg Pro Ile
225                 230                 235                 240

Val Glu Ala Pro Lys Leu Leu Gly Phe Glu His Phe Ser Thr Arg Arg
                245                 250                 255

Trp Gly Ser Arg Leu Gly Ser Gly Ser Leu Thr Pro Asp Gly Ala Gly
                260                 265                 270

Pro Ala Ser Arg Asp Ser Phe Leu Leu Glu Asn Gln Ile Ser Glu Val
                275                 280                 285

Ala Ser Leu Ala Asn Ser Glu Ser Gly Ser Gln Asn Gly Glu Thr Val
        290                 295                 300

Ile Asp His Arg Val Ser Phe Glu Leu Ala Gly Glu Asp Val Ala Val
305                 310                 315                 320

Cys Val Glu Lys Lys Pro Val Ala Ser Ala Glu Thr Val Gln Asn Thr
                325                 330                 335

Leu Gln Asp Ile Val Glu Glu Gly Glu Ile Glu Arg Glu Arg Asp Gly
                340                 345                 350

Ile Ser Glu Ser Thr Glu Asn Cys Glu Phe Cys Val Gly Glu Ala
        355                 360                 365

Leu Lys Ala Ala Ser Glu Lys Ala Ser Ala Glu Gly Glu Glu Gln
        370                 375                 380

Cys His Lys Lys His Pro Pro Ile Arg His Gly Ser Ile Lys Glu Phe
385                 390                 395                 400

Asn Phe Asp Asn Thr Lys Gly Glu Val Ser Ala Lys Pro Asn Ile Ile
                405                 410                 415

Gly Ser Glu Trp Trp Val Asn Glu Lys Val Val Gly Lys Gly Thr Gly
                420                 425                 430

Pro Gln Thr Asn Trp Thr Phe Phe Pro Leu Leu Gln Pro Gly Ile Ser
                435                 440                 445

<210> SEQ ID NO 20
<211> LENGTH: 4092
<212> TYPE: DNA
<213> ORGANISM: Physcomitrella patens
<220> FEATURE:
<221> NAME/KEY: CDS
<222> LOCATION: (1)..(4092)

<400> SEQUENCE: 20
```

-continued

| | |
|---|---|
| atg gtg ctg ctc atg aat agg aat gca ctc ggt atc cat ttc ggt gcc<br>Met Val Leu Leu Met Asn Arg Asn Ala Leu Gly Ile His Phe Gly Ala<br>1               5                   10                  15 | 48 |
| cgg gcc agt ctg gca gtg atg gtg atc cat tgg tat ttg cgg cct ggc<br>Arg Ala Ser Leu Ala Val Met Val Ile His Trp Tyr Leu Arg Pro Gly<br>            20                  25                  30 | 96 |
| gag cta acc cca tgc tca ccc acg aat ggc cca tta tgg aaa tgg atg<br>Glu Leu Thr Pro Cys Ser Pro Thr Asn Gly Pro Leu Trp Lys Trp Met<br>        35                  40                  45 | 144 |
| aga aca atc tta cct ttt ccg gtg cct gta gat ttg aag agg gag gct<br>Arg Thr Ile Leu Pro Phe Pro Val Pro Val Asp Leu Lys Arg Glu Ala<br>    50                  55                  60 | 192 |
| gtt ctg gcc gga acg gtc gtc gtc tac agc gtt cta aag atg ccc gtg<br>Val Leu Ala Gly Thr Val Val Val Tyr Ser Val Leu Lys Met Pro Val<br>65                  70                  75                  80 | 240 |
| ctc tgg agc tct tcc ctc gac gcc gac gcc gac gca gca gcc act aat<br>Leu Trp Ser Ser Ser Leu Asp Ala Asp Ala Asp Ala Ala Ala Thr Asn<br>                85                  90                  95 | 288 |
| cga cat tca tca tca acg ttc gtt aga gat ggt tgg agg gca tta acg<br>Arg His Ser Ser Ser Thr Phe Val Arg Asp Gly Trp Arg Ala Leu Thr<br>            100                 105                 110 | 336 |
| ggt cgt ggc caa gga ccg aaa ttg cgg cgg gtg gag ggt atg gag act<br>Gly Arg Gly Gln Gly Pro Lys Leu Arg Arg Val Glu Gly Met Glu Thr<br>        115                 120                 125 | 384 |
| agg gta gtt tct gca gag gag ctt gtt tta cca atg gtt gcc cta gct<br>Arg Val Val Ser Ala Glu Glu Leu Val Leu Pro Met Val Ala Leu Ala<br>    130                 135                 140 | 432 |
| tgg gta gtg gta cat aag ttc ctg tgg gcg cta tgg aag cta tgg cgc<br>Trp Val Val Val His Lys Phe Leu Trp Ala Leu Trp Lys Leu Trp Arg<br>145                 150                 155                 160 | 480 |
| tct gcc gtt gat gac ata aac att gga agg acg aaa cgt ttg tgt cct<br>Ser Ala Val Asp Asp Ile Asn Ile Gly Arg Thr Lys Arg Leu Cys Pro<br>                165                 170                 175 | 528 |
| acc tct tct cag atg gca cga ggt gga tgc tgc tgg agt ggg cca ttt<br>Thr Ser Ser Gln Met Ala Arg Gly Gly Cys Cys Trp Ser Gly Pro Phe<br>            180                 185                 190 | 576 |
| tgt ctt ggc tca tta tcc cgc aag aac aag aag cga att gtt ccg gca<br>Cys Leu Gly Ser Leu Ser Arg Lys Asn Lys Lys Arg Ile Val Pro Ala<br>        195                 200                 205 | 624 |
| acc aga gtg cac gat gga act gca cag cca tct gac cct cag ggc cag<br>Thr Arg Val His Asp Gly Thr Ala Gln Pro Ser Asp Pro Gln Gly Gln<br>    210                 215                 220 | 672 |
| ttt gcc ttc cta ctt gca ccc cct tcg tct cct gct tcc tat gca aat<br>Phe Ala Phe Leu Leu Ala Pro Pro Ser Ser Pro Ala Ser Tyr Ala Asn<br>225                 230                 235                 240 | 720 |
| tct atg gca cct tcc tct gtt cag tcg ccc tac tac cct tca tcg tgt<br>Ser Met Ala Pro Ser Ser Val Gln Ser Pro Tyr Tyr Pro Ser Ser Cys<br>                245                 250                 255 | 768 |
| cct gtt cct cag ggt ggt ggg tct agg att cct cta gaa aca cag tct<br>Pro Val Pro Gln Gly Gly Gly Ser Arg Ile Pro Leu Glu Thr Gln Ser<br>            260                 265                 270 | 816 |
| aac atg ttc gct gta ggt ccg tat gca cat gaa acc gct cta gtc tct<br>Asn Met Phe Ala Val Gly Pro Tyr Ala His Glu Thr Ala Leu Val Ser<br>        275                 280                 285 | 864 |
| cca cca gtt ttt tct acg ttc aca act gct ccc tcc aca gct cct ttt<br>Pro Pro Val Phe Ser Thr Phe Thr Thr Ala Pro Ser Thr Ala Pro Phe<br>    290                 295                 300 | 912 |
| acg ccc cct cca gag ctt gca gcc cat ttc act acg cct tct tcc cct<br>Thr Pro Pro Pro Glu Leu Ala Ala His Phe Thr Thr Pro Ser Ser Pro<br>305                 310                 315                 320 | 960 |

```
gat gtt cct ttc gca aag ctg tta gga tct tcg ttc tca gaa cag cga   1008
Asp Val Pro Phe Ala Lys Leu Leu Gly Ser Ser Phe Ser Glu Gln Arg
            325                 330                 335 act acg aag cga gaa gcg gag cct cca tac tca gcc tct cca ttc gct   1056
Thr Thr Lys Arg Glu Ala Glu Pro Pro Tyr Ser Ala Ser Pro Phe Ala
        340                 345                 350 tcc cca gat tac tat cag caa gat cac cat ccg cag gat gac ttg cag   1104
Ser Pro Asp Tyr Tyr Gln Gln Asp His His Pro Gln Asp Asp Leu Gln
    355                 360                 365 gtt ggg tat cag tta tat cca gga agt ccg ctt ggt cgt tta att tct   1152
Val Gly Tyr Gln Leu Tyr Pro Gly Ser Pro Leu Gly Arg Leu Ile Ser
370                 375                 380 cct gca ggc acc acg ggc gcg tca act cct ttt gct gca ggt ggc act   1200
Pro Ala Gly Thr Thr Gly Ala Ser Thr Pro Phe Ala Ala Gly Gly Thr
385                 390                 395                 400 act ggt act aat act cct cat gca gag agt gac aat cct act cca ctg   1248
Thr Gly Thr Asn Thr Pro His Ala Glu Ser Asp Asn Pro Thr Pro Leu
                405                 410                 415 act gtc ctt cca gca gtg gta agc act tta cct aac ctt gag cac cag   1296
Thr Val Leu Pro Ala Val Val Ser Thr Leu Pro Asn Leu Glu His Gln
            420                 425                 430 gtg gct gaa ggg ctt cat cag agg agt att ctt gat tct cag tgc ggg   1344
Val Ala Glu Gly Leu His Gln Arg Ser Ile Leu Asp Ser Gln Cys Gly
        435                 440                 445 cca ggg gaa cct ctg agt gac agt ggt aga gag cgg cat ggg agc ttt   1392
Pro Gly Glu Pro Leu Ser Asp Ser Gly Arg Glu Arg His Gly Ser Phe
    450                 455                 460 gac agt cac tcg cgg ttc atg gta gca atg ata cac gaa cgc gat gga   1440
Asp Ser His Ser Arg Phe Met Val Ala Met Ile His Glu Arg Asp Gly
465                 470                 475                 480 tct gat tcc aac tca aat tcg tat gga cat gag cgg tac agc gga agt   1488
Ser Asp Ser Asn Ser Asn Ser Tyr Gly His Glu Arg Tyr Ser Gly Ser
                485                 490                 495 ttg act ggg ctt aat gac gtc ttg gag gga cgg aac agg tat acg aag   1536
Leu Thr Gly Leu Asn Asp Val Leu Glu Gly Arg Asn Arg Tyr Thr Lys
            500                 505                 510 ttg aag cag gac aag ggt cct cga tcc tct agt ctg aga tcc cat gag   1584
Leu Lys Gln Asp Lys Gly Pro Arg Ser Ser Ser Leu Arg Ser His Glu
        515                 520                 525 aaa gag gat gat att cag gaa gag gac ttg ctt gaa ctt ccc atg cta   1632
Lys Glu Asp Asp Ile Gln Glu Glu Asp Leu Leu Glu Leu Pro Met Leu
    530                 535                 540 tta ggc agt gag agt tct cat ggt ggt tcg aga gca tca cgg tct cca   1680
Leu Gly Ser Glu Ser Ser His Gly Gly Ser Arg Ala Ser Arg Ser Pro
545                 550                 555                 560 agt agt aga agt aaa gtt cag agc aag gca ggg agc aga gta ggg agc   1728
Ser Ser Arg Ser Lys Val Gln Ser Lys Ala Gly Ser Arg Val Gly Ser
                565                 570                 575 agg gta gaa agt aag gca gct agc agg gta ggg agt aag gct ggg tct   1776
Arg Val Glu Ser Lys Ala Ala Ser Arg Val Gly Ser Lys Ala Gly Ser
            580                 585                 590 gat gcc ttg aaa gat tgg gat cac aac gag gat aac tta ttg gaa tat   1824
Asp Ala Leu Lys Asp Trp Asp His Asn Glu Asp Asn Leu Leu Glu Tyr
        595                 600                 605 gca cta agc ttg ctt gaa gga act gat gga aaa aga ccc gga aca atc   1872
Ala Leu Ser Leu Leu Glu Gly Thr Asp Gly Lys Arg Pro Gly Thr Ile
    610                 615                 620 ggg tgg gcg cca gtg gat acc tcg ctc cca cga gaa tct gaa ggt ccc   1920
Gly Trp Ala Pro Val Asp Thr Ser Leu Pro Arg Glu Ser Glu Gly Pro
```

|  |  |  |  |  |  |  |  |  |  |  |  |  |  |  |  |
|---|---|---|---|---|---|---|---|---|---|---|---|---|---|---|---|
| 625 | | | | 630 | | | | 635 | | | | 640 | | | |

```
att cag tca tcc tct acc acg aga aac gag acc gag gag aat gaa aag   1968
Ile Gln Ser Ser Ser Thr Thr Arg Asn Glu Thr Glu Glu Asn Glu Lys
                645                 650                 655 gat act gtg tat aaa agt atc aag aat ggt aaa ggt agc gac aat gtg   2016
Asp Thr Val Tyr Lys Ser Ile Lys Asn Gly Lys Gly Ser Asp Asn Val
                660                 665                 670 ccc cag caa gta gtg ggg gcg gga gca aag gag gtt tct gag gga acg   2064
Pro Gln Gln Val Val Gly Ala Gly Ala Lys Glu Val Ser Glu Gly Thr
                675                 680                 685 att act ccg gtt gga cat cat ggt agt gca cct gat tgc tgt tcg aga   2112
Ile Thr Pro Val Gly His His Gly Ser Ala Pro Asp Cys Cys Ser Arg
            690                 695                 700 tgc gaa tcg ctt gtc tct cag tgt gag cag cta tca gtg gct ttg aag   2160
Cys Glu Ser Leu Val Ser Gln Cys Glu Gln Leu Ser Val Ala Leu Lys
705                 710                 715                 720 gag gct aga agg aaa caa caa gag aaa gat cga ctt gcg gag gaa aga   2208
Glu Ala Arg Arg Lys Gln Gln Glu Lys Asp Arg Leu Ala Glu Glu Arg
                725                 730                 735 gaa aaa caa ata agg cac ctt aca cag cta ctg cag tca ggg gaa cag   2256
Glu Lys Gln Ile Arg His Leu Thr Gln Leu Leu Gln Ser Gly Glu Gln
                740                 745                 750 ggc agt ttc tta caa gtc cta gat ctg ttg gac gag cac atg ccg gag   2304
Gly Ser Phe Leu Gln Val Leu Asp Leu Leu Asp Glu His Met Pro Glu
                755                 760                 765 gaa tac ctg agt cga gca agc tta ttc tgc cct gtt tct gaa gaa ttc   2352
Glu Tyr Leu Ser Arg Ala Ser Leu Phe Cys Pro Val Ser Glu Glu Phe
            770                 775                 780 aac ttc tcc gca gaa tct ttg ctg ggt ttt agt cat gag ttt aga ctt   2400
Asn Phe Ser Ala Glu Ser Leu Leu Gly Phe Ser His Glu Phe Arg Leu
785                 790                 795                 800 gcc gaa tgg agc aaa ctt tgt ccg aat gat ttc gcg ctc aca ttg tgc   2448
Ala Glu Trp Ser Lys Leu Cys Pro Asn Asp Phe Ala Leu Thr Leu Cys
                805                 810                 815 aac gaa tta cgt tgc aca ttt gct gat gat gag aac gcg ttc tgt tta   2496
Asn Glu Leu Arg Cys Thr Phe Ala Asp Asp Glu Asn Ala Phe Cys Leu
                820                 825                 830 ggg gag ttt atg agc tac gat cct ggt tca caa gcc acc ggc aga gtg   2544
Gly Glu Phe Met Ser Tyr Asp Pro Gly Ser Gln Ala Thr Gly Arg Val
                835                 840                 845 agg aag gtc gca atg agc gcc aac tat ggc aac ttg gac att cag aca   2592
Arg Lys Val Ala Met Ser Ala Asn Tyr Gly Asn Leu Asp Ile Gln Thr
            850                 855                 860 atg ctt tgg tgt cga agt ctt cga aga acg cat gac gac aat atg aag   2640
Met Leu Trp Cys Arg Ser Leu Arg Arg Thr His Asp Asp Asn Met Lys
865                 870                 875                 880 acg gtg aag aag ggg atg gag gta aag agg aag agt aga ttg agt aaa   2688
Thr Val Lys Lys Gly Met Glu Val Lys Arg Lys Ser Arg Leu Ser Lys
                885                 890                 895 acc agc gct ctt caa aag aaa atg cct aac tca aat gta gag gct gct   2736
Thr Ser Ala Leu Gln Lys Lys Met Pro Asn Ser Asn Val Glu Ala Ala
            900                 905                 910 aac tat cct cga tct gtt ttg caa act cgt tct cag gag act ccc tcg   2784
Asn Tyr Pro Arg Ser Val Leu Gln Thr Arg Ser Gln Glu Thr Pro Ser
            915                 920                 925 gcg tca cct cga cta tca aga ccg aag agt gct cag gtc cag caa gct   2832
Ala Ser Pro Arg Leu Ser Arg Pro Lys Ser Ala Gln Val Gln Gln Ala
            930                 935                 940 aag aag tta ctg aaa ata tta cgt cta gat cac atg ctt tct gat ggc   2880
```

```
        Lys Lys Leu Leu Lys Ile Leu Arg Leu Asp His Met Leu Ser Asp Gly
        945                 950                 955                 960 gac gaa gag gaa gaa aca gag agg atg agc aag aag aaa ggg atc aaa        2928
Asp Glu Glu Glu Glu Thr Glu Arg Met Ser Lys Lys Lys Gly Ile Lys
                        965                 970                 975 gaa aag aag aag cgt tgt ccg tac agg ctg agg tcg acc tcg tcc aaa        2976
Glu Lys Lys Lys Arg Cys Pro Tyr Arg Leu Arg Ser Thr Ser Ser Lys
                    980                 985                 990 ata cct cta tcc agg gaa ggt tct ccc cgt cca gtt gag agg agt gta        3024
Ile Pro Leu Ser Arg Glu Gly Ser Pro Arg Pro Val Glu Arg Ser Val
                995                 1000                1005 tct cct ttg aca tct tgg aga atg gat gat gcc ggt atg cca gaa            3069
Ser Pro Leu Thr Ser Trp Arg Met Asp Asp Ala Gly Met Pro Glu
        1010                1015                1020 cca ctg cgg gag aag ttg aat att ttt aag aaa gag cat gag acc            3114
Pro Leu Arg Glu Lys Leu Asn Ile Phe Lys Lys Glu His Glu Thr
        1025                1030                1035 atg tca agt caa caa act tcg aaa gaa cca gtg cag ttg aat caa            3159
Met Ser Ser Gln Gln Thr Ser Lys Glu Pro Val Gln Leu Asn Gln
        1040                1045                1050 ggt tcg gaa gaa gaa gag aat tat aac gac aca tct cat gct acg            3204
Gly Ser Glu Glu Glu Glu Asn Tyr Asn Asp Thr Ser His Ala Thr
        1055                1060                1065 cag tgg aat cac aaa cct ttg cga gga caa gcg cgg ggg gaa tct            3249
Gln Trp Asn His Lys Pro Leu Arg Gly Gln Ala Arg Gly Glu Ser
        1070                1075                1080 tgg caa gcc gat cac gta ggt ctc agt ctc aaa aag gag ccg cac            3294
Trp Gln Ala Asp His Val Gly Leu Ser Leu Lys Lys Glu Pro His
        1085                1090                1095 aat ttt gaa cta gat aag tta aag aat ata gta gca aca atg cag            3339
Asn Phe Glu Leu Asp Lys Leu Lys Asn Ile Val Ala Thr Met Gln
        1100                1105                1110 gag gag cac aga cag tgt att cgc agt atc gcg gag acc ctt gaa            3384
Glu Glu His Arg Gln Cys Ile Arg Ser Ile Ala Glu Thr Leu Glu
        1115                1120                1125 cat cac agc cgg cag att gtt ctc ttg acg aag gca aac tct tcc            3429
His His Ser Arg Gln Ile Val Leu Leu Thr Lys Ala Asn Ser Ser
        1130                1135                1140 ctg tcg aac cac gcg gat tcc tta gag aaa gag ctc atg gtg ttg            3474
Leu Ser Asn His Ala Asp Ser Leu Glu Lys Glu Leu Met Val Leu
        1145                1150                1155 cga gct atg cac ata aaa tcc gaa agt ctc ttt aat gct gta aaa            3519
Arg Ala Met His Ile Lys Ser Glu Ser Leu Phe Asn Ala Val Lys
        1160                1165                1170 ttg gcg gat tta aga gta gga tgt atc aag acc acc ttg tta aat            3564
Leu Ala Asp Leu Arg Val Gly Cys Ile Lys Thr Thr Leu Leu Asn
        1175                1180                1185 gct ctc ttg ttc tgc cat ttg tgc gca gaa acg aaa ggc gga gtt            3609
Ala Leu Leu Phe Cys His Leu Cys Ala Glu Thr Lys Gly Gly Val
        1190                1195                1200 ggg cat tat cga ggg aat agc ggt ctt ggc cga ata gac ctg gcg            3654
Gly His Tyr Arg Gly Asn Ser Gly Leu Gly Arg Ile Asp Leu Ala
        1205                1210                1215 aga aac agt gaa ctc ctc gac ctg agg ttg gac gat ctt ggt gat            3699
Arg Asn Ser Glu Leu Leu Asp Leu Arg Leu Asp Asp Leu Gly Asp
        1220                1225                1230 gag cgg caa gca aca aag gaa gat cga aga aaa caa agg ctc tcg            3744
Glu Arg Gln Ala Thr Lys Glu Asp Arg Arg Lys Gln Arg Leu Ser
        1235                1240                1245
```

-continued

| | |
|---|---|
| cct ccc tcg aat gtg aga gca aga cgt ggt agg gtc aca aag gga<br>Pro Pro Ser Asn Val Arg Ala Arg Arg Gly Arg Val Thr Lys Gly<br>1250                        1255                        1260 | 3789 |
| gcg ggg cca agg ttc gag aaa gcc tta gcc aag caa gca aca tgg<br>Ala Gly Pro Arg Phe Glu Lys Ala Leu Ala Lys Gln Ala Thr Trp<br>1265                        1270                        1275 | 3834 |
| cag cag ccg ata gca caa ctt ttg agg aac act gca ccg tca tca<br>Gln Gln Pro Ile Ala Gln Leu Leu Arg Asn Thr Ala Pro Ser Ser<br>1280                        1285                        1290 | 3879 |
| ccg agc aga aaa ggg caa agg tcg atg tgc tca atc gcc tct gca<br>Pro Ser Arg Lys Gly Gln Arg Ser Met Cys Ser Ile Ala Ser Ala<br>1295                        1300                        1305 | 3924 |
| agg ggg gag ttt ctg gat cga act tat cgg cgt caa agg aac ccc<br>Arg Gly Glu Phe Leu Asp Arg Thr Tyr Arg Arg Gln Arg Asn Pro<br>1310                        1315                        1320 | 3969 |
| gcc gaa gct tcc tcc aac act gaa tgg gga gtc agg tgg cgt ttt<br>Ala Glu Ala Ser Ser Asn Thr Glu Trp Gly Val Arg Trp Arg Phe<br>1325                        1330                        1335 | 4014 |
| atc ctt cgc gcc aaa aca ttc cag gtg gcg ttc cat agc aag cat<br>Ile Leu Arg Ala Lys Thr Phe Gln Val Ala Phe His Ser Lys His<br>1340                        1345                        1350 | 4059 |
| ctt aaa att tgt gca aat aca tgc aag aat taa<br>Leu Lys Ile Cys Ala Asn Thr Cys Lys Asn<br>1355                        1360 | 4092 |

<210> SEQ ID NO 21
<211> LENGTH: 1363
<212> TYPE: PRT
<213> ORGANISM: Physcomitrella patens

<400> SEQUENCE: 21

Met Val Leu Leu Met Asn Arg Asn Ala Leu Gly Ile His Phe Gly Ala
1               5                   10                  15

Arg Ala Ser Leu Ala Val Met Val Ile His Trp Tyr Leu Arg Pro Gly
            20                  25                  30

Glu Leu Thr Pro Cys Ser Pro Thr Asn Gly Pro Leu Trp Lys Trp Met
        35                  40                  45

Arg Thr Ile Leu Pro Phe Pro Val Pro Val Asp Leu Lys Arg Glu Ala
    50                  55                  60

Val Leu Ala Gly Thr Val Val Val Tyr Ser Val Leu Lys Met Pro Val
65                  70                  75                  80

Leu Trp Ser Ser Ser Leu Asp Ala Asp Ala Asp Ala Ala Thr Asn
                85                  90                  95

Arg His Ser Ser Ser Thr Phe Val Arg Asp Gly Trp Arg Ala Leu Thr
            100                 105                 110

Gly Arg Gly Gln Gly Pro Lys Leu Arg Arg Val Glu Gly Met Glu Thr
        115                 120                 125

Arg Val Val Ser Ala Glu Glu Leu Val Leu Pro Met Val Ala Leu Ala
    130                 135                 140

Trp Val Val His Lys Phe Leu Trp Ala Leu Trp Lys Leu Trp Arg
145                 150                 155                 160

Ser Ala Val Asp Asp Ile Asn Ile Gly Arg Thr Lys Arg Leu Cys Pro
                165                 170                 175

Thr Ser Ser Gln Met Ala Arg Gly Gly Cys Cys Trp Ser Gly Pro Phe
            180                 185                 190

Cys Leu Gly Ser Leu Ser Arg Lys Asn Lys Lys Arg Ile Val Pro Ala
        195                 200                 205

```
Thr Arg Val His Asp Gly Thr Ala Gln Pro Ser Asp Pro Gln Gly Gln
210                 215                 220

Phe Ala Phe Leu Leu Ala Pro Pro Ser Ser Pro Ala Ser Tyr Ala Asn
225                 230                 235                 240

Ser Met Ala Pro Ser Ser Val Gln Ser Pro Tyr Tyr Pro Ser Ser Cys
                245                 250                 255

Pro Val Pro Gln Gly Gly Ser Arg Ile Pro Leu Glu Thr Gln Ser
            260                 265                 270

Asn Met Phe Ala Val Gly Pro Tyr Ala His Glu Thr Ala Leu Val Ser
                275                 280                 285

Pro Pro Val Phe Ser Thr Phe Thr Thr Ala Pro Ser Thr Ala Pro Phe
            290                 295                 300

Thr Pro Pro Pro Glu Leu Ala Ala His Phe Thr Thr Pro Ser Ser Pro
305                 310                 315                 320

Asp Val Pro Phe Ala Lys Leu Leu Gly Ser Ser Phe Ser Glu Gln Arg
                325                 330                 335

Thr Thr Lys Arg Glu Ala Glu Pro Pro Tyr Ser Ala Ser Pro Phe Ala
                340                 345                 350

Ser Pro Asp Tyr Tyr Gln Gln Asp His His Pro Gln Asp Asp Leu Gln
                355                 360                 365

Val Gly Tyr Gln Leu Tyr Pro Gly Ser Pro Leu Gly Arg Leu Ile Ser
    370                 375                 380

Pro Ala Gly Thr Thr Gly Ala Ser Thr Pro Phe Ala Ala Gly Gly Thr
385                 390                 395                 400

Thr Gly Thr Asn Thr Pro His Ala Glu Ser Asp Asn Pro Thr Pro Leu
                405                 410                 415

Thr Val Leu Pro Ala Val Val Ser Thr Leu Pro Asn Leu Glu His Gln
                420                 425                 430

Val Ala Glu Gly Leu His Gln Arg Ser Ile Leu Asp Ser Gln Cys Gly
            435                 440                 445

Pro Gly Glu Pro Leu Ser Asp Ser Gly Arg Glu Arg His Gly Ser Phe
            450                 455                 460

Asp Ser His Ser Arg Phe Met Val Ala Met Ile His Glu Arg Asp Gly
465                 470                 475                 480

Ser Asp Ser Asn Ser Asn Ser Tyr Gly His Glu Arg Tyr Ser Gly Ser
                485                 490                 495

Leu Thr Gly Leu Asn Asp Val Leu Glu Gly Arg Asn Arg Tyr Thr Lys
            500                 505                 510

Leu Lys Gln Asp Lys Gly Pro Arg Ser Ser Leu Arg Ser His Glu
            515                 520                 525

Lys Glu Asp Asp Ile Gln Glu Glu Asp Leu Leu Glu Leu Pro Met Leu
530                 535                 540

Leu Gly Ser Glu Ser Ser His Gly Gly Ser Arg Ala Ser Arg Ser Pro
545                 550                 555                 560

Ser Ser Arg Ser Lys Val Gln Ser Lys Ala Gly Ser Arg Val Gly Ser
                565                 570                 575

Arg Val Glu Ser Lys Ala Ala Ser Arg Val Gly Ser Lys Ala Gly Ser
            580                 585                 590

Asp Ala Leu Lys Asp Trp Asp His Asn Glu Asp Asn Leu Leu Glu Tyr
                595                 600                 605

Ala Leu Ser Leu Leu Glu Gly Thr Asp Gly Lys Arg Pro Gly Thr Ile
    610                 615                 620

Gly Trp Ala Pro Val Asp Thr Ser Leu Pro Arg Glu Ser Glu Gly Pro
```

```
              625                 630                 635                 640
Ile Gln Ser Ser Ser Thr Thr Arg Asn Glu Thr Glu Glu Asn Glu Lys
                    645                 650                 655

Asp Thr Val Tyr Lys Ser Ile Lys Asn Gly Lys Gly Ser Asp Asn Val
                    660                 665                 670

Pro Gln Gln Val Val Gly Ala Gly Ala Lys Glu Val Ser Glu Gly Thr
                    675                 680                 685

Ile Thr Pro Val Gly His His Gly Ser Ala Pro Asp Cys Cys Ser Arg
                    690                 695                 700

Cys Glu Ser Leu Val Ser Gln Cys Glu Gln Leu Ser Val Ala Leu Lys
705                 710                 715                 720

Glu Ala Arg Arg Lys Gln Gln Glu Lys Asp Arg Leu Ala Glu Glu Arg
                    725                 730                 735

Glu Lys Gln Ile Arg His Leu Thr Gln Leu Leu Gln Ser Gly Glu Gln
                    740                 745                 750

Gly Ser Phe Leu Gln Val Leu Asp Leu Leu Asp Glu His Met Pro Glu
                    755                 760                 765

Glu Tyr Leu Ser Arg Ala Ser Leu Phe Cys Pro Val Ser Glu Glu Phe
                    770                 775                 780

Asn Phe Ser Ala Glu Ser Leu Leu Gly Phe Ser His Glu Phe Arg Leu
785                 790                 795                 800

Ala Glu Trp Ser Lys Leu Cys Pro Asn Asp Phe Ala Leu Thr Leu Cys
                    805                 810                 815

Asn Glu Leu Arg Cys Thr Phe Ala Asp Asp Glu Asn Ala Phe Cys Leu
                    820                 825                 830

Gly Glu Phe Met Ser Tyr Asp Pro Gly Ser Gln Ala Thr Gly Arg Val
                    835                 840                 845

Arg Lys Val Ala Met Ser Ala Asn Tyr Gly Asn Leu Asp Ile Gln Thr
                    850                 855                 860

Met Leu Trp Cys Arg Ser Leu Arg Arg Thr His Asp Asp Asn Met Lys
865                 870                 875                 880

Thr Val Lys Lys Gly Met Glu Val Lys Arg Lys Ser Arg Leu Ser Lys
                    885                 890                 895

Thr Ser Ala Leu Gln Lys Lys Met Pro Asn Ser Asn Val Glu Ala Ala
                    900                 905                 910

Asn Tyr Pro Arg Ser Val Leu Gln Thr Arg Ser Gln Glu Thr Pro Ser
                    915                 920                 925

Ala Ser Pro Arg Leu Ser Arg Pro Lys Ser Ala Gln Val Gln Gln Ala
                    930                 935                 940

Lys Lys Leu Leu Lys Ile Leu Arg Leu Asp His Met Leu Ser Asp Gly
945                 950                 955                 960

Asp Glu Glu Glu Glu Thr Glu Arg Met Ser Lys Lys Lys Gly Ile Lys
                    965                 970                 975

Glu Lys Lys Lys Arg Cys Pro Tyr Arg Leu Arg Ser Thr Ser Ser Lys
                    980                 985                 990

Ile Pro Leu Ser Arg Glu Gly Ser  Pro Arg Pro Val Glu  Arg Ser Val
                    995                 1000                1005

Ser Pro Leu Thr Ser Trp Arg Met Asp Asp Ala Gly  Met Pro Glu
        1010                1015                1020

Pro Leu Arg Glu Lys Leu Asn  Ile Phe Lys Lys Glu  His Glu Thr
        1025                1030                1035

Met Ser Ser Gln Gln Thr Ser Lys Glu Pro Val Gln  Leu Asn Gln
        1040                1045                1050
```

Gly Ser Glu Glu Glu Glu Asn Tyr Asn Asp Thr Ser His Ala Thr
    1055                1060                1065

Gln Trp Asn His Lys Pro Leu Arg Gly Gln Ala Arg Gly Glu Ser
    1070                1075                1080

Trp Gln Ala Asp His Val Gly Leu Ser Leu Lys Lys Glu Pro His
    1085                1090                1095

Asn Phe Glu Leu Asp Lys Leu Lys Asn Ile Val Ala Thr Met Gln
    1100                1105                1110

Glu Glu His Arg Gln Cys Ile Arg Ser Ile Ala Glu Thr Leu Glu
    1115                1120                1125

His His Ser Arg Gln Ile Val Leu Leu Thr Lys Ala Asn Ser Ser
    1130                1135                1140

Leu Ser Asn His Ala Asp Ser Leu Glu Lys Glu Leu Met Val Leu
    1145                1150                1155

Arg Ala Met His Ile Lys Ser Glu Ser Leu Phe Asn Ala Val Lys
    1160                1165                1170

Leu Ala Asp Leu Arg Val Gly Cys Ile Lys Thr Thr Leu Leu Asn
    1175                1180                1185

Ala Leu Leu Phe Cys His Leu Cys Ala Glu Thr Lys Gly Gly Val
    1190                1195                1200

Gly His Tyr Arg Gly Asn Ser Gly Leu Gly Arg Ile Asp Leu Ala
    1205                1210                1215

Arg Asn Ser Glu Leu Leu Asp Leu Arg Leu Asp Asp Leu Gly Asp
    1220                1225                1230

Glu Arg Gln Ala Thr Lys Glu Asp Arg Arg Lys Gln Arg Leu Ser
    1235                1240                1245

Pro Pro Ser Asn Val Arg Ala Arg Arg Gly Arg Val Thr Lys Gly
    1250                1255                1260

Ala Gly Pro Arg Phe Glu Lys Ala Leu Ala Lys Gln Ala Thr Trp
    1265                1270                1275

Gln Gln Pro Ile Ala Gln Leu Leu Arg Asn Thr Ala Pro Ser Ser
    1280                1285                1290

Pro Ser Arg Lys Gly Gln Arg Ser Met Cys Ser Ile Ala Ser Ala
    1295                1300                1305

Arg Gly Glu Phe Leu Asp Arg Thr Tyr Arg Arg Gln Arg Asn Pro
    1310                1315                1320

Ala Glu Ala Ser Ser Asn Thr Glu Trp Gly Val Arg Trp Arg Phe
    1325                1330                1335

Ile Leu Arg Ala Lys Thr Phe Gln Val Ala Phe His Ser Lys His
    1340                1345                1350

Leu Lys Ile Cys Ala Asn Thr Cys Lys Asn
    1355                1360

<210> SEQ ID NO 22
<211> LENGTH: 1886
<212> TYPE: DNA
<213> ORGANISM: Arabidopsis thaliana
<220> FEATURE:
<221> NAME/KEY: CDS
<222> LOCATION: (227)..(1543)

<400> SEQUENCE: 22
aagctggact agataacgac cggtgtgagt gagagagaga gagagagaat tcgatccatc    60
attatacaaa accttcttcg ctttttattt gatttattta tccttttctc atttgatttt   120

```
ctcgggaaaa tctctctgcg tagtagatcc aagtggtggt ttctgagtag tagtaagcaa    180
gcaaatctgg atgttattgt agtcggtgtg aatctgagtt cgaaag atg agg aac      235
                                                    Met Arg Asn
                                                    1 gtt gtt aat aac agc gtt gag act gtt aac gcc gcc gct acc gcc atc     283
Val Val Asn Asn Ser Val Glu Thr Val Asn Ala Ala Ala Thr Ala Ile
    5              10                  15 gtc acc gcc gag tct cga gta cag ccg tct tct cag aag gga aga         331
Val Thr Ala Glu Ser Arg Val Gln Pro Ser Ser Gln Lys Gly Arg
20              25                  30                  35 tgg gga aaa tgt tgg agt tta tat tca tgt ttt gga act cag aag aac     379
Trp Gly Lys Cys Trp Ser Leu Tyr Ser Cys Phe Gly Thr Gln Lys Asn
                40                  45                  50 aat aaa agg att ggt aat gct gtg ctt gta cct gaa ccg gtt aca tct     427
Asn Lys Arg Ile Gly Asn Ala Val Leu Val Pro Glu Pro Val Thr Ser
            55                  60                  65 gga gtt ccg gta gtt act gtt caa aac tca gct act tca act act gtt     475
Gly Val Pro Val Val Thr Val Gln Asn Ser Ala Thr Ser Thr Thr Val
        70                  75                  80 gtt ctt ccc ttt ata gct cct cct tca tct cca gct tcg ttt ttg caa     523
Val Leu Pro Phe Ile Ala Pro Pro Ser Ser Pro Ala Ser Phe Leu Gln
    85                  90                  95 tcg gat cct tca tcg gtt tct cac tcg cct gtt ggt cca ctt tct ctt     571
Ser Asp Pro Ser Ser Val Ser His Ser Pro Val Gly Pro Leu Ser Leu
100             105                 110                 115 act agc aat aca ttc tcg cct aag gag cct caa tct gtc ttt acc gtt     619
Thr Ser Asn Thr Phe Ser Pro Lys Glu Pro Gln Ser Val Phe Thr Val
                120                 125                 130 gga cct tat gct aat gaa act caa cca gtc act cct ccg gtg ttc tct     667
Gly Pro Tyr Ala Asn Glu Thr Gln Pro Val Thr Pro Pro Val Phe Ser
            135                 140                 145 gcg ttt ata act gag cca tct act gca ccg tat act cca cct cct gaa     715
Ala Phe Ile Thr Glu Pro Ser Thr Ala Pro Tyr Thr Pro Pro Pro Glu
        150                 155                 160 tca tca gtc cat ata act aca cct tct tca cct gaa gtg ccc ttt gct     763
Ser Ser Val His Ile Thr Thr Pro Ser Ser Pro Glu Val Pro Phe Ala
    165                 170                 175 cag ttg ctt act tct tcg ttg gag cta act cgg agg gat agt act agt     811
Gln Leu Leu Thr Ser Ser Leu Glu Leu Thr Arg Arg Asp Ser Thr Ser
180                 185                 190                 195 ggg atg aat caa aag ttt tcg tct tcg cac tat gag ttt cgg tct aat     859
Gly Met Asn Gln Lys Phe Ser Ser Ser His Tyr Glu Phe Arg Ser Asn
                200                 205                 210 cag gtg tgt ccg ggg agt cct ggt ggt ggt aat cta atc tct ccc ggg     907
Gln Val Cys Pro Gly Ser Pro Gly Gly Gly Asn Leu Ile Ser Pro Gly
            215                 220                 225 tca gtg att tca aac tct ggt aca tct tct cct tac cct ggt aaa tca     955
Ser Val Ile Ser Asn Ser Gly Thr Ser Ser Pro Tyr Pro Gly Lys Ser
        230                 235                 240 ccc atg gtt gag ttt cga ata ggc gag cct cca aag ttc ttg ggt ttt    1003
Pro Met Val Glu Phe Arg Ile Gly Glu Pro Pro Lys Phe Leu Gly Phe
    245                 250                 255 gag cac ttt aca gct cgt aaa tgg gga tcg agg ttc ggt tct gga tcg    1051
Glu His Phe Thr Ala Arg Lys Trp Gly Ser Arg Phe Gly Ser Gly Ser
260                 265                 270                 275 atc aca cct gtt ggg cat ggt tca ggt ttg gct tca ggc gct ctg aca    1099
Ile Thr Pro Val Gly His Gly Ser Gly Leu Ala Ser Gly Ala Leu Thr
                280                 285                 290 cca aat ggt cca gag ata gta tct gga aac tta aca ccc aac aat acc    1147
```

```
                Pro Asn Gly Pro Glu Ile Val Ser Gly Asn Leu Thr Pro Asn Asn Thr
                            295                 300                 305 aca tgg cct ctt caa aat cag atc tct gag gtc gct tca ctg gca aat      1195
Thr Trp Pro Leu Gln Asn Gln Ile Ser Glu Val Ala Ser Leu Ala Asn
            310                 315                 320 tcg gat cat ggc tct gaa gtc atg gta gca gat cac aga gtt tcg ttt      1243
Ser Asp His Gly Ser Glu Val Met Val Ala Asp His Arg Val Ser Phe
325                 330                 335 gag tta aca ggt gaa gac gtt gca cgt tgt ctt gca agc aag cta aat      1291
Glu Leu Thr Gly Glu Asp Val Ala Arg Cys Leu Ala Ser Lys Leu Asn
340                 345                 350                 355 cga tca cac gac aga atg aac aac aat gac cgg atc gaa aca gag gag      1339
Arg Ser His Asp Arg Met Asn Asn Asn Asp Arg Ile Glu Thr Glu Glu
            360                 365                 370 agt tca tca aca gac ata aga aga aac ata gag aaa agg tca gga gac      1387
Ser Ser Ser Thr Asp Ile Arg Arg Asn Ile Glu Lys Arg Ser Gly Asp
            375                 380                 385 aga gag aac gaa cag cat aga att cag aag ctg agt tcc tca tcg att      1435
Arg Glu Asn Glu Gln His Arg Ile Gln Lys Leu Ser Ser Ser Ile
            390                 395                 400 gga tct agc aaa gaa ttt aaa ttc gac aac acg aaa gac gag aat atc      1483
Gly Ser Ser Lys Glu Phe Lys Phe Asp Asn Thr Lys Asp Glu Asn Ile
405                 410                 415 gag aag gtt gca gga aac agc tgg agt ttc ttc ccg ggg tta cga tct      1531
Glu Lys Val Ala Gly Asn Ser Trp Ser Phe Phe Pro Gly Leu Arg Ser
420                 425                 430                 435 gga gtc agc taa ccaaattaaa atgcatctc ttcttcttct tcctcattac           1583
Gly Val Ser caaagacaga gatataaaac cctataagta acaaaccttg aacatggatc gtgaaaaaag    1643
gtaagagatt tgggttctaa caacttatac acactgaata aataagctta aagctttgat    1703
ttgcagttaa cttctgtact catgtagttg gaaactttgg aatattcttg gatcagctcc    1763
tacatctaat cttgttacat tgatataaat tgtttatttc ttgttttact gtttcataca    1823
aatatattgt ttgaactgag atcgtgaatg gtcttattct atatcattac taaaacattt    1883
tca                                                                  1886

<210> SEQ ID NO 23
<211> LENGTH: 438
<212> TYPE: PRT
<213> ORGANISM: Arabidopsis thaliana

<400> SEQUENCE: 23

Met Arg Asn Val Val Asn Asn Ser Val Glu Thr Val Asn Ala Ala Ala
1               5                   10                  15

Thr Ala Ile Val Thr Ala Glu Ser Arg Val Gln Pro Ser Ser Ser Gln
            20                  25                  30

Lys Gly Arg Trp Gly Lys Cys Trp Ser Leu Tyr Ser Cys Phe Gly Thr
        35                  40                  45

Gln Lys Asn Asn Lys Arg Ile Gly Asn Ala Val Leu Val Pro Glu Pro
    50                  55                  60

Val Thr Ser Gly Val Pro Val Val Thr Val Gln Asn Ser Ala Thr Ser
65                  70                  75                  80

Thr Thr Val Val Leu Pro Phe Ile Ala Pro Ser Ser Pro Ala Ser
                85                  90                  95

Phe Leu Gln Ser Asp Pro Ser Ser Val Ser His Ser Pro Val Gly Pro
            100                 105                 110
```

```
Leu Ser Leu Thr Ser Asn Thr Phe Ser Pro Lys Glu Pro Gln Ser Val
        115                 120                 125
Phe Thr Val Gly Pro Tyr Ala Asn Glu Thr Gln Pro Val Thr Pro Pro
    130                 135                 140
Val Phe Ser Ala Phe Ile Thr Glu Pro Ser Thr Ala Pro Tyr Thr Pro
145                 150                 155                 160
Pro Pro Glu Ser Ser Val His Ile Thr Thr Pro Ser Ser Pro Glu Val
                165                 170                 175
Pro Phe Ala Gln Leu Leu Thr Ser Ser Leu Glu Leu Thr Arg Arg Asp
            180                 185                 190
Ser Thr Ser Gly Met Asn Gln Lys Phe Ser Ser His Tyr Glu Phe
        195                 200                 205
Arg Ser Asn Gln Val Cys Pro Gly Ser Pro Gly Gly Asn Leu Ile
    210                 215                 220
Ser Pro Gly Ser Val Ile Ser Asn Ser Gly Thr Ser Ser Pro Tyr Pro
225                 230                 235                 240
Gly Lys Ser Pro Met Val Glu Phe Arg Ile Gly Glu Pro Pro Lys Phe
                245                 250                 255
Leu Gly Phe Glu His Phe Thr Ala Arg Lys Trp Gly Ser Arg Phe Gly
            260                 265                 270
Ser Gly Ser Ile Thr Pro Val Gly His Gly Ser Gly Leu Ala Ser Gly
        275                 280                 285
Ala Leu Thr Pro Asn Gly Pro Glu Ile Val Ser Gly Asn Leu Thr Pro
    290                 295                 300
Asn Asn Thr Thr Trp Pro Leu Gln Asn Gln Ile Ser Glu Val Ala Ser
305                 310                 315                 320
Leu Ala Asn Ser Asp His Gly Ser Glu Val Met Val Ala Asp His Arg
                325                 330                 335
Val Ser Phe Glu Leu Thr Gly Glu Asp Val Ala Arg Cys Leu Ala Ser
            340                 345                 350
Lys Leu Asn Arg Ser His Asp Arg Met Asn Asn Asp Arg Ile Glu
        355                 360                 365
Thr Glu Glu Ser Ser Ser Thr Asp Ile Arg Arg Asn Ile Glu Lys Arg
    370                 375                 380
Ser Gly Asp Arg Glu Asn Glu Gln His Arg Ile Gln Lys Leu Ser Ser
385                 390                 395                 400
Ser Ser Ile Gly Ser Ser Lys Glu Phe Lys Phe Asp Asn Thr Lys Asp
                405                 410                 415
Glu Asn Ile Glu Lys Val Ala Gly Asn Ser Trp Ser Phe Phe Pro Gly
            420                 425                 430
Leu Arg Ser Gly Val Ser
        435

<210> SEQ ID NO 24
<211> LENGTH: 1994
<212> TYPE: DNA
<213> ORGANISM: Arabidopsis thaliana
<220> FEATURE:
<221> NAME/KEY: CDS
<222> LOCATION: (384)..(1733)

<400> SEQUENCE: 24
gataatttta atattttaac acaataatag cgaataaata atatatacat ggaagcgcgt      60
gggtccaaac cgtcaaatta tgatgacgtg gcaaaatctc gtgggaaatt gaatgaaaac     120
tgtaaaagat aacgaccggt gacagagaga gagagagagg agaagaagaa tagaagaagc     180
```

```
ggctcatatc cataataaaa gccatttgct cctttattta ttctctcatt ctttcttctt      240
cattattcat ttctctcgtt attcgtttcg tattttgttt gtgtttatga ttttacctcc      300
ttagttgctg tgagatcaag aagtggtgaa agaaaagtta ctaaatctgg atgttatttg      360
attgtcgtcg ttggtcttga gct atg agg agc gtt aat aat agt agt gtc gac     413
                          Met Arg Ser Val Asn Asn Ser Ser Val Asp
                           1               5                   10 acc gtg aac gcc gcc gct tcc gcc atc gtc tcc gct gag tct aga aca        461
Thr Val Asn Ala Ala Ala Ser Ala Ile Val Ser Ala Glu Ser Arg Thr
             15                  20                  25 caa ccg tcg tcg gtt cag aaa aaa agg gga agc tgg tgg agc ttg tac        509
Gln Pro Ser Ser Val Gln Lys Lys Arg Gly Ser Trp Trp Ser Leu Tyr
         30                  35                  40 tgg tgt ttt gga tcc aag aag aac aat aaa agg ata ggc cac gcg gtg        557
Trp Cys Phe Gly Ser Lys Lys Asn Asn Lys Arg Ile Gly His Ala Val
     45                  50                  55 ctt gta ccc gaa cca gct gca tca gga gct gcg gtg gct cca gtc caa        605
Leu Val Pro Glu Pro Ala Ala Ser Gly Ala Ala Val Ala Pro Val Gln
 60                  65                  70 aac tct tcg agc aat tct act tca ata ttc atg ccc ttt ata gct cct        653
Asn Ser Ser Ser Asn Ser Thr Ser Ile Phe Met Pro Phe Ile Ala Pro
75                  80                  85                  90 cct tca tct cct gct tcc ttt ctg cca tca ggt cct ccc tct gcg tca        701
Pro Ser Ser Pro Ala Ser Phe Leu Pro Ser Gly Pro Pro Ser Ala Ser
             95                 100                 105 cat act cct gat cct ggt cta ctt tgt tcc cta acc gtc aat gaa ccg        749
His Thr Pro Asp Pro Gly Leu Leu Cys Ser Leu Thr Val Asn Glu Pro
        110                 115                 120 cct tca gcc ttt act att gga cca tac gct cat gag act caa cct gtt        797
Pro Ser Ala Phe Thr Ile Gly Pro Tyr Ala His Glu Thr Gln Pro Val
        125                 130                 135 act cct cca gtg ttc tct gct ttc aca acg gaa ccc tcc acc gcg cca        845
Thr Pro Pro Val Phe Ser Ala Phe Thr Thr Glu Pro Ser Thr Ala Pro
        140                 145                 150 ttc acg cca cct cct gaa tca cct tct tcc cct gaa gtg cct ttt gct        893
Phe Thr Pro Pro Pro Glu Ser Pro Ser Ser Pro Glu Val Pro Phe Ala
155                 160                 165                 170 cag tta ctt aca tct tca ttg gaa agg gct agg agg aac agt ggt ggt        941
Gln Leu Leu Thr Ser Ser Leu Glu Arg Ala Arg Arg Asn Ser Gly Gly
            175                 180                 185 gga atg aat cag aag ttt tca gct gca cac tac gag ttt aag tct tgt        989
Gly Met Asn Gln Lys Phe Ser Ala Ala His Tyr Glu Phe Lys Ser Cys
        190                 195                 200 caa gtg tat cct gga agt cca ggt ggt aat cta atc tct cct ggt tca       1037
Gln Val Tyr Pro Gly Ser Pro Gly Gly Asn Leu Ile Ser Pro Gly Ser
        205                 210                 215 ggt aca tct tct cct tac cca ggg aaa tgc tcc atc atc gag ttt cgt       1085
Gly Thr Ser Ser Pro Tyr Pro Gly Lys Cys Ser Ile Ile Glu Phe Arg
220                 225                 230 atc ggc gaa cct cca aag ttt ctt ggt ttt gag cac ttc aca gcg cgt       1133
Ile Gly Glu Pro Pro Lys Phe Leu Gly Phe Glu His Phe Thr Ala Arg
235                 240                 245                 250 aaa tgg gga tca aga ttc ggt tct gga tcc atc aca cct gct gga caa       1181
Lys Trp Gly Ser Arg Phe Gly Ser Gly Ser Ile Thr Pro Ala Gly Gln
            255                 260                 265 ggt tca agg ttg ggt tca ggt gct ttg act cct gat ggc tca aag cta       1229
Gly Ser Arg Leu Gly Ser Gly Ala Leu Thr Pro Asp Gly Ser Lys Leu
        270                 275                 280
```

| | | |
|---|---|---|
| act tct ggt gta gtg aca cca aat ggt gca gag act gtt ata aga atg<br>Thr Ser Gly Val Val Thr Pro Asn Gly Ala Glu Thr Val Ile Arg Met<br>285                       290                       295 | 1277 |
| agt tat ggg aat ctc aca cca ctt gaa ggc agt ctt ttg gat agt cag<br>Ser Tyr Gly Asn Leu Thr Pro Leu Glu Gly Ser Leu Leu Asp Ser Gln<br>300                       305                       310 | 1325 |
| atc tct gag gtt gcg tct tta gcc aat tcg gac cac ggg tcg tca agg<br>Ile Ser Glu Val Ala Ser Leu Ala Asn Ser Asp His Gly Ser Ser Arg<br>315                       320                       325                       330 | 1373 |
| cat aat gat gaa gct ctc gtg gtt cct cac aga gtt tct ttc gag ttg<br>His Asn Asp Glu Ala Leu Val Val Pro His Arg Val Ser Phe Glu Leu<br>                       335                       340                       345 | 1421 |
| act ggt gaa gac gtt gca cgg tgt ctt gca agc aag cta aac cgt tcc<br>Thr Gly Glu Asp Val Ala Arg Cys Leu Ala Ser Lys Leu Asn Arg Ser<br>         350                       355                       360 | 1469 |
| ggt tca cat gaa aaa gca agc ggc gaa cat tta aga cca aac tgt tgt<br>Gly Ser His Glu Lys Ala Ser Gly Glu His Leu Arg Pro Asn Cys Cys<br>         365                       370                       375 | 1517 |
| aaa acg tcg gga gaa aca gag agc gaa cag agt cag aag cta aga tcg<br>Lys Thr Ser Gly Glu Thr Glu Ser Glu Gln Ser Gln Lys Leu Arg Ser<br>380                       385                       390 | 1565 |
| ttt tct aca ggc tct aac aaa gaa ttc aag ttt gat agc acc aat gaa<br>Phe Ser Thr Gly Ser Asn Lys Glu Phe Lys Phe Asp Ser Thr Asn Glu<br>395                       400                       405                       410 | 1613 |
| gag atg ata gag aaa att cga tcg gag tgg tgg gcg aat gag aag gtc<br>Glu Met Ile Glu Lys Ile Arg Ser Glu Trp Trp Ala Asn Glu Lys Val<br>                       415                       420                       425 | 1661 |
| gcc gga aaa ggt gat cac agt cca aga aac agt tgg act ttc ttt cca<br>Ala Gly Lys Gly Asp His Ser Pro Arg Asn Ser Trp Thr Phe Phe Pro<br>         430                       435                       440 | 1709 |
| gtc tta cgc tct gga cat act tag cacaaagaaa tagctttac cttcttcatt<br>Val Leu Arg Ser Gly His Thr<br>         445 | 1763 |
| acctctaaca tgggaagcaa agtcagtgat atggtaagag attggggtct aacaactata | 1823 |
| catatatata gcttggtatt gtaggtgtct tgttctttg tactgttaat tatataaaat | 1883 |
| agttttaaca cttaaatggt agacttatca ttgacaaaag aaaagaaact gtattctttc | 1943 |
| ttggttatgt ataaacataa aaatcatctc tttactatat tgtcttacat t | 1994 |

<210> SEQ ID NO 25
<211> LENGTH: 449
<212> TYPE: PRT
<213> ORGANISM: Arabidopsis thaliana

<400> SEQUENCE: 25

Met Arg Ser Val Asn Asn Ser Ser Val Asp Thr Val Asn Ala Ala Ala
1               5                   10                 15

Ser Ala Ile Val Ser Ala Glu Ser Arg Thr Gln Pro Ser Ser Val Gln
                  20                   25                   30

Lys Lys Arg Gly Ser Trp Trp Ser Leu Tyr Trp Cys Phe Gly Ser Lys
        35                       40                   45

Lys Asn Asn Lys Arg Ile Gly His Ala Val Leu Val Pro Glu Pro Ala
        50                       55                   60

Ala Ser Gly Ala Ala Val Ala Pro Val Gln Asn Ser Ser Ser Asn Ser
65                     70                   75                 80

Thr Ser Ile Phe Met Pro Phe Ile Ala Pro Pro Ser Ser Pro Ala Ser
                  85                   90                   95

Phe Leu Pro Ser Gly Pro Pro Ser Ala Ser His Thr Pro Asp Pro Gly

|   |   |   |   |   | 100 |   |   |   |   | 105 |   |   |   |   | 110 |   |
|---|---|---|---|---|---|---|---|---|---|---|---|---|---|---|---|---|
| Leu | Leu | Cys | Ser | Leu | Thr | Val | Asn | Glu | Pro | Pro | Ser | Ala | Phe | Thr | Ile |   |
|   |   |   |   | 115 |   |   |   |   | 120 |   |   |   |   | 125 |   |   |
| Gly | Pro | Tyr | Ala | His | Glu | Thr | Gln | Pro | Val | Thr | Pro | Pro | Val | Phe | Ser |   |
|   |   |   | 130 |   |   |   |   | 135 |   |   |   |   | 140 |   |   |   |
| Ala | Phe | Thr | Thr | Glu | Pro | Ser | Thr | Ala | Pro | Phe | Thr | Pro | Pro | Pro | Glu |   |
| 145 |   |   |   |   | 150 |   |   |   |   | 155 |   |   |   |   | 160 |   |
| Ser | Pro | Ser | Ser | Pro | Glu | Val | Pro | Phe | Ala | Gln | Leu | Leu | Thr | Ser | Ser |   |
|   |   |   |   | 165 |   |   |   |   | 170 |   |   |   |   | 175 |   |   |
| Leu | Glu | Arg | Ala | Arg | Arg | Asn | Ser | Gly | Gly | Gly | Met | Asn | Gln | Lys | Phe |   |
|   |   |   | 180 |   |   |   |   | 185 |   |   |   |   | 190 |   |   |   |
| Ser | Ala | Ala | His | Tyr | Glu | Phe | Lys | Ser | Cys | Gln | Val | Tyr | Pro | Gly | Ser |   |
|   |   | 195 |   |   |   |   | 200 |   |   |   |   | 205 |   |   |   |   |
| Pro | Gly | Gly | Asn | Leu | Ile | Ser | Pro | Gly | Ser | Gly | Thr | Ser | Ser | Pro | Tyr |   |
|   | 210 |   |   |   |   | 215 |   |   |   |   | 220 |   |   |   |   |   |
| Pro | Gly | Lys | Cys | Ser | Ile | Ile | Glu | Phe | Arg | Ile | Gly | Glu | Pro | Pro | Lys |   |
| 225 |   |   |   |   | 230 |   |   |   |   | 235 |   |   |   |   | 240 |   |
| Phe | Leu | Gly | Phe | Glu | His | Phe | Thr | Ala | Arg | Lys | Trp | Gly | Ser | Arg | Phe |   |
|   |   |   |   | 245 |   |   |   |   | 250 |   |   |   |   | 255 |   |   |
| Gly | Ser | Gly | Ser | Ile | Thr | Pro | Ala | Gly | Gln | Gly | Ser | Arg | Leu | Gly | Ser |   |
|   |   |   | 260 |   |   |   |   | 265 |   |   |   |   | 270 |   |   |   |
| Gly | Ala | Leu | Thr | Pro | Asp | Gly | Ser | Lys | Leu | Thr | Ser | Gly | Val | Val | Thr |   |
|   |   | 275 |   |   |   |   | 280 |   |   |   |   | 285 |   |   |   |   |
| Pro | Asn | Gly | Ala | Glu | Thr | Val | Ile | Arg | Met | Ser | Tyr | Gly | Asn | Leu | Thr |   |
|   | 290 |   |   |   |   | 295 |   |   |   |   | 300 |   |   |   |   |   |
| Pro | Leu | Glu | Gly | Ser | Leu | Leu | Asp | Ser | Gln | Ile | Ser | Glu | Val | Ala | Ser |   |
| 305 |   |   |   |   | 310 |   |   |   |   | 315 |   |   |   |   | 320 |   |
| Leu | Ala | Asn | Ser | Asp | His | Gly | Ser | Ser | Arg | His | Asn | Asp | Glu | Ala | Leu |   |
|   |   |   |   | 325 |   |   |   |   | 330 |   |   |   |   | 335 |   |   |
| Val | Val | Pro | His | Arg | Val | Ser | Phe | Glu | Leu | Thr | Gly | Glu | Asp | Val | Ala |   |
|   |   |   | 340 |   |   |   |   | 345 |   |   |   |   | 350 |   |   |   |
| Arg | Cys | Leu | Ala | Ser | Lys | Leu | Asn | Arg | Ser | Gly | Ser | His | Glu | Lys | Ala |   |
|   |   |   | 355 |   |   |   |   | 360 |   |   |   |   | 365 |   |   |   |
| Ser | Gly | Glu | His | Leu | Arg | Pro | Asn | Cys | Cys | Lys | Thr | Ser | Gly | Glu | Thr |   |
|   | 370 |   |   |   |   | 375 |   |   |   |   | 380 |   |   |   |   |   |
| Glu | Ser | Glu | Gln | Ser | Gln | Lys | Leu | Arg | Ser | Phe | Ser | Thr | Gly | Ser | Asn |   |
| 385 |   |   |   |   | 390 |   |   |   |   | 395 |   |   |   |   | 400 |   |
| Lys | Glu | Phe | Lys | Phe | Asp | Ser | Thr | Asn | Glu | Glu | Met | Ile | Glu | Lys | Ile |   |
|   |   |   |   | 405 |   |   |   |   | 410 |   |   |   |   | 415 |   |   |
| Arg | Ser | Glu | Trp | Trp | Ala | Asn | Glu | Lys | Val | Ala | Gly | Lys | Gly | Asp | His |   |
|   |   |   | 420 |   |   |   |   | 425 |   |   |   |   | 430 |   |   |   |
| Ser | Pro | Arg | Asn | Ser | Trp | Thr | Phe | Phe | Pro | Val | Leu | Arg | Ser | Gly | His |   |
|   |   | 435 |   |   |   |   | 440 |   |   |   |   | 445 |   |   |   |   |
| Thr |   |   |   |   |   |   |   |   |   |   |   |   |   |   |   |   |

<210> SEQ ID NO 26
<211> LENGTH: 1947
<212> TYPE: DNA
<213> ORGANISM: Arabidopsis thaliana
<220> FEATURE:
<221> NAME/KEY: CDS
<222> LOCATION: (374)..(1669)

<400> SEQUENCE: 26
attctgatta aaatagaaat gcttttttcct tggtaaggat catctttca tgccgattgc    60

```
atcagtgcag atttccttat ttactctttc tcttctcaaa tttccatttt tttctttatc    120
tctcccactc ccactcataa aattagtttt gtctttcttt ccccaaaaat ctttacttaa    180 aatcttttc acccttttgc tttaactttt gtttgctcct cctctggatc gtatcagtaa    240
actggaagaa gaaattgtga gaaaaaatgg agaaaaccaa gatgattacg tctatgacct    300
gttgaagaaa ccctactcag aataagagta aaactctgtg attttctga ctaacagaga    360 gagagacacc taa atg ggc tca gag cag gat cag agg aaa agg tgg gga      409
            Met Gly Ser Glu Gln Asp Gln Arg Lys Arg Trp Gly
             1               5                  10 ggt tgt tta gga gtg ttc tct tgt ttc aag tca caa aaa ggt gga aaa     457
Gly Cys Leu Gly Val Phe Ser Cys Phe Lys Ser Gln Lys Gly Gly Lys
         15                  20                  25 aga att gta cct gct tct cgc att cct gaa ggt ggc aat gtc tca gct    505
Arg Ile Val Pro Ala Ser Arg Ile Pro Glu Gly Gly Asn Val Ser Ala
     30                  35                  40 tca caa cct aat gga gct cat caa gct ggt gtc tta aat aat caa gct    553
Ser Gln Pro Asn Gly Ala His Gln Ala Gly Val Leu Asn Asn Gln Ala
 45                  50                  55                  60 gca gga ggg att aat cta tca cta ttg gct cca cct tcc tct cct gct    601
Ala Gly Gly Ile Asn Leu Ser Leu Leu Ala Pro Pro Ser Ser Pro Ala
                 65                  70                  75 tcc ttc acc aat tca gct ctt cct tca act act cag tct cca aac tgc    649
Ser Phe Thr Asn Ser Ala Leu Pro Ser Thr Thr Gln Ser Pro Asn Cys
             80                  85                  90 tac tta tct ctg gct gca aat tca ccg gga ggt cct tcg tcg agt atg    697
Tyr Leu Ser Leu Ala Ala Asn Ser Pro Gly Gly Pro Ser Ser Ser Met
         95                  100                 105 tat gcc act gga cca tat gct cat gaa acc caa tta gtc tca ccg cct    745
Tyr Ala Thr Gly Pro Tyr Ala His Glu Thr Gln Leu Val Ser Pro Pro
     110                 115                 120 gtt ttc tct act ttc acc acc gag cca tcg act gct cct ttc act cct    793
Val Phe Ser Thr Phe Thr Thr Glu Pro Ser Thr Ala Pro Phe Thr Pro
125                 130                 135                 140 cct cca gag ctt gca cgt ctg act gcc cct tct tca cct gat gta cct    841
Pro Pro Glu Leu Ala Arg Leu Thr Ala Pro Ser Ser Pro Asp Val Pro
                145                 150                 155 tat gct cgt ttc ttg act tcc tcc atg gat ctc aag aac tct ggt aaa    889
Tyr Ala Arg Phe Leu Thr Ser Ser Met Asp Leu Lys Asn Ser Gly Lys
            160                 165                 170 ggt cat tac aat gat ctt caa gct act tat tct ctt tat ccc gga agt    937
Gly His Tyr Asn Asp Leu Gln Ala Thr Tyr Ser Leu Tyr Pro Gly Ser
        175                 180                 185 cca gcc agt gct ctt aga tca cca atc tct cgg gct tcg gga gat ggg    985
Pro Ala Ser Ala Leu Arg Ser Pro Ile Ser Arg Ala Ser Gly Asp Gly
    190                 195                 200 tta ttg tcg cct caa aat ggt aaa tgc tca agg agt gat tct ggc aac    1033
Leu Leu Ser Pro Gln Asn Gly Lys Cys Ser Arg Ser Asp Ser Gly Asn
205                 210                 215                 220 aca ttc ggg tat gac aca aat gga gtc tca aca cct ttg cag gag tca    1081
Thr Phe Gly Tyr Asp Thr Asn Gly Val Ser Thr Pro Leu Gln Glu Ser
                225                 230                 235 aac ttc ttc tgt cct gaa act ttt gcc aag ttt tac ctg gat cac gac    1129
Asn Phe Phe Cys Pro Glu Thr Phe Ala Lys Phe Tyr Leu Asp His Asp
            240                 245                 250 cct tca gtt cct caa aac ggt gga aga tta agc gtg tcg aag gat tca    1177
Pro Ser Val Pro Gln Asn Gly Gly Arg Leu Ser Val Ser Lys Asp Ser
        255                 260                 265
```

| | | | | | | | | | | | | | | | | |
|---|---|---|---|---|---|---|---|---|---|---|---|---|---|---|---|---|
| gat | gtg | tat | cct | aca | aat | gga | tat | gga | aac | ggg | aac | cag | aat | agg | cag | 1225 |
| Asp | Val | Tyr | Pro | Thr | Asn | Gly | Tyr | Gly | Asn | Gly | Asn | Gln | Asn | Arg | Gln | |
| | 270 | | | | 275 | | | | | 280 | | | | | | |

| | | | | | | | | | | | | | | | | |
|---|---|---|---|---|---|---|---|---|---|---|---|---|---|---|---|---|
| aac | aga | agt | ccc | aag | caa | gac | atg | gag | gag | tta | gaa | gct | tac | agg | gcg | 1273 |
| Asn | Arg | Ser | Pro | Lys | Gln | Asp | Met | Glu | Glu | Leu | Glu | Ala | Tyr | Arg | Ala | |
| 285 | | | | | 290 | | | | | 295 | | | | | 300 | |

| | | | | | | | | | | | | | | | | |
|---|---|---|---|---|---|---|---|---|---|---|---|---|---|---|---|---|
| tcc | ttt | ggt | ttt | agt | gca | gat | gaa | atc | atc | aca | act | agt | cag | tat | gta | 1321 |
| Ser | Phe | Gly | Phe | Ser | Ala | Asp | Glu | Ile | Ile | Thr | Thr | Ser | Gln | Tyr | Val | |
| | | | | 305 | | | | | 310 | | | | | 315 | | |

| | | | | | | | | | | | | | | | | |
|---|---|---|---|---|---|---|---|---|---|---|---|---|---|---|---|---|
| gag | atc | act | gat | gtg | atg | gat | ggg | tct | ttt | aac | aca | tca | gct | tac | tct | 1369 |
| Glu | Ile | Thr | Asp | Val | Met | Asp | Gly | Ser | Phe | Asn | Thr | Ser | Ala | Tyr | Ser | |
| | | | 320 | | | | | 325 | | | | | 330 | | | |

| | | | | | | | | | | | | | | | | |
|---|---|---|---|---|---|---|---|---|---|---|---|---|---|---|---|---|
| cca | agc | gat | gga | caa | aag | ctt | ctc | aga | aga | gaa | gca | aat | ttg | ctg | agt | 1417 |
| Pro | Ser | Asp | Gly | Gln | Lys | Leu | Leu | Arg | Arg | Glu | Ala | Asn | Leu | Leu | Ser | |
| | | 335 | | | | | 340 | | | | | 345 | | | | |

| | | | | | | | | | | | | | | | | |
|---|---|---|---|---|---|---|---|---|---|---|---|---|---|---|---|---|
| caa | aca | agc | ccc | aaa | tca | gaa | gcc | gat | ctt | gat | tca | caa | gtt | gta | gac | 1465 |
| Gln | Thr | Ser | Pro | Lys | Ser | Glu | Ala | Asp | Leu | Asp | Ser | Gln | Val | Val | Asp | |
| | 350 | | | | | 355 | | | | | 360 | | | | | |

| | | | | | | | | | | | | | | | | |
|---|---|---|---|---|---|---|---|---|---|---|---|---|---|---|---|---|
| ttc | caa | tca | cca | aag | tca | tca | aat | agc | tac | aaa | gat | cac | aaa | caa | aga | 1513 |
| Phe | Gln | Ser | Pro | Lys | Ser | Ser | Asn | Ser | Tyr | Lys | Asp | His | Lys | Gln | Arg | |
| 365 | | | | | 370 | | | | | 375 | | | | | 380 | |

| | | | | | | | | | | | | | | | | |
|---|---|---|---|---|---|---|---|---|---|---|---|---|---|---|---|---|
| aac | cgg | atc | cat | gcg | gat | gaa | gag | gct | tta | ttg | tcg | aga | gtg | ggg | tct | 1561 |
| Asn | Arg | Ile | His | Ala | Asp | Glu | Glu | Ala | Leu | Leu | Ser | Arg | Val | Gly | Ser | |
| | | | | 385 | | | | | 390 | | | | | 395 | | |

| | | | | | | | | | | | | | | | | |
|---|---|---|---|---|---|---|---|---|---|---|---|---|---|---|---|---|
| gta | aaa | gga | agc | aga | agc | tat | cat | att | tca | agc | tct | gat | gca | gag | gtc | 1609 |
| Val | Lys | Gly | Ser | Arg | Ser | Tyr | His | Ile | Ser | Ser | Ser | Asp | Ala | Glu | Val | |
| | | | 400 | | | | | 405 | | | | | 410 | | | |

| | | | | | | | | | | | | | | | | |
|---|---|---|---|---|---|---|---|---|---|---|---|---|---|---|---|---|
| gag | tac | aga | aga | gga | aga | agc | tta | agg | gaa | agc | aga | gag | aac | aga | cac | 1657 |
| Glu | Tyr | Arg | Arg | Gly | Arg | Ser | Leu | Arg | Glu | Ser | Arg | Glu | Asn | Arg | His | |
| | | 415 | | | | | 420 | | | | | 425 | | | | |

| | | | | | |
|---|---|---|---|---|---|
| agg | aaa | gcc | tga | tcaagaacaa caacaacaag aagaagaaag cctgatctgt | 1709 |
| Arg | Lys | Ala | | | |
| | 430 | | | | | tcttaaagtc ttctaaggtc taaaaagttg atcttgtgat gctaactctt gagataagaa    1769 gtctagtttt taagtatata tagatatata taaatataat tacagatggt tttttagtag    1829 aatgatgtta tatataagaa gagagcaagg gtgagaaagt gaatgcttgt tttttagttt    1889 gacatggctt ttttgtaaga ccccatcttt tatctaattg caccaatctg tttgagct      1947

<210> SEQ ID NO 27
<211> LENGTH: 431
<212> TYPE: PRT
<213> ORGANISM: Arabidopsis thaliana
<400> SEQUENCE: 27

Met Gly Ser Glu Gln Asp Gln Arg Lys Arg Trp Gly Gly Cys Leu Gly
1               5                   10                  15

Val Phe Ser Cys Phe Lys Ser Gln Lys Gly Gly Lys Arg Ile Val Pro
            20                  25                  30

Ala Ser Arg Ile Pro Glu Gly Gly Asn Val Ser Ala Ser Gln Pro Asn
        35                  40                  45

Gly Ala His Gln Ala Gly Val Leu Asn Asn Gln Ala Ala Gly Gly Ile
    50                  55                  60

Asn Leu Ser Leu Leu Ala Pro Pro Ser Ser Ala Ser Phe Thr Asn
65                  70                  75                  80

Ser Ala Leu Pro Ser Thr Thr Gln Ser Pro Asn Cys Tyr Leu Ser Leu
                85                  90                  95

Ala Ala Asn Ser Pro Gly Gly Pro Ser Ser Ser Met Tyr Ala Thr Gly

```
                100               105                  110
    Pro Tyr Ala His Glu Thr Gln Leu Val Ser Pro Val Phe Ser Thr
                    115                 120                 125
    Phe Thr Thr Glu Pro Ser Thr Ala Pro Phe Thr Pro Pro Glu Leu
    130                 135                 140
    Ala Arg Leu Thr Ala Pro Ser Ser Pro Asp Val Pro Tyr Ala Arg Phe
    145                 150                 155                 160
    Leu Thr Ser Ser Met Asp Leu Lys Asn Ser Gly Lys Gly His Tyr Asn
                    165                 170                 175
    Asp Leu Gln Ala Thr Tyr Ser Leu Tyr Pro Gly Ser Pro Ala Ser Ala
                    180                 185                 190
    Leu Arg Ser Pro Ile Ser Arg Ala Ser Gly Asp Gly Leu Leu Ser Pro
                    195                 200                 205
    Gln Asn Gly Lys Cys Ser Arg Ser Asp Ser Gly Asn Thr Phe Gly Tyr
                    210                 215                 220
    Asp Thr Asn Gly Val Ser Thr Pro Leu Gln Glu Ser Asn Phe Cys
    225                 230                 235                 240
    Pro Glu Thr Phe Ala Lys Phe Tyr Leu Asp His Asp Pro Ser Val Pro
                    245                 250                 255
    Gln Asn Gly Gly Arg Leu Ser Val Ser Lys Asp Ser Asp Val Tyr Pro
                    260                 265                 270
    Thr Asn Gly Tyr Gly Asn Gly Asn Gln Asn Arg Gln Asn Arg Ser Pro
                    275                 280                 285
    Lys Gln Asp Met Glu Glu Leu Glu Ala Tyr Arg Ala Ser Phe Gly Phe
                    290                 295                 300
    Ser Ala Asp Glu Ile Ile Thr Thr Ser Gln Tyr Val Glu Ile Thr Asp
    305                 310                 315                 320
    Val Met Asp Gly Ser Phe Asn Thr Ser Ala Tyr Ser Pro Ser Asp Gly
                    325                 330                 335
    Gln Lys Leu Leu Arg Arg Glu Ala Asn Leu Leu Ser Gln Thr Ser Pro
                    340                 345                 350
    Lys Ser Glu Ala Asp Leu Asp Ser Gln Val Val Asp Phe Gln Ser Pro
                    355                 360                 365
    Lys Ser Ser Asn Ser Tyr Lys Asp His Lys Gln Arg Asn Arg Ile His
                    370                 375                 380
    Ala Asp Glu Glu Ala Leu Leu Ser Arg Val Gly Ser Val Lys Gly Ser
    385                 390                 395                 400
    Arg Ser Tyr His Ile Ser Ser Ser Asp Ala Glu Val Glu Tyr Arg Arg
                    405                 410                 415
    Gly Arg Ser Leu Arg Glu Ser Arg Glu Asn Arg His Arg Lys Ala
                    420                 425                 430

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
ggaagttcat ttattcggag ag                                          22

<210> SEQ ID NO 29
<211> LENGTH: 22
<212> TYPE: DNA
<213> ORGANISM: Artificial Sequence
```

```
<220> FEATURE:
<223> OTHER INFORMATION: primer

<400> SEQUENCE: 29
ggcaacagga ttcaatctta ag                                              22

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
cgccatccaa gctgttctc                                                  19

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tcacgtccag caaggtcaag                                                 20

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
cattcgtctc tcgggtcca                                                  19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
tcttcggcga agctgatcta                                                 20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
cgagaaaatt ctcagactca                                                 20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
aagcagctgc gtttatagta                                                 20
```

```
<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ggtggtttct gagtagtagt                                              20

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
agtctcaacg ctgttatta                                               19

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gttatttgat tgtcgtcgtt                                              20

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ttctagactc agcggagac                                               19

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ctgttgaaga aaccctactc                                              20

<210> SEQ ID NO 41
<211> LENGTH: 18
<212> TYPE: DNA
<213> ORGANISM: Artificial Sequence
<220> FEATURE:
<223> OTHER INFORMATION: primer

<400> SEQUENCE: 41
accttttcct ctgatcct                                                18

<210> SEQ ID NO 42
<211> LENGTH: 24
<212> TYPE: DNA
<213> ORGANISM: Artificial Sequence
<220> FEATURE:
<223> OTHER INFORMATION: primer
```

```
<400> SEQUENCE: 42
caccatgaga agcggtgcta atgg                                              24

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
ttagcttagt gtacctgact g                                                 21

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
caccatgcag agtgggagcg agat                                              24

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45
ttagctgacc cctggctgt                                                    19

<210> SEQ ID NO 46
<211> LENGTH: 39
<212> TYPE: DNA
<213> ORGANISM: Artificial Sequence
<220> FEATURE:
<223> OTHER INFORMATION: primer

<400> SEQUENCE: 46
aggatttatc acaagtttgt acaaaaaagc aggctccgc                              39

<210> SEQ ID NO 47
<211> LENGTH: 40
<212> TYPE: DNA
<213> ORGANISM: Artificial Sequence
<220> FEATURE:
<223> OTHER INFORMATION: primer

<400> SEQUENCE: 47
gtttggtgtt actcctgcag gatttatcac aagtttgtac                             40

<210> SEQ ID NO 48
<211> LENGTH: 63
<212> TYPE: DNA
<213> ORGANISM: Artificial Sequence
<220> FEATURE:
<223> OTHER INFORMATION: primer

<400> SEQUENCE: 48
caccactttg tacaagaaag ctgggtcggc gcgcccaccc ttttagctta gtgtacctga       60
ctg                                                                     63
```

```
<210> SEQ ID NO 49
<211> LENGTH: 54
<212> TYPE: DNA
<213> ORGANISM: Artificial Sequence
<220> FEATURE:
<223> OTHER INFORMATION: primer

<400> SEQUENCE: 49
ggccgatttg gcccctgcag gatttatcac cactttgtac aagaaagctg ggtc            54
```

GENE FOR INCREASING PLANT BIOMASS AND USE THEREFOR

CROSS-REFERENCE TO RELATED APPLICATIONS

This application is a Continuation of application Ser. No. 15/517,861, filed on Apr. 7, 2017, which is the National Phase under 35 U.S.C. § 371 of International Application No. PCT/JP2015/078754, filed on Oct. 9, 2015, which claims the benefit under 35 U.S.C. § 119(a) to Patent Application No. 2014-209154, filed in Japan on Oct. 10, 2014, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2020_03_30 Sequence_Listing_0230_0343PUS2" created on Mar. 30, 2020 and is 188,408 bytes in size. The sequence listing contained in this .txt file is part of the specification and is hereby incorporated by reference herein in its entirety.

TECHNICAL FIELD

The present invention relates to a novel gene for increasing plant biomass, and more particularly to, for example, a plant having said gene introduced therein, a method for increasing plant biomass using said gene, and a method for preparing a plant with increased biomass using said gene.

BACKGROUND ART

Biomass is generally understood to refer to the amount of a living biological organism ("bio") present in a given space at a particular point of time, as expressed as the amount of substance ("mass"). Biomass may be expressed as "seibut-sutairyou" or "seibutsuryou" in Japanese, and may be called "standing crop" in ecology. Biomass is commonly quantified by mass or amount of energy, and may be expressed as the dry weight of a living biological organism per unit area. In many cases, plants are used to create biomass, and increasing plant biomass is considered useful not only for providing biofuels or renewable energies but also for stabilizing food supply through increased crop yields.

As for increase in plant biomass, various techniques have conventionally been adopted to develop a new, industrially useful plant variety, such as a hybridization breeding method in which different plants are crossed to select a superior progeny, and a mutation breeding method which induces mutation in a plant. In recent years, there have been developed genetically modified plants in which a useful gene is introduced to exhibit its function. For the purpose of developing such a new plant variety, a method for assembling genes that can impart superior characters is effective, but under the circumstances where further improvement in crop productivity is needed, only limited types of genes are available at present, and there is a desire to identify genes involved in increased biomass, particularly in high-yielding character.

Promotion of plant growth is in many cases influenced by plant hormones, and brassinosteroids are known examples of the plant hormones. Brassinosteroids are a group of compounds having a steroid backbone and typified by brassinolide. Brassinosteroids have the following activities related to plant growth: (i) promotion of the elongation and growth of stems, leaves and roots; (ii) promotion of cell division; (iii) promotion of differentiation of mesophyll cells into ducts or tracheids; (iv) promotion of ethylene synthesis; (v) promotion of seed germination; and (vi) imparting of resistance to environmental stress. There has been an attempt to increase the yield of *Oryza sativa* by utilizing the aforementioned physiological activities of brassinosteroids and introducing a brassinosteroid biosynthesis gene into *O. sativa* (Non-Patent Literature 1). However, the effects of this attempt are not necessarily satisfactory. Hitherto, a certain number of genes involved in the synthesis and signaling of brassinosteroids have been identified, but no gene has been identified which can fully achieve increased plant biomass.

CITATION LIST

Non-Patent Literatures

Non-Patent Literature 1: Chuan-yin Wu, et al., *The Plant Cell,* 2008, 20(8):2130-2145

SUMMARY

Technical Problem

As mentioned above, search for genes capable of increasing plant biomass, esp., genes capable of increasing seed yield, has not yet been conducted thoroughly. Thus, there has been a strong demand to find a novel gene capable of effectively increasing plant biomass and to develop a technique that utilizes said gene, for example, to develop a plant with increased biomass using said gene.

The present invention has been made in view of the aforementioned problems, and has as its object to identify a novel gene capable of effectively increasing plant biomass and provide said gene as well as a technique that utilizes said gene.

Solution to Problem

The present inventors attempted to screen for *Arabidopsis thaliana* mutants and isolate related genes using, as a selection criterion, the morphology of hypocotyl during germination in the presence of the brassinosteroid biosynthesis inhibitor brassinazole (Brz) and in the dark. To be specific, the inventors screened for *Arabidopsis thaliana* mutants and searched for related genes using the method based on FOX Hunting System (Full-length cDNA Overexpression Gene Hunting System). As a result, the inventors discovered a mutant with extremely strong brassinazole resistance and performed genetic analysis of said mutant, which revealed that the bil7 (Brz-insensitive-long-hypocotyl 7) gene is involved in this mutation.

The inventors further prepared a construct expressing the bil7 gene and introduced said construct to a plant to generate a transformant overexpressing the bil7 gene. The inventors examined the morphological characters of said transformant, and found that as compared to a wild plant, the growth of said transformant is promoted in terms of various factors including inflorescence length. Based on these findings, the inventors have completed the invention.

The present invention is preferably carried out by, but not limited to, the following embodiments.

Embodiment 1

A plant having introduced therein a nucleic acid encoding a protein, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass.

Embodiment 2

The plant according to embodiment 1, wherein the amino acid sequence of SEQ ID NO:1 is the amino acid sequence of SEQ ID NO:2.

Embodiment 3

The plant according to embodiment 1 or 2, wherein the protein comprises the amino acid sequence of any of SEQ ID NOs:3 to 5.

Embodiment 4

The plant according to any one of embodiments 1 to 3, wherein the nucleic acid is a nucleic acid derived from a monocotyledonous plant or a dicotyledonous plant, and wherein the plant is a monocotyledonous plant.

Embodiment 5

A method for increasing plant biomass, comprising the step of introducing a nucleic acid encoding a protein into a plant, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass.

Embodiment 6

The method according to embodiment 5, wherein the amino acid sequence of SEQ ID NO:1 is the amino acid sequence of SEQ ID NO:2.

Embodiment 7

The method according to embodiment 5 or 6, wherein the protein comprises the amino acid sequence of any of SEQ ID NOs:3 to 5.

Embodiment 8

The method according to any one of embodiments 5 to 7, wherein the nucleic acid is a nucleic acid derived from a monocotyledonous plant or a dicotyledonous plant, and wherein the plant is a monocotyledonous plant.

Embodiment 9

A method for preparing a plant with increased biomass, comprising the step of introducing a nucleic acid encoding a protein into a plant, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass.

Embodiment 10

The method according to embodiment 9, wherein the amino acid sequence of SEQ ID NO:1 is the amino acid sequence of SEQ ID NO:2.

Embodiment 11

The method according to embodiment 9 or 10, wherein the protein comprises the amino acid sequence of any of SEQ ID NOs:3 to 5.

Embodiment 12

The method according to any one of embodiments 9 to 11, wherein the nucleic acid is a nucleic acid derived from a monocotyledonous plant or a dicotyledonous plant, and wherein the plant is a monocotyledonous plant.

Embodiment 13

A construct comprising a nucleic acid encoding a protein and a promoter, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass.

Embodiment 14

The construct according to embodiment 13, wherein the amino acid sequence of SEQ ID NO:1 is the amino acid sequence of SEQ ID NO:2.

Embodiment 15

The construct according to embodiment 13 or 14, wherein the protein comprises the amino acid sequence of any of SEQ ID NOs:3 to 5.

Embodiment 16

A vector comprising the construct according to any one of embodiments 13 to 15.

Embodiment 17

A host cell comprising the vector according to embodiment 16.

Embodiment 18

A plant having introduced therein the vector according to embodiment 17.

Embodiment 19

The plant according to embodiment 18, wherein the nucleic acid is a nucleic acid derived from a monocotyledonous plant or a dicotyledonous plant, and wherein the plant is a monocotyledonous plant.

Embodiment 20

A method for screening for a plant with increased biomass, comprising the steps of:
(1) measuring the expression levels of a protein or a nucleic acid encoding the protein in test and wild-type plants, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass;
(2) comparing the expression levels obtained at step (1); and
(3) selecting the test plant whose expression level is higher than that in the wild-type plant.

Embodiment 21

The method according to embodiment 20, wherein the amino acid sequence of SEQ ID NO:1 is the amino acid sequence of SEQ ID NO:2.

Embodiment 22

The method according to embodiment 20 or 21, wherein the protein comprises the amino acid sequence of any of SEQ ID NOs:3 to 5.

Embodiment 23

The method according to any one of embodiments 20 to 22, wherein the nucleic acid is a nucleic acid derived from a monocotyledonous plant or a dicotyledonous plant, and wherein the plant is a monocotyledonous plant.

Embodiment 24

A method for verifying a plant with increased biomass, comprising the steps of:
(1) measuring the expression levels of a protein or a nucleic acid encoding the protein in test and wild-type plants, wherein the protein comprises:
the amino acid sequence of SEQ ID NO:1, and
an amino acid sequence having at least 25% identity or at least 75% similarity to the amino acid sequence of SEQ ID NO:7 or 11, and
has an activity to increase plant biomass;
(2) comparing the expression levels obtained at step (1); and
(3) confirming that the expression level in the test plant is higher than that in the wild-type plant.

Embodiment 25

The method according to embodiment 24, wherein the amino acid sequence of SEQ ID NO:1 is the amino acid sequence of SEQ ID NO:2.

Embodiment 26

The method according to embodiment 24 or 25, wherein the protein comprises the amino acid sequence of any of SEQ ID NOs:3 to 5.

Embodiment 27

The method according to any one of embodiments 24 to 26, wherein the nucleic acid is a nucleic acid derived from a monocotyledonous plant or a dicotyledonous plant, and wherein the plant is a monocotyledonous plant.

Advantageous Effects of Invention

According to the present invention, plant biomass can be effectively increased. Also, by using this invention, there can be provided a plant with effectively increased biomass and a method for preparing said plant, as well as a useful means for screening for a plant with increased biomass, and a method for screening for a substance that increases plant biomass.

BRIEF DESCRIPTIONS OF DRAWINGS

FIG. 1 shows the brassinazole (Brz) resistance of bil7-1D in the dark. It is evident from this figure that bil7-1D exhibits Brz resistance during germination in the dark. Panel A shows the status of hypocotyl elongation in different plants on day 7 in the dark in the presence of 0, 0.3, 1 or 3 µM Brz. Panel B shows the elongation length of hypocotyls of different plants on day 7 in the dark in the presence of 0, 0.3, 1 or 3 µM Brz. Panel C shows the elongation rate of hypocotyls of different plants on day 7 in the dark in the presence of 0, 0.3, 1 or 3 µM Brz. Scale bar=3 mm; Error bar=S.D.; n=30; ***: $P<0.001$; Student t test relative to 0 µM Brz.

FIG. 2 shows the morphological features of bil7-1D. It is evident from this figure that bil7-1D exhibits growth-promoting morphological characters. Panel A shows the status of different plants on day 60 (Scale bar=10 cm). Panel B shows the shape of rosette leaves of different plants on day 40 (Scale bar=1 cm). Panel C shows the length of inflorescences of different plants on day 70 (n=12). Panel D shows the number of inflorescences in different plants on day 70 (n=12). Panel E shows the number of secondary inflorescences in different plants on day 70 (n=12). Error bar=S.D.; ***: $P<0.001$; Student t test relative to WT.

FIG. 3 shows the morphological features of the petals, siliques and seeds of bil7-1D. It is evident from this figure that bil7-1D exhibits an increase in seed weight. Panel A shows the normal flowering (left) and abnormal flowering (right) behaviors of bil7-1D (Scale bar=1 mm). Panel B shows a silique of bil7-1D with normal flowering behavior (left) and a silique of bil7-1D with abnormal flowering behavior (right) (Scale bar=5 mm). Panel C shows the seeds of the wild-type (left) and the seeds of bil7-1D (right) (Scale bar=0.5 mm). Panel D shows the number of flowers in different plants on day 70 (n=12). Panel E shows the number of normal siliques in different plants on day 70 (n=12). Panel F shows the number of seeds per silique in different plants (n=12). Panel G shows the weight of 100 seeds of different plants (n=5). Error bar=S.D.; *: $P<0.1$; : $P<0.01$; *: $P<0.001$; Student t test relative to WT.

FIG. 4 shows the inflorescence elongation period and flowering period of bil7-1D. Panel A shows the number of rosette leaves in different plants during the flowering period (n=5). Panel B shows the number of days to flower for different plants (n=5). Panel C shows temporal change in inflorescence length for different plants, and their flowering periods (n=24). Error bar=S.D.; *: $P<0.1$; ***: $P<0.001$; Student t test relative to WT.

and a BIL7 expression-inhibited transformant (BIL7-RNAi) in the dark. It is evident from this figure that a plant line with higher BIL7 expression level exhibits more significant hypocotyl elongation during germination in the dark in the presence of Brz. Panel A shows the hypocotyls of different plants on day 7 in the dark in the presence of 3 µM Brz (Scale bar=3 mm). Panel B shows the length of hypocotyls of different plants on day 7 in the dark in the presence of 3 µM Brz (Error bar=S.D.; n=50; ***:P<0.001; Student t test relative to WT). Panel C shows the BIL7 expression level in different plant lines on day 27 (Error bar=S.D.). WT: wild-type; BIL7-OX1, 2: 35S::BIL7 overexpressor 1, 2; BIL7-RNAi: BIL7-RNAi suppressor.

Figure 7:
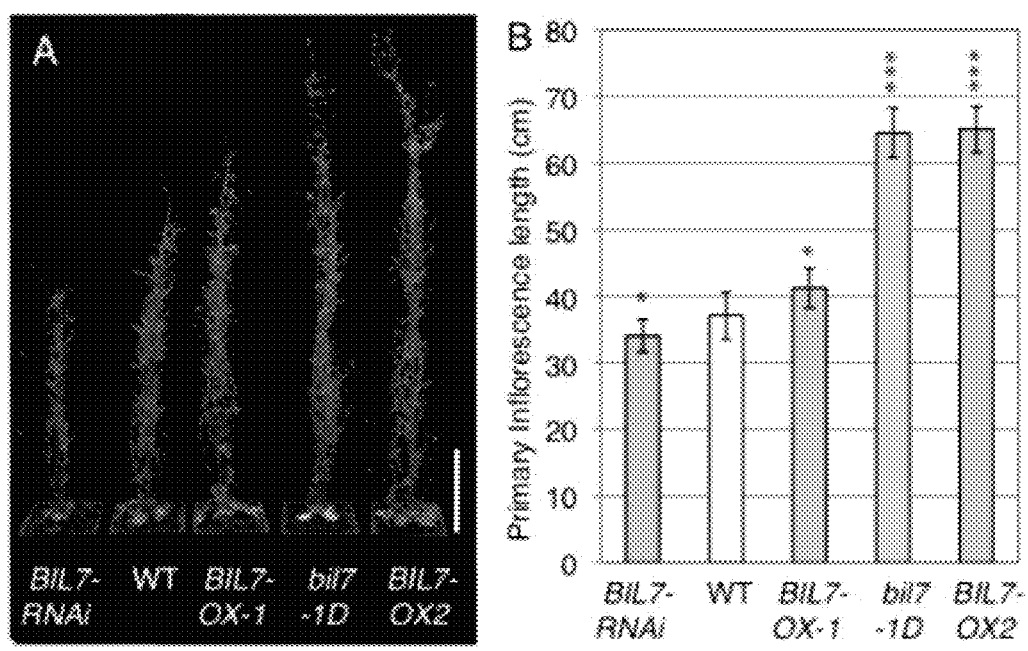

FIG. 7 shows the morphological features of BIL7-OX and BIL7-RNAi. It is evident from this figure that a plant line with higher BIL7 expression level exhibits more significant inflorescence elongation morphology during the maturity period. Panel A shows the status of different plants on day 63 (Scale bar=10 cm). Panel B shows the length of inflorescences of different plants on day 86 (n=10; Error bar=S.D.; *: P<0.1; ***: P<0.001; Student t test relative to WT). WT: wild-type; BIL7-OX1, 2: 35S::BIL7 overexpressor 1, 2; BIL7-RNAi: BIL7-RNAi suppressor.

Figure 8:
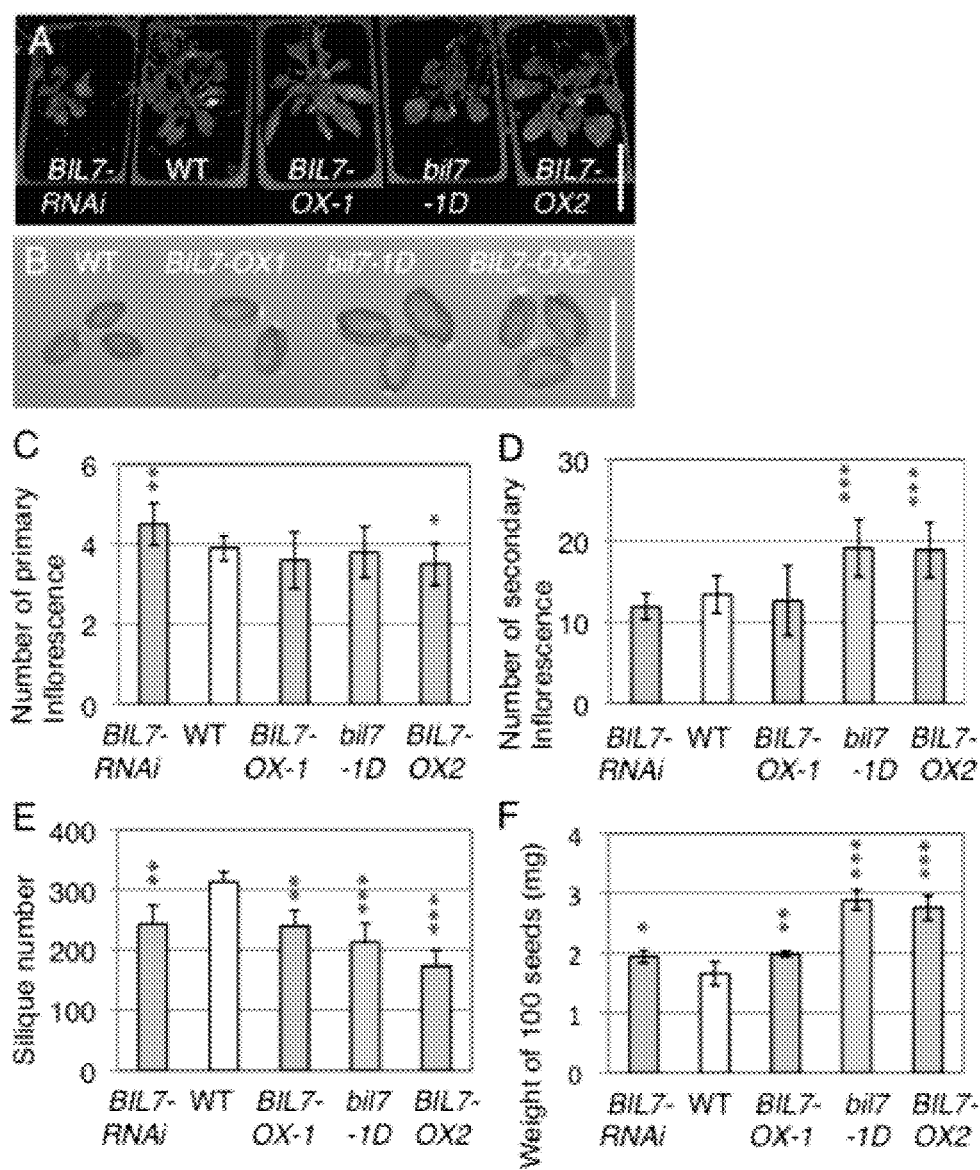

FIG. 8 shows the morphological features of BIL7-OX and BIL7-RNAi. It is evident from this figure that BIL7-OX tends to exhibit an increase in number of secondary inflorescences and seed weight. Panel A shows the shape of rosette leaves of different plants on day 72 (Scale bar=5 cm). Panel B shows the seeds of different plant lines (Scale bar=1 mm). Panel C shows the number of inflorescences in different plants on day 86 (n=10). Panel D shows the length of secondary inflorescences of different plants on day 86 (n=10). Panel E shows the number of normal siliques in different plants on day 86 (n=10). Panel F shows the weight of 100 seeds of different plants (n=5). Error bar=S.D.; *: P<0.1; : P<0.01; *: P<0.001; Student t test relative to WT; WT: wild-type; BIL7-OX1, 2: 35S::BIL7 overexpressor 1, 2; BIL7-RNAi: BIL7-RNAi suppressor.

Figure 9:
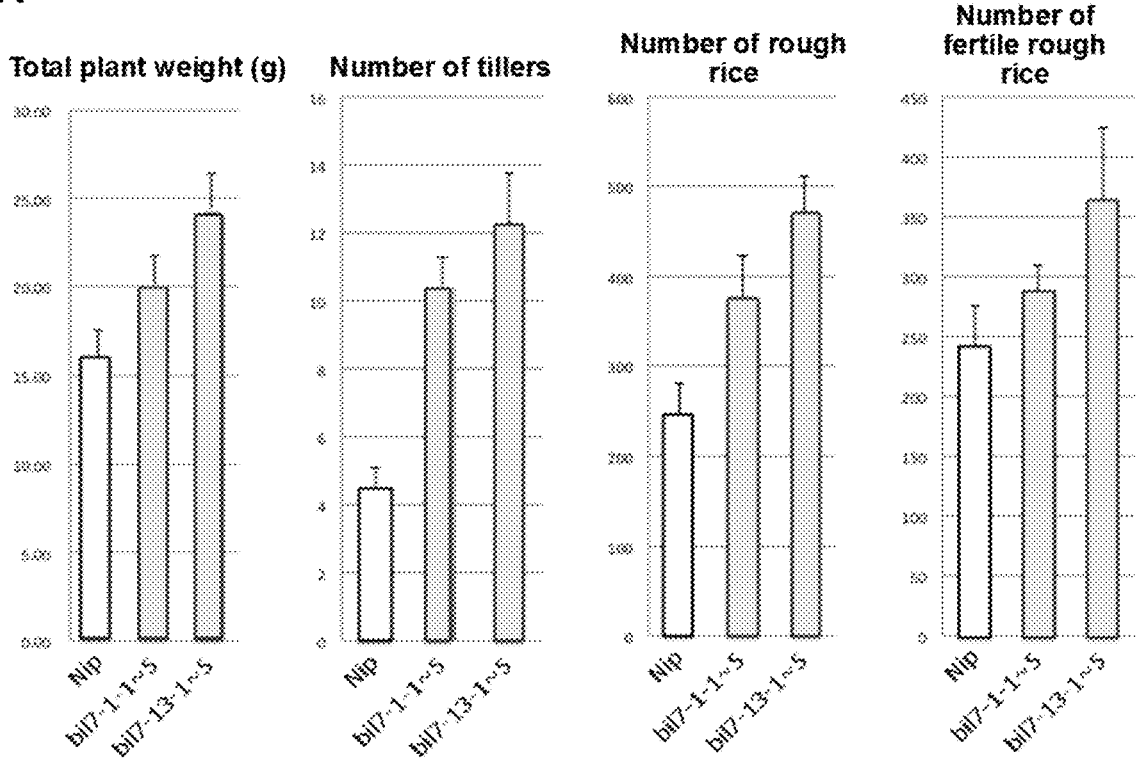
Figure 9:
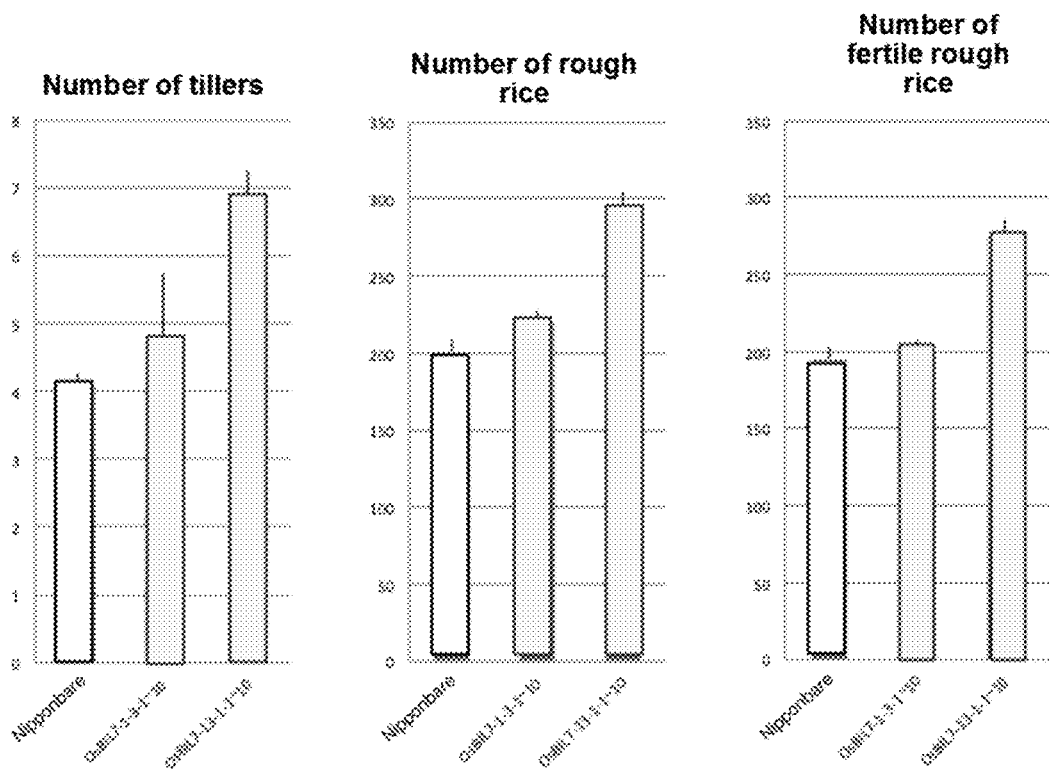

FIG. 9 shows increased biomass in a high OsBIL7-expressing transformant (OsBIL7-OX). Panel A shows the results for T1 generation plants. It is evident from this panel that the *O. sativa* strain OsBIL7-OX (T1 generation) in which the BIL7 homologous gene from *O. sativa*, OsBIL7, is highly expressed exhibits an increase in total plant weight, number of tillers, number of rough rice, and number of fertile rough rice (150%), as calculated per hill. Panel B shows the results for T2 generation plants. It is evident from this panel that the *O. sativa* strain OsBIL7-OX (T2 generation) in which the BIL7 homologous gene from *O. sativa*, OsBIL7, is highly expressed exhibits an increase in number of tillers, number of rough rice, and number of fertile rough rice (140%), as calculated per hill.

Figure 10:
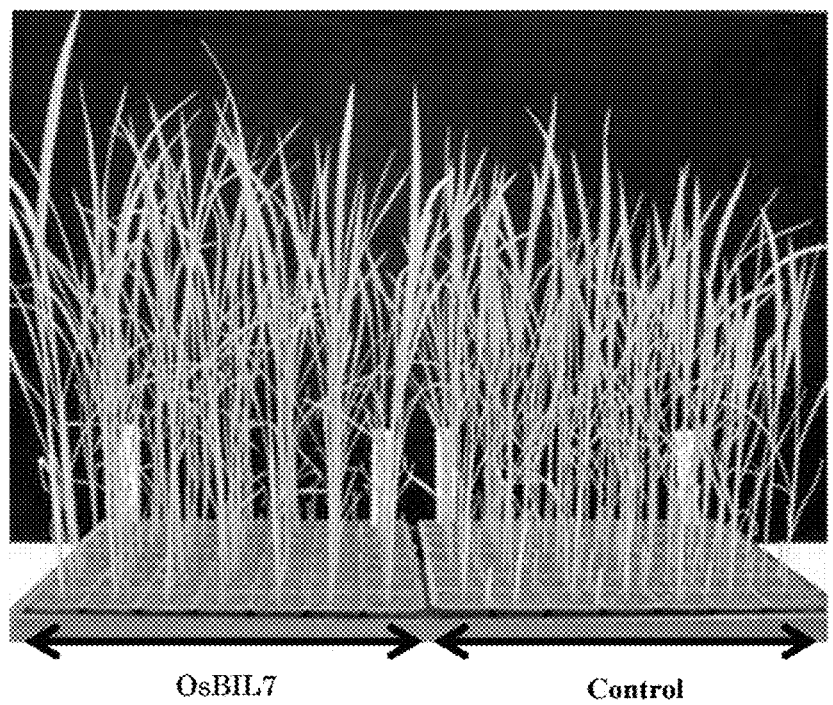

FIG. 10 shows the plant shape of OsBIL7 rice transformants after 17 days of transplantation to pots. It was observed that rice plants (variety Yukihikari) transformed with OsBIL7 (left) are more vigorous than those transformed with the control vector (right).

Figure 11:

FIG. 11 shows the plant shape of OsBIL7 rice transformants during the maturity period. It was observed that rice plant (variety Yukihikari) transformed with OsBIL7 (left) are more vigorous than those transformed with the control vector (right).

Figure 12:
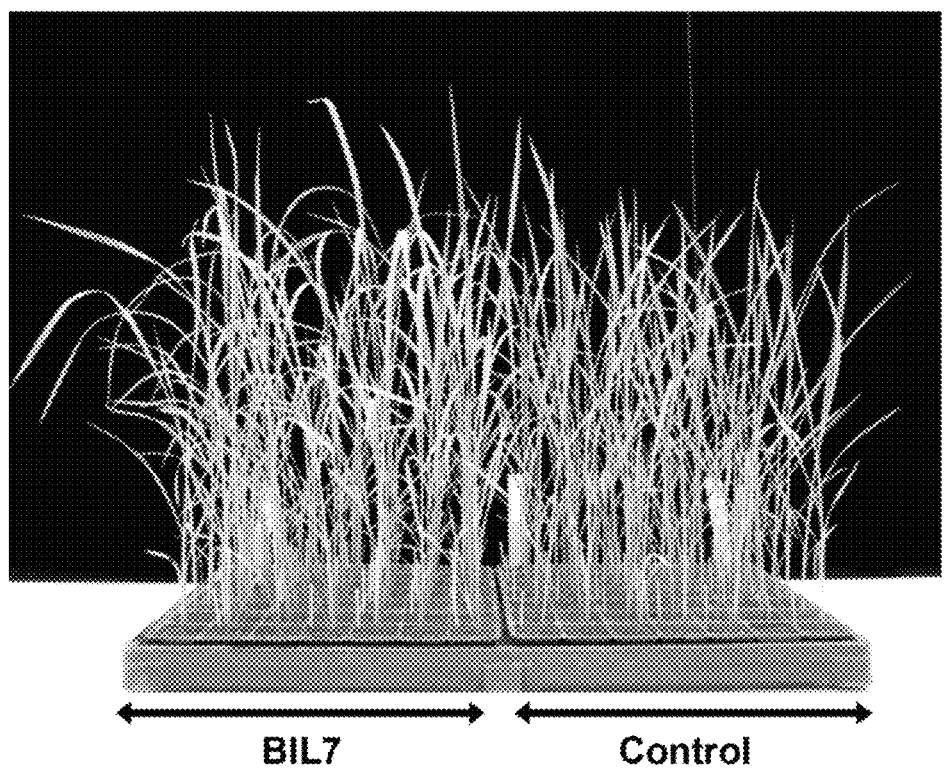

FIG. 12 shows the plant shape of BIL7 rice transformants after 17 days of transplantation to pots. It was observed that rice plants (variety Yukihikari) transformed with BIL7 (left) are more vigorous than those transformed with the control vector (right).

Figure 13:

FIG. 13 shows the plant shape of BIL7 rice transformants during the maturity period. It was observed that rice plants (variety Yukihikari) transformed with BIL7 (right) are more vigorous than those transformed with the control vector (left).

DESCRIPTION OF EMBODIMENTS (1) Nucleic Acid and Protein

In the present invention, the bil7 (Brz-insensitive-long-hypocotyl 7) gene is used as a nucleic acid that contributes to an increase in plant biomass. The bil7 gene is a gene that is involved in brassinosteroid signaling and which was discovered in a mutant whose hypocotyl elongates even in the presence of brassinazole (Brz), a brassinosteroid biosynthesis inhibitor; and this gene can be found in various species of plants. Although the nucleotide sequence of the bil7 gene and the amino acid sequence of a protein encoded by said gene (i.e., BIL7 protein) vary among different species of plants, the protein of the present invention has a common motif consisting of the amino acid sequence of SEQ ID NO:1 as shown below.

```
SEQ ID NO: 1:
Ala-Pro-Pro-Ser-Ser-Pro-Ala-Ser-X1-X2-X3-Ser-X4-

X5-X6-Ser-X7-X8-X9-X10-Pro-X11-Gly-Pro-Tyr-Ala-

X12-Glu-X13-X14-X15-Val-X16-Pro-Pro-Val-Phe-Ser-

X17-X18-X19-Thr-X20-Pro-Ser-X21-Ala-Pro-X22-Thr-

Pro-Pro-X23-Pro-Ser-Ser-Pro-X24-Val-Pro-X25-Ala-

X26-Pro-X27-Ser-Pro-X28-Ser-Pro
```

(where X1 represents Phe or Tyr; X2 represents Phe, Leu, Thr or Ala; X3 represents Gln, Pro, His or Asn; X4 represents Glu, Gly, Asp, Ala or Met; X5 represents Pro, Gly, Leu or Ala; X6 represents Pro, Ala, Thr or Ser; X7 represents Ala, Ile, Val, Ser, or Thr; X8 represents Thr, Val, Ser or Ala; X9 represents Gln or His; X10 represents Ser or Thr; X11 represents 15 to 30 amino acid residues; X12 represents His or Asn; X13 represents Thr or Pro; X14 represents Gln or Ala; X15 represents Leu or Pro; X16 represents Ser or Thr; X17 represents Thr or Ala; X18 represents Tyr or Phe; X19 represents Thr, Ile or Pro; X20 represents Glu or Ala; X21 represents Ser or Thr; X22 represents Ile, Val, Tyr or Phe; X23 represents 3 to 15 amino acid residues; X24 represents Glu or Asp; X25 represents Phe or Tyr; X26 represents 20 to 50 amino acid residues; X27 represents Gly, Glu or Asp; and X28 represents 5 or 6 amino acid residues.)

In the aforementioned amino acid sequence, X11 preferably represents 17 to 29 amino acid residues, more preferably 20 to 26 amino acid residues; X23 preferably represents 3 to 12 amino acid residues, more preferably 8 to 12 amino acid residues; X26 preferably represents 23 to 49 amino acid residues, more preferably 23 to 30 amino acid residues; and X28 preferably represents 5 amino acid residues.

The plant having BIL7 protein comprising the aforementioned common motif is not particularly limited, and can be exemplified by *Arabidopsis thaliana* (thale cress), *Glycine max* (soybean), *Oryza sativa* (rice), *Zea mays* (corn), *Raphanus sativus* (radish), *Populus trichocarpa* (poplar), *Vitis vinifera* (grape), and *Physcomitrella patens*. The nucleotide sequences of mRNAs (and cDNAs) encoding BIL7 proteins and the amino acid sequences of BIL7 proteins in different species of plants have been identified and registered under the Genbank accession numbers as shown in the table below.

TABLE 1

|  | mRNA (or cDNA) | Coding region | Protein |
|---|---|---|---|
| Arabidopsis thaliana | NM_105049 (Ver. NM_105049.4) (SEQ ID NO: 6) | 182 to 1258 | NP_564816 (Ver. NP_564816.1) (SEQ ID NO: 7) |
| Glycine max | XM_003538647 (Ver. XM_003538647.2) (SEQ ID NO: 8) | 193 to 1431 | XP_003538695 (Ver. XP_003538695.1) (SEQ ID NO: 9) |
| Oryza sativa | NM_001055090 (Ver. NM_001055090.1) (SEQ ID NO: 10) | 416 to 1702 | NP_001048555 (Ver. NP_001048555.1) (SEQ ID NO: 11) |
| Zea mays | NM_001149669 (Ver. NM_001149669.2) (SEQ ID NO: 12) | 359 to 1651 | NP_001143141 (Ver. NP_001143141.1) (SEQ ID NO: 13) |
| Raphanus sativus | AJ550021 REGION: complement (join(101320_102240, 102502_102609)) (Ver. AJ550021.2) (SEQ ID NO: 14) | 1 to 1029 | CAZ40337 (Ver. CAZ40337.1) (SEQ ID NO: 15) |
| Populus trichocarpa | XM_002318173 (Ver. XM_002318173.2) (SEQ ID NO: 16) | 298 to 1821 | XP_002318209 (Ver. XP_002318209.1) (SEQ ID NO: 17) |
| Vitis vinifera | XM_002272286 (Ver. XM_002272286.2) (SEQ ID NO: 18) | 177 to 1523 | XP_002272322 (Ver. XP_002272322.1) (SEQ ID NO: 19) |
| Physcomitrella patens | XM_001756821 (Ver. XM_001756821.1) (SEQ ID NO: 20) | 1 to 4092 | XP_001756873 (Ver. XP_001756873.1) (SEQ ID NO: 21) |

The BIL7 protein having the aforementioned common motif also includes homologs of BIL7 proteins from different species of plants. For example, there are three homolog proteins of *A. thaliana* BIL7, and the mRNA (and cDNA) nucleotide sequences and amino acid sequences for those homologs have been registered under the Genbank accession numbers as shown in the table below.

TABLE 2

|  | mRNA (or cDNA) | Coding region | Protein |
|---|---|---|---|
| Arabidopsis thaliana homolog 1 | NM_124622 (Ver. NM_124622.4) (SEQ ID NO: 22) | 227 to 1543 | NP_200056 (Ver. NP_200056.1) (SEQ ID NO: 23) |
| Arabidopsis thaliana homolog 2 | NM_118694 (Ver. NM_118694.4) (SEQ ID NO: 24) | 384 to 1733 | NP_194292 (Ver. NP_194292.2) (SEQ ID NO: 25) |
| Arabidopsis thaliana homolog 3 | NM_106316 (Ver. NM_106316.4) (SEQ ID NO: 26) | 374 to 1669 | NP_177792 (Ver. NP_177792.1) (SEQ ID NO: 27) |

The protein of the present invention is characterized not only by comprising the aforementioned common motif, but also by further comprising an amino acid sequence having at least 25% identity or at least 75% similarity to the amino acid sequence of SEQ ID NO:7 or 11, relative to BIL7 protein of *A. thaliana* or *O. sativa*. In this invention, the aforementioned common motif (i.e., the amino acid sequence of SEQ ID NO:1) is included by an amino acid sequence having at least 25% identity or at least 75% similarity to the amino acid sequence of SEQ ID NO:7 or 11 (in other words, the aforementioned common motif (i.e., the amino acid sequence of SEQ ID NO:1) is contained (present) as part of an amino acid sequence having at least 25% identity or at least 75% similarity to the amino acid sequence of SEQ ID NO:7 or 11).

As referred to herein, the identity in amino acid sequence refers to an identity in amino acid sequence between two proteins of interest, and is expressed by the proportion (%) of amino acid residues matched in the best amino acid sequence alignments produced using a mathematical algorithm known in the art. The identify in amino acid sequence can be determined by visual inspection and mathematical calculation, and can be calculated using a tool known to those skilled in the art, such as homology search program (e.g., BLAST, FASTA), sequence alignment program (e.g., ClustalW)), or genetic information processing software (e.g., GENETYX®). The identity in amino acid sequence, as referred to herein, can be specifically determined using the phylogeny analysis program, ClustalW, which is published on the website of DDBJ (DNA Data Bank of Japan) (http://clustalw.ddbj.nig.ac.jp/index.php?lang=ja) in its default configuration (Version 2.1; Alignment type: slow; DNA Weight Matrix: Gonnet; GAP OPEN: 10; GAP EXTENSION: 0.1).

The protein of the present invention can comprise an amino acid sequence having an identity of at least 25%, at least 30%, at least 40%, at least 50%, at least 60%, at least 70%, at least 80%, at least 85%, at least 90%, at least 95%, at least 97%, at least 98%, or at least 99% with respect to the amino acid sequence of SEQ ID NO:7 or 11.

The identities between *A. thaliana* BIL7 protein and each of its homologs are 41% (homolog 1), 43% (homolog 2) and 28% (homolog 3). Thus, in one preferred embodiment, the protein of the present invention comprises an amino acid sequence having an identity of at least 25%, at least 30%, or at least 40% with respect to the amino acid sequence of SEQ ID NO:7. The identities between *A. thaliana* BIL7 protein and each of *G. max, O. sativa* and *Z. mays* BIL7 proteins are 44% (*G. max* BIL7), 41% (*O. sativa* BIL7) and 40% (*Z. mays* BIL7). Thus, in one preferred embodiment, the protein of this invention comprises an amino acid sequence having at least 40% identity to the amino acid sequence of SEQ ID NO:7. The identities between *O. sativa* BIL7 protein and each of *G. max* and *Z. mays* BIL7 proteins are 42% (*G. max* BIL7) and 85% (*Z. mays* BIL7). Thus, in one preferred embodiment, the protein of this invention comprises an amino acid sequence having an identity of at least 40%, at least 50%, at least 60%, at least 70%, at least 80%, or at least 85% with respect to the amino acid sequence of SEQ ID NO:11.

As referred to herein, the similarity in amino acid sequence refers to a similarity in amino acid sequence between two proteins of interest, and is expressed by the proportion (%) of amino acid residues matched, and amino acid residues similar, in the best amino acid sequence alignments produced using a mathematical algorithm known in the art. The similarity in amino acid sequence is expressed by the relationship between amino acid residues similar in physicochemical properties; for example, in different amino acid groups, such as aromatic amino acids (Phe, Tyr, Trp), hydrophobic amino acids (Asp, Glu), aliphatic amino acids (Ala, Leu, Ile, Val), polar amino acids (Asn, Gln), basic amino acids (Lys, Arg, His), acidic amino acids (Asp, Glu), hydroxyl group-containing amino acids (Ser, Thr), and short side chain amino acids (Gly, Ala, Ser, Thr, Met), the amino acids belonging to the same group are understood to be mutually similar amino acid residues. It is presumed that such similar amino acid residues do not affect the phenotype of a protein. Like the identity in amino acid sequence, the similarity in amino acid sequence can be determined by visual inspection and mathematical calculation, and can be calculated using a tool known to those skilled in the art, such as sequence similarity search program (e.g., BLAST, PSI-BLAST, HMMER) or genetic information processing software (e.g., GENETYX®). The similarity in amino acid sequence, as referred to herein, can be specifically determined using GENETYX® on the network, Ver. 11.1.3 (Genetyx Corporation), with "Protein vs Protein Global Homology" being configured by default ("Unit size to compare" is set to 2).

The protein of the present invention can comprise an amino acid sequence having a similarity of at least 75%, at least 80%, at least 85%, at least 90%, at least 91%, at least 92%, at least 93%, at least 94%, at least 95%, at least 96%, at least 97%, at least 98%, at least, or at least 99% with respect to the amino acid sequence of SEQ ID NO:7 or 11.

The similarities between *A. thaliana* BIL7 protein and each of *G. max, O. sativa* and *Z. mays* BIL7 proteins are 76% (*G. max* BIL7), 76% (*O. sativa* BIL7) and 75% (*Z. mays* BIL7). Thus, in one preferred embodiment, the protein of this invention comprises an amino acid sequence having at least 75% similarity to the amino acid sequence of SEQ ID NO:7. The similarities between *O. sativa* BIL7 protein and each of *G. max* and *Z. mays* BIL7 proteins are 83% (*G. max* BIL7) and 97% (*Z. mays* BIL7). Thus, in one preferred embodiment, the protein of this invention comprises an amino acid sequence having a similarity of at least 75%, at least 80%, at least 85%, at least 90%, at least 95%, or at least 97% with respect to the amino acid sequence of SEQ ID NO:11.

Further, the protein of the present invention is characterized not only by comprising the aforementioned common motif and an amino acid sequence having a specified level of identity or similarity to the amino acid sequence of SEQ ID NO:7 or 11, but also by having an activity to increase plant biomass.

As referred to herein, the term "plant biomass" is meant to refer to the amount of the whole or part or a plant organ(s) of a plant, or a combination thereof. Examples of the whole or part or a plant organ(s) of a plant include whole plant, aboveground part, root, stem, leaf, fruit, seed, embryo, ovule, ovary, shoot apex, anther, pollen, or panicle. Among them, fruit, seed, panicle, root, stem, leaf, or anther is preferred. Examples of "amount" include number, size, length, width, weight, area, or volume. Thus, examples of "biomass" include, but are not limited to, whole plant weight, aboveground part weight (e.g., Upper-ground dry matter weight, yield, stem diameter, number of stems, culm length, plant height, leaf area, number of leaves, flag leaf length, leaf length, leaf width, number of rough rice, rough rice weight (e.g., 1000 fertile rough rice weight, whole weight of fertile rough rice), number of seeds, number of tillers, number of panicles, number of rough rice per panicle, number of fertile rough rice per panicle, percentage of fertile rough rice, panicle length, maximum panicle length, weight of one panicle, or panicle weight per plant. The term "increase(d)" means that any of the plant biomasses mentioned above increase alone or in combination.

The activity to increase plant biomass can be evaluated by, for example, using the biomass of the control (e.g., parent plant, non-transformant, wild-type plant) as an indicator for increase and comparing the biomass of a mature plant with that of the control. If an increase in plant biomass is observed as compared to the control, an introduced protein can be evaluated as having an activity to increase plant biomass. When the biomass is quantifiable, the quantified values are compared, and if an increase in biomass by, for example, at least 1%, at least 3%, at least 5%, at least 10%, at least 15%, at least 20%, at least 25%, at least 30%, at least 40%, at least 50%, at least 60%, at least, or at least 70%, is observed, an introduced protein can be evaluated as having an activity to increase plant biomass.

In the present invention, the amino acid sequence of SEQ ID NO:1 can be the amino acid sequence of SEQ ID NO:2 as shown below. Examples of a plant having a protein comprising the amino acid sequence of SEQ ID NO:2 as a common motif include, but are not limited to, *A. thaliana, G. max, O. sativa,* and *Z. mays*. Also, homologs of BIL7 proteins from the aforementioned plants (e.g., homolog proteins of *A. thaliana* BIL7) are included by the protein having the amino acid sequence of SEQ ID NO:2.

```
SEQ ID NO: 2:
Ala-Pro-Pro-Ser-Ser-Pro-Ala-Ser-Phe-X29-X30-Ser-

X31-X32-X33-Ser-X34-X35-X36-X37-Pro-X38-Ser-X39-

X40-X41-X42-Gly-Pro-Tyr-Ala-X43-Glu-Thr-Gln-X44-

Val-X45-Pro-Pro-Val-Phe-Ser-X46-X47-X48-Thr-Glu-

Pro-Ser-X49-Ala-Pro-X50-Thr-Pro-Ser-X51-Pro-Ser-

Ser-Pro-X52-Val-Pro-X53-Ala-X54-Pro-X55-Ser-Pro-

X56-Leu-X57-Ser-Pro
```

(where X29 represents Phe, Leu or Thr; X30 represents Gln, His, Pro or Asn; X31 represents Glu, Gly, Asp or Ala; X32 represents Pro, Gly or Leu; X33 represents Pro, Ala, Thr or Ser; X34 represents Ala, Val, Ile or Thr; X35 represents Thr, Ala, Val or Ser; X36 represents Gln or His; X37 represents Ser or Thr; X38 represents 10 to 25 amino acid residues; X39 represents Ile, Val, Ala or Met; X40 represents Phe or Tyr; X41 represents Ala or Thr; X42 represents Ile, Val or Thr; X43 represents His or Asn; X44 represents Leu or Pro; X45 represents Ser or Thr; X46 represents Thr or Ala; X47 represents Tyr or Phe; X48 represents Thr or Ile; X49 represents Ser or Thr; X50 represents Ile, Phe or Tyr; X51 represents 3 to 15 amino acid residues; X52 represents Glu or Asp; X53 represents Phe or Tyr; X54 represents 20 to 35 amino acid residues; X55 represents Gly, Glu or Asp; X56 represents 3 to 5 amino acid residues; and X57 represents Ile or Arg.)

In the aforementioned amino acid sequence, X38 preferably represents 12 to 21 amino acid residues, more preferably 15 to 21 amino acid residues; X51 preferably represents 3 to 12 amino acid residues, more preferably 8 to 12 amino acid residues; X54 preferably represents 23 to 35 amino acid residues, more preferably 23 to 30 amino acid residues; and X56 preferably represents 3 or 4 amino acid residues, more preferably 3 amino acid residues.

The protein of the present invention may also comprise the amino acid sequence of SEQ ID NO:3 as shown below. The aforementioned amino acid sequence of SEQ ID NO:1 or 2 is included by the amino acid sequence of SEQ ID NO:3 (in other words, the amino acid sequence of SEQ ID NO:1 or 2 is contained (present) as part of the amino acid sequence of SEQ ID NO:3). Also, the amino acid sequence of SEQ ID NO:3 is included by an amino acid sequence having at least 25% identity or at least 75% similarity to the amino acid sequence of SEQ ID NO:7 or 11 (in other words, the amino acid sequence of SEQ ID NO:3 is contained (present) as part of an amino acid sequence having at least 25% identity or at least 75% similarity to the amino acid sequence of SEQ ID NO:7 or 11). Examples of a plant having a protein comprising the amino acid sequence of SEQ ID NO:3 as a common motif include, but are not limited to, *A. thaliana* and *O. sativa*.

```
SEQ ID NO: 3:
Met-X58-Ser-Gly-X59-Asn-X60-X61-Asp-Thr-X62-Asn-

Ala-Ala-Ala-X63-Ala-Ile-X64-X65-X66-X67-X68-Arg-

X69-Arg-Lys-Trp-X70-X71-X72-X73-Ser-X74-X75-X76-

Cys-Phe-Gly-Ser-X77-X78-X79-X80-X81-Arg-Ile-X82-

X83-X84-Val-Leu-Val-Pro-Glu-Pro-X85-Pro-Phe-X86-

Ala-Pro-Pro-Ser-Ser-Pro-Ala-Ser-Phe-X87-Gln-Ser-

X88-X89-X90-Ser-X91-X92-Gln-Ser-Pro-Val-Gly-X93-

X94-Ser-Phe-Ser-Pro-Leu-X95-X96-Asn-X97-Pro-Ser-

Ile-Phe-Ala-Ile-Gly-Pro-Tyr-Ala-His-Glu-Thr-Gln-

Leu-Val-Ser-Pro-Pro-Val-Phe-Ser-X98-X99-Thr-Thr-

Glu-Pro-Ser-X100-Ala-Pro-X101-Thr-Pro-Pro-X102-

Ser-X103-X104-Leu-Thr-Thr-X105-Pro-Ser-Ser-Pro-

Glu-Val-Pro-X106-Ala-X107-Leu-X108-X109-Ser-X110-

Glu-X111-Gln-X112-Tyr-Gln-X113-X114-Pro-X115-Ser-

Pro-X116-Gly-X117-Leu-Ile-Ser-Pro-Ser-X118-Ser-

Gly-X119-X120-Ser-Pro-Phe-Pro-Asp-X121-Ser-X122-

Phe-Pro-X123-Phe-X124-Val-X125-X126-Pro-Pro-Lys-

X127-Leu-X128-Gly-X129-His-X130-Val-Ser-Phe-X131-

Leu-X132-X133-X134-X135-Val-X136-Arg-Cys-X137-

X138-X139-Lys-X140-Pro-X141-X142-Ser-X143-Asp-

X144-Ser-Leu-X145-X146-X147-Lys-Glu-Phe-X148-Phe-

X149-Val-X150-X151-X152-X153-X154-Ala-X155-X156-

Lys-X157-Trp-Ser-Phe-Phe-Pro-Val-X158-Gln-X159-

Gly
```

(where X58 represents Arg or Gln; X59 represents 3 to 10 amino acid residues; X60 represents Val or Ser; X61 represents Phe or Val; X62 represents Ile or Val; X63 represents Ser or Val; X64 represents Ala or Val; X65 represents Ser or Thr; X66 represents Ser or Ala; X67 represents Asp or Glu; X68 represents Asp or Ser; X69 represents 5 to 10 amino acid residues; X70 represents Trp or Ala; X71 represents Asn or Asp; X72 represents Arg or Trp; X73 represents Trp or Leu; X74 represents Leu or Val; X75 represents Leu or Tyr; X76 represents Lys or Phe; X77 represents Ser or Gln; X78 represents Arg or Lys; X79 represents Gln or Asn; X80 represents Arg or Gly; X81 represents Lys or Arg; X82 represents Gly or Ser; X83 represents Asn or His; X84 represents Ser or Ala; X85 represents 20 to 25 amino acid residues; X86 represents Ile or Val; X87 represents Phe or Leu; X88 represents Glu or Gly; X89 represents Pro or Gly; X90 represents Pro or Ala; X91 represents Ala or Ile; X92 represents Thr or Val; X93 represents Ile or Ala; X94 represents Leu or Pro; X95 represents Pro or Ser; X96 represents Cys or Pro; X97 represents 1 to 10 amino acid residues; X98 represents Thr or Ala; X99 represents Tyr or Phe; X100 represents Ser or Thr; X101 represents Ile or Phe; X102 represents 1 to 5 amino acid residues; X103 represents Ile or Val; X104 represents Tyr or His; X105 represents 0 to 5 amino acid residues; X106 represents Phe or Tyr; X107 represents Gln or Lys; X108 represents Phe or Leu; X109 represents Asn or Thr; X110 represents 10 to 20 amino acid residues; X111 represents Phe or Leu; X112 represents Phe or Ser; X113 represents Leu or Ile; X114 represents Pro or Tyr; X115 represents Gly or Glu; X116 represents Leu or Ile; X117 represents Gln or Arg; X118 represents 1 to 5 amino acid residues; X119 represents Pro or Thr; X120 represents Thr or Cys; X121 represents 1 to 10 amino acid residues; X122 represents Leu or Thr; X123 represents His or Ser; X124 represents Gln or Pro; X125 represents Ser or Arg; X126 represents Asp or Glu; X127 represents Leu or Ile; X128 represents 3 to 20 amino acid residues; X129 represents 10 to 30 amino acid residues; X130 represents 1 to 5 amino acid residues; X131 represents Asp or Glu; X132 represents Asp or Thr; X133 represents Ala or Val; X134 represents Asp or Glu; X135 represents His or Asp; X136 represents Ile or Ala; X137 represents Val or Leu; X138 represents Asp or Glu; X139 represents Gln or Lys; X140 represents 3 to 25 amino acid residues; X141 represents Glu or Arg; X142 represents Ala or Glu; X143 represents Ser or Asn; X144 represents 5 to 25 amino acid residues; X145 represents Gly or Arg; X146 represents Ser or Lys; X147 represents Asn or Ala; X148 represents Asn or Lys; X149 represents 5 to 15 amino acid residues; X150 represents Asp or Gly; X151 represents Glu or Ser; X152 represents His or Asp; X153 represents Arg or Trp; X154 represents Ser or Trp; X155 represents Ser or Asn; X156 represents Pro or Glu; X157 represents 5 to 15 amino acid residues; X158 represents Met or Ala; and X159 represents Ser or Pro.)

In the aforementioned amino acid sequence, X59 preferably represents 4 to 7 amino acid residues; X69 preferably represents 8 to 10 amino acid residues; X85 preferably represents 21 to 22 amino acid residues; X97 preferably represents 2 to 7 amino acid residues; X102 preferably represents 2 to 4 amino acid residues; X105 preferably represents 0 to 2 amino acid residues; X110 preferably represents 10 to 17 amino acid residues; X118 preferably represents 2 to 3 amino acid residues; X121 preferably represents 3 to 8 amino acid residues; X128 preferably represents 5 to 18 amino acid residues; X129 preferably represents 13 to 28 amino acid residues; X130 preferably represents 1 to 2 amino acid residues; X140 preferably represents 5 to 24 amino acid residues; X144 preferably represents 7 to 22 amino acid residues; X149 preferably represents 8 to 11 amino acid residues; and X157 preferably represents 4 to 11 amino acid residues.

The protein of the present invention may also comprise the amino acid sequence of SEQ ID NO:4 as shown below. The aforementioned amino acid sequence of SEQ ID NO:1 or 2 is included by the amino acid sequence of SEQ ID NO:4 (in other words, the amino acid sequence of SEQ ID NO:1 or 2 is contained (present) as part of the amino acid sequence of SEQ ID NO:4). Also, the amino acid sequence of SEQ ID NO:4 is included by an amino acid sequence having at least 75% identity or at least 75% similarity to the amino acid sequence of SEQ ID NO:7 or 11 (in other words, the amino acid sequence of SEQ ID NO:4 is contained (present) as part of an amino acid sequence having at least 25% identity or at least 75% similarity to the amino acid sequence of SEQ ID NO:7 or 11). Examples of a plant having a protein comprising the amino acid sequence of SEQ ID NO:4 as a common motif include, but are not limited to, *A. thaliana* and *G. max*.

```
SEQ ID NO: 4:
Met-Arg-X160-Gly-Ala-Asn-Gly-X161-Asn-Asn-X162-

X163-X164-Thr-Ile-Asn-Ala-Ala-Ala-X165-X166-Ile-

Ala-Ser-X167-X168-X169-Arg-Leu-X170-Gln-X171-X172-

Pro-X173-X174-X175-Lys-X176-X177-Trp-X178-Asn-

X179-X180-Ser-X181-X182-X183-Cys-Phe-Gly-X184-

X185-X186-X187-Arg-X188-Arg-Ile-Gly-X189-X190-Val-

Leu-Val-Pro-Glu-X191-X192-X193-X194-X195-X196-

X197-Asn-X198-Thr-X199-Ile-X200-X201-X202-X203-

Phe-X204-Ala-Pro-Pro-Ser-Ser-Pro-Ala-Ser-Phe-X205-

X206-Ser-Glu-Pro-Pro-Ser-X207-X208-Gln-Ser-Pro-

X209-X210-Ile-Leu-Ser-X211-X212-Pro-X213-Ser-Ile-

Phe-Ala-Ile-Gly-Pro-Tyr-Ala-His-Glu-Thr-Gln-Leu-

Val-Ser-Pro-Pro-Val-Phe-Ser-Thr-X214-Thr-Thr-Glu-

Pro-Ser-X215-Ala-Pro-X216-Thr-Pro-Pro-X217-Thr-

Thr-Pro-Ser-Ser-Pro-Glu-Val-Pro-Phe-Ala-Gln-Leu-

X218-X219-X220-Asn-X221-X222-X223-X224-X225-X226-

X227-X228-X229-Phe-X230-Tyr-X231-Phe-X232-X233-

Tyr-Gln-Leu-X234-Pro-Gly-Ser-Pro-X235-Gly-Gln-Leu-

Ile-Ser-Pro-X236-Ser-X237-X238-X239-Ser-Pro-Phe-

Pro-Asp-X240-Ser-Leu-X241-X242-X243-Phe-Gln-X244-

X245-Asp-X246-Ser-X247-X248-X249-X250-Gly-X251-

X252-Thr-Pro-X253-Gln-X254-X255-X256-X257-Pro-

X258-X259-X260-Val-Ser-X261-X262-X263-X264-Ala-

X265-X266-Val-X267-X268-Cys-Val-X269-Lys-Leu-X270-

Thr-X271-X272-Pro-X273-Glu-X274-X275-Ser-Asp-X276-

Glu-X277-X278-X279-His-X280-Lys-Glu-Phe-Asn-Phe-

X281-X282-X283-Glu-X284-Leu-X285-X286-Asp-X287-

Ala-Ser-X288-Ser-Asn-X289-Trp-Ser-Phe-Phe-Pro-

X290-X291-X292-X293-Gly
```

(where X160 represents 0 to 3 amino acid residues; X161 represents 0 to 5 amino acid residues; X162 represents Val or Thr; X163 represents Phe or Leu; X164 represents Asp or Glu; X165 represents Ser or Thr; X166 represents Ala or Val; X167 represents Ser or Val; X168 represents Asp or Glu; X169 represents Asp or Asn; X170 represents His or Asp; X171 represents Ser or Pro; X172 represents Ser or His; X173 represents Ile or His; X174 represents His or Val; X175 represents Lys or Gln; X176 represents Arg or Lys; X177 represents Lys or Ser; X178 represents Trp or Gly; X179 represents Arg or Trp; X180 represents Trp or Leu; X181 represents Leu or Ile; X182 represents Leu or Tyr; X183 represents Lys or Trp; X184 represents Ser or His; X185 represents Ser or Arg; X186 represents Arg or Lys; X187 represents Gln or Asn; X188 represents Lys or Gln; X189 represents Asn or His; X190 represents Ser or Ala; X191 represents Pro or Arg; X192 represents Val or Ile; X193 represents Ser or Pro; X194 represents Met or Ser; X195 represents Ser or Gly; X196 represents Ser or Thr; X197 represents Ser or Asp; X198 represents Ser or Ala; X199 represents 5 to 15 amino acid residues; X200 represents Thr or Ile; X201 represents Thr or Pro; X202 represents Leu or Phe; X203 represents Pro or His; X204 represents Ile or Val; X205 represents Phe or Leu; X206 represents Gln or His; X207 represents Ala or Val; X208 represents Thr or Ala; X209 represents Val or Ser; X210 represents Gly or Ala; X211 represents Phe or Leu; X212 represents Ser or Thr; X213 represents 1 to 10 amino acid residues; X214 represents Tyr or Phe; X215 represents Ser or Thr; X216 represents Ile or Phe; X217 represents 3 to 15 amino acid residues; X218 represents Phe or Leu; X219 represents Asn or Asp; X220 represents Ser or Pro; X221 represents His or Asn; X222 represents Gln or Lys; X223 represents Thr or Asn; X224 represents Gly or Ser; X225 represents Ser or Glu; X226 represents Tyr or Thr; X227 represents Gly or Tyr; X228 represents Tyr or Gln; X229 represents Lys or Arg; X230 represents 3 to 7 amino acid residues; X231 represents Glu or Asp; X232 represents Gln or His; X233 represents Phe or Ser; X234 represents Pro or His; X235 represents Leu or Val; X236 represents 1 to 10 amino acid residues; X237 represents Gly or Ser; X238 represents Pro or Thr; X239 represents Thr or Ser; X240 represents 1 to 10 amino acid residues; X241 represents Phe or Leu; X242 represents Pro or Leu; X243 represents His or Asn; X244 represents Val or Thr; X245 represents Ser or Asp; X246 represents 3 to 10 amino acid residues; X247 represents Pro or His; X248 represents Lys or Gln; X249 represents Thr or Gly; X250 represents Ala or Ser; X251 represents Val or Ser; X252 represents Thr or Leu; X253 represents 1 to 10 amino acid residues; X254 represents Lys or Ala; X255 represents Ile or Ser; X256 represents Val or Phe; X257 represents Pro or Leu; X258 represents His or Ser; X259 represents Lys or His; X260 represents Pro or Trp; X261 represents Phe or Ile; X262 represents Asp or Glu; X263 represents Leu or Val; X264 represents Asp or Ser; X265 represents Asp or Gln; X266 represents His or Glu; X267 represents Ile or Phe; X268 represents Arg or Asn; X269 represents 1 to 15 amino acid residues; X270 represents Arg or Lys; X271 represents Thr or Asp; X272 represents Phe or Ala; X273 represents 0 to 15 amino acid residues; X274 represents Ala or Thr; X275 represents Ser or Pro; X276 represents 1 to 15 amino acid residues; X277 represents Ser or Arg; X278 represents Met or Val; X279 represents Asn or His; X280 represents 5 to 10 amino acid residues; X281 represents Gly or Asp; X282 represents Thr or Asn; X283 represents Asp or Ala; X284 represents 1 to 10 amino acid residues; X285 represents Thr or Val; X286 represents Val or Ala; X287 represents 1 to 10 amino acid residues; X288 represents 1 to 7 amino acid residues; X289 represents Asp or Asn; X290 represents Val or Met; X291 represents Met or Ile; X292 represents Gln or Arg; and X293 represents Ser or Pro.)

In the aforementioned amino acid sequence, X160 preferably represents 0 to 1 amino acid residue; X161 preferably represents 0 to 3 amino acid residues; X199 preferably represents 7 to 9 amino acid residues; X213 preferably represents 4 to 7 amino acid residues; X217 preferably represents 6 to 10 amino acid residues; X230 preferably represents 4 to 5 amino acid residues; X236 preferably represents 3 to 6 amino acid residues; X240 preferably represents 3 to 9 amino acid residues; X246 preferably represents 5 to 9 amino acid residues; X253 preferably represents 3 to 7 amino acid residues; X269 preferably represents 2 to 12 amino acid residues; X273 preferably represents 0 to 11 amino acid residues; X276 preferably represents 1 to 11 amino acid residues; X280 preferably represents 6 to 10 amino acid residues; X284 preferably represents 2 to 8 amino acid residues; X287 preferably represents 4 to 7 amino acid residues; and X288 preferably represents 3 to 5 amino acid residues.

The protein of the present invention may also comprise the amino acid sequence of SEQ ID NO:5 as shown below. The aforementioned amino acid sequence of SEQ ID NO:1 or 2 is included by the amino acid sequence of SEQ ID NO:5 (in other words, the amino acid sequence of SEQ ID NO:1 or 2 is contained (present) as part of the amino acid sequence of SEQ ID NO:5). Also, the amino acid sequence of SEQ ID NO:5 is included by an amino acid sequence having at least 25% identity or at least 75% similarity to the amino acid sequence of SEQ ID NO:7 or 11 (in other words, the amino acid sequence of SEQ ID NO:5 is contained (present) as part of an amino acid sequence having at least 25% identity or at least 75% similarity to the amino acid sequence of SEQ ID NO:7 or 11). Examples of a plant having a protein comprising the amino acid sequence of SEQ ID NO:5 as a common motif include, but are not limited to, *O. sativa*, and *Z. mays*.

SEQ ID NO: 5:
Met-Gln-Ser-Gly-X294-X295-Met-Arg-Pro-Val-His-Asn-

Ser-Val-Asp-Thr-Val-Asn-Ala-Ala-Ala-Val-Ala-Ile-

Val-Thr-Ala-Glu-Ser-Arg-Thr-Gln-Pro-X296-Ala-Glu-

-continued

X297-Arg-Arg-Lys-Trp-Ala-Asp-X298-Le

Gly; X315 represents Thr or Ala; X316 represents 0 to 5 amino acid residues; X317 represents Gln or Pro; X318 represents Ile or Asn; X319 represents Glu or Asp; X320 represents Ala or Gly; X321 represents Cys or Ser; X322 represents Val or Met; X323 represents Thr or Ala; X324 represents Thr or Ala; X325 represents Phe or Leu; X326 represents Pro or Arg; X327 represents Ser or Leu; X328 represents Ile or Val; X329 represents His or Gln; X330 represents Asn or Pro; X331 represents Asp or Glu; X332 represents Asn or Ala; X333 represents Asn or Ser; X334 represents Glu or Asp; X335 represents Ala or Gly; X336 represents Ala or Thr; X337 represents Arg or His; X338 represents Val or Ala; X339 represents Asn or Ser; X340 represents 0 to 5 amino acid residues; X341 represents Pro or His; X342 represents Asp or Glu; X343 represents Thr or Ala; X344 represents Cys or Tyr; X345 represents Thr or Ser; X346 represents Lys or Leu; X347 represents Lys or Asn; X348 represents Ala or Val; X349 represents Pro or Gly; X350 represents Ile or Met; X351 represents Ser or Thr; X352 represents Arg or Lys; X353 represents Ser or Asn; X354 represents Phe or His; and X355 represents Ala or Val.)

In the aforementioned amino acid sequence, X299 preferably represents 0 to 2 amino acid residues; X311 preferably represents 1 to 2 amino acid residues; X316 preferably represents 1 to 2 amino acid residues; and X340 preferably represents 0 to 2 amino acid residues.

In the present invention, a nucleic acid encoding the aforementioned protein is used. As referred to herein, the term "nucleic acid" refers to a polymer in which nucleotides are linked together via phosphoester bonds, and is interchangeably used with the terms "polynucleotide" and "oligonucleotide". The structure of the nucleic acid is not particularly limited, and can be single-strand or double-strand. The nucleic acid includes deoxyribonucleic acid (DNA), ribonucleic acid (RNA), and hybrids thereof (e.g., DNA-RNA hybrid double strand; chimeric nucleic acid in which DNA and RNA are linked into a single strand). The building blocks of the nucleic acid mainly include purine bases such as adenine (A) and guanine (G), and pyrimidine bases such as thymine (T), cytosine (C) and uracil (U), and also include modified forms of said bases as long as they are capable of translating into a protein of interest. The nucleic acid used in this invention is preferably mRNA or cDNA encoding a protein of interest.

The nucleic acid and protein of the present invention are not particularly limited as long as they are capable of increasing plant biomass, but the inventive nucleic acid and protein are preferably derived from a dicotyledonous plant or a monocotyledonous plant. Or they may be derived from *Physcomitrella patens*. Examples of the dicotyledonous plant include, but are not limited to, *Arabidopsis thaliana, Glycine max, Raphanus sativus, Populus trichocarpa, Vitis vinifera, Gossypium arboretum* (cotton), *Brassica napus* (rape), *Beta vulgaris* (beet), *Nicotiana tabacum* (tobacco), and *Solanum lycopersicum* (tomato). Among them, *A. thaliana, G. max,* and *R. sativus* are preferred, with *A. thaliana* and *G. max* being more preferred, and *A. thaliana* being most preferred. Examples of the monocotyledonous plant include, but are not limited to, *Oryza sativa, Zea mays, Triticum aestivum* (wheat), *Hordeum vulgare* (barley), *Sorghum bicolor* (sorghum), *Saccharum officinarum* (sugarcane), and *Allium cepa* (onion). Among them, *O. sativa, Z. mays,* and *T. aestivum* are preferred, with *O. sativa* and *Z. mays* being more preferred.

As the protein of the present invention, BIL7 proteins derived from different species of plants can be used; for example, BIL7 proteins derived from *A. thaliana, G. max, O. sativa, Z. mays, R. sativus, P. trichocarpa, V vinifera,* or *P. patens* (i.e., proteins comprising the amino acid sequence of any of SEQ ID NOs:7, 9, 11, 13, 15, 17, 19 and 21) can be used. Also, as the inventive protein, homologs of BIL7 proteins derived from different species of plants can be used; for example, homolog proteins of *A. thaliana* BIL7 (i.e., proteins comprising the amino acid sequence of any of SEQ ID NOs:23, 25 and 27) can be used.

In one embodiment, the present invention also covers proteins that comprise an amino acid sequence derived from any of the amino acid sequences of BIL7 proteins derived from different species of plants and their homologs (e.g., the amino acid sequence of any of SEQ ID NOs:7, 9, 11, 13, 15, 17, 19, 21, 23, 25 and 27) by deletion, insertion, substitution, or addition of one or some amino acids, and which have an activity to increase plant biomass. As referred to above, "some amino acids" refers to, for example, 2 to 40 amino acids, 2 to 30 amino acids, 2 to 20 amino acids, 2 to 10 amino acids, 2 to 7 amino acids, 2 to 5 amino acids, 5 amino acids, 4 amino acids, 3 amino acids, or 2 amino acids. The deletion, insertion, substitution or addition of one or some amino acids can be done by using a method known in the art (e.g., by altering a nucleic acid). It is preferred that such an altered amino acid sequence comprise the amino acid sequence of SEQ ID NO:1.

Introduction of a mutation into a nucleic acid can be done by the Kunkel method, the gapped duplex method, or any other methods pursuant thereto. For example, a mutation introduction kit based on site-directed mutanogenesis (e.g., Transformer™ Site-Directed Mutagenesis Kit (Clontech Laboratories, Inc.) or QuikChange Site-Directed Mutagenesis Kit (Agilent Technologies)) can be used. For introduction of a mutation into a nucleic acid, a chemical mutagenic agent such as EMS (ethyl methanesulfonate), 5-bromouracil, 2-aminopurine, hydroxylamine, N-methyl-N'-nitro-N-nitrosoguanidine or any other carcinogenic compound, or a radiant or ultraviolet ray such as X-ray, α-ray, β-ray, γ-ray or ion beam can be used.

In one embodiment, the present invention covers proteins that comprise an amino acid sequence having an identity of at least 25%, at least 30%, at least 40%, at least 50%, at least 60%, at least 70%, at least 80%, at least 85%, at least 90%, at least 95%, at least 96%, at least 97%, at least 98%, or at least 99% identity, or a similarity of at least 70%, at least 80%, at least 85%, at least 90%, at least 95%, at least 96%, at least 97%, at least 98%, or at least 99%, with respect to any of the amino acid sequences of BIL7 proteins derived from different species of plants and their homologs (e.g., the amino acid sequence of any of SEQ ID NOs:7, 9, 11, 13, 15, 17, 19, 21, 23, 25 and 27), and which have an activity to increase plant biomass. The identity and similarity in amino acid sequence have been described hereinabove. It is preferred that such a similar amino acid sequence comprise the amino acid sequence of SEQ ID NO:1.

When BIL7 protein derived from *A. thaliana, G. max, O. sativa, Z. mays, R. sativus, P. trichocarpa, V. vinifera,* or *P. patens* is used as the protein of the present invention, a nucleic acid comprising the nucleotide sequence of any of SEQ ID NOs:6, 8, 10, 12, 14, 16, 18 and 20 is mainly used as a nucleic acid encoding said BIL7 protein. When any of three homolog proteins of *A. thaliana* BIL7 is used, a nucleic acid comprising the nucleotide sequence of any of SEQ ID NOs:22, 24 and 26 is mainly used as a nucleic acid encoding such a homolog protein.

In one embodiment of the present invention, the nucleic acid comprising the nucleotide sequence of any of SEQ ID NOs:6, 8, 10, 12, 14, 16, 18, 20, 22, 24 and 26 also includes nucleic acids that hybridize under stringent conditions to a nucleic acid consisting of a nucleotide sequence complementary to said nucleotide sequence, and which encode a protein having an activity to increase plant biomass.

As referred to above, the "under stringent conditions" means that hybridization takes place under moderately or highly stringent conditions. To be specific, the moderately stringent conditions can be easily determined by those having ordinary skill in the art on the basis of, for example, the length of nucleic acid. Basic conditions are described in Sambrook, et al., *Molecular Cloning: A Laboratory Manual*, 3rd ed., ch. 6, Cold Spring Harbor Laboratory Press, 2001. Typically, the moderately stringent conditions comprise: prewashing in 5×SSC, 0.5% SDS, 1.0 mM EDTA (pH8.0); hybridization in ca. 50% formamide, 2-6×SSC, preferably 5-6×SSC, 0.5% SDS at about 42° C. (or any other similar hybridization solution like a Stark's solution in ca. 50% formamide at about 42° C.); and washing in 0.1-6×SSC, 0.1% SDS at about 50-68° C. The moderately stringent conditions preferably comprise hybridization (and washing) in 6×SSC, 0.5% SDS at about 50° C.

The highly stringent conditions can also be easily determined by those skilled in the art on the basis of, for example, the length of nucleic acid. The highly stringent conditions are generally defined as involving hybridization and/or washing at a higher temperature and/or a lower salt concentration than the moderately stringent conditions (e.g., hybridization in ca. 0.5% SDS, and 6-0.2×SSC, preferably 6×SSC, more preferably 2×SSC, still more preferably 0.2× SSC, or 0.1×SSC, at about 65° C.), for example, as involving hybridization under the aforementioned conditions and washing in 0.2-0.1×SSC, 0.1% SDS at about 65-68° C. As a buffer for use in hybridization and washing, SSPE (1×SSPE: 0.15 M NaCl, 10 mM NaH$_2$PO$_4$, and 1.25 mM EDTA, pH7.4) can be used in place of SSC (1×SSC: 0.15M NaCl and 15 mM sodium citrate). Washing is done for about 15 minutes to 1 hour after the completion of hybridization.

There can also be used a commercial hybridization kit in which no radioactive material is used as a probe. Specific examples include hybridization using the ECL direct labeling & detection system (produced by Amersham). Stringent hybridization is performed, for example, under the following conditions: after 5% (w/v) of a blocking reagent and 0.5 M of NaCl are added to a hybridization buffer in a kit, hybridization is performed at 42° C. for 4 hours, and washing is done twice in 0.4% SDS and 0.5×SSC at 55° C. for 20 minutes, and then once in 2×SSC at room temperature for 5 minutes.

In one embodiment, the present invention also covers nucleic acids that have an identity of at least 70%, at least 80%, at least 85%, at least 90%, at least 95%, at least 96%, at least 97%, at least 98%, or at least 99% with respect to the nucleotide sequence of any of SEQ ID NOs:6, 8, 10, 12, 14, 16, 18, 20, 22, 24 and 26, and which encode a protein having an activity to increase plant biomass.

The identity between two nucleotide sequences can be determined by visual inspection and mathematical calculation, or is more preferably determined by comparing sequence information using a computer program. A typical and preferred computer program is the Wisconsin Package version 10.0 program, "GAP", developed by Genetics Computer Group (GCG; Madison, Wis.) (Devereux, et al., 1984, *Nucl. Acids Res.*, 12: 387). By using this "GAP" program, comparison can be made not only between two nucleotide sequences, but also between two amino acid sequences, and between a nucleotide sequence and an amino acid sequence.

Preferred default parameters for the "GAP" program include: (1) the GCG implementation of a unitary comparison matrix (containing a value of 1 for identities and 0 for non-identities) for nucleotides, and the weighted amino acid comparison matrix of Gribskov and Burgess, *Nucl. Acids Res.*, 14: 6745, 1986, as described by Schwartz and Dayhoff, eds., *Atlas of Polypeptide Sequence and Structure*, National Biomedical Research Foundation, pp. 353-358, 1979; or other comparable comparison matrices; (2) a penalty of 30 for each gap and an additional penalty of 1 for each symbol in each gap for amino acid sequences; or penalty of 50 for each gap and an additional penalty of 3 for each symbol in each gap for nucleotide sequences; (3) no penalty for end gaps; and (4) no maximum penalty for long gaps. Other sequence comparison programs available to those skilled in the art include, for example, the BLASTN program, version 2.2.7, available on the website of the National Library of medicine (http://www.ncbi.nlm.nih.gov/blast/bl2seq/bls.html), or the UW-BLAST2.0 algorithm. Standard default parameter settings for UW-BLAST2.0 are described on the following website: http://blast.wustl.edu. In addition, the BLAST algorithm uses the BLOSUM62 amino acid scoring matrix, and optional selection parameters that can be used are as follows: (A) inclusion of a filter to mask segments of the query sequence that have low compositional complexity (as determined by the SEG program of Wootton and Federhen (*Computers and Chemistry*, 1993); also refer to Wootton and Federhen, 1996, Analysis of compositionally biased regions in sequence databases, *Methods Enzymol.* 266: 554-71) or segments consisting of short-periodicity internal repeats (as determined by the XNU program of Clayerie and States (*Computers and Chemistry*, 1993)); and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported); a preferred E-score threshold value is 0.5, or is, in ascending order of preferability, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

(2) Construct

The present invention provides a construct comprising the above-described nucleic acid and a promoter. As referred to herein, the "construct" refers to a conjugate in which a plurality of nucleic acids are linked together, and the construct of this invention comprises the above-described nucleic acid and a promoter as its constitutional units. In this invention, the nucleic acid and the promoter need not necessarily be directly linked together, and may also be indirectly linked together via a different type of nucleic acid. It is preferred that the promoter be operably linked to the nucleic acid of this invention. The phrase "operably linked" means that the promoter is linked to a nucleic acid of interest such that the promoter can exhibit its function—i.e., transcribe the nucleic acid of interest.

The promoter is not particularly limited as long as it is capable of transcribing a nucleic acid of interest in a plant cell. Examples of the promoter include, but are not limited to, cauliflower mosaic virus 35S promoter (CaMV35S), various ubiquitin promoters, various actin promoters, tobacco PR1a gene promoter, nopaline synthase gene promoter, napin gene promoter, and oleosin gene promoter.

In the present invention, a promoter having a function of expressing a nucleic acid in a plant in a site-specific manner can also be used. Examples of such a promoter include, but are not limited to, promoters expressing a nucleic acid in a leaf-specific manner (e.g., *O. sativa* psb0 gene promoter (Japanese Patent Application Publication No. JP 2010-166924)), promoters expressing a nucleic acid in a stem-specific manner (e.g., *A. thaliana* FA6 promoter (Gupta, et al., 2012 *Plant Cell Rep.* 31: 839-850)), promoters expressing a nucleic acid in a root-specific manner (e.g., RCc3 promoter (Xu, et al., 1995 *Plant Mol Biol* 27: 237-248)), and promoters expressing a nucleic acid mainly in vegetative organs such as roots, stems and leaves (e.g., *A. thaliana* AS promoter; Non-Patent Literature 1).

Further, an inducible promoter can be used in the present invention. Such a promoter can be exemplified by promoters that are known to be expressed by external causes such as infection or invasion of fungi, bacteria or viruses, high or low temperature, drought, ultraviolet irradiation, or distribution of particular compounds such as hormones like auxins or brassinosteroids. Specific examples of such promoters include, but are not limited to: an *O. sativa* chitinase gene promoter (Xu, et al., 1996 *Plant Mol. Biol.* 30:387) and a tobacco PR protein gene promoter (Ohshima, et al., 1990 *Plant Cell* 2:95), which are expressed by infection or invasion of fungi, bacteria or viruses; an *O. sativa* "lip19" gene promoter induced by low temperature (Aguan, et al., 1993 *Mol. Gen. Genet.* 240:1); *O. sativa* "hsp80" and "hsp72" gene promoters induced by high temperature (Van Breusegem, et al., 1994 *Planta* 193:57); an *A. thaliana* "rab16" gene promoter induced by drought (Nundy, et al., 1990 *Proc. Natl. Acad. Sci.* USA 87:1406); a *Petroselinum crispum* (parsley) chalcone synthase gene promoter induced by ultraviolet irradiation (Schulze-Lefert, et al., 1989 *EMBO J.* 8:651); a *Z. mays* alcohol dehydrogenase gene promoter induced under anaerobic conditions (Walker, et al., 1987, *Proc. Natl. Acad. Sci. USA* 84:6624); and a promoter induced by salt stress (Shinozaki, K. and Yamaguchi-Shinozaki, K., *Curr. Opin. Plant Biol.* 3, 217-223 (2000)).

(3) Vector

The present invention provides a vector comprising the above-described construct. In other words, this invention provides a vector comprising an operably linked promoter and the inventive nucleic acid.

The vector can be prepared simply by liking a recombination vector available in the art to a desired nucleic acid according to a common procedure. A plant transformation vector is particularly useful to increase plant biomass using the nucleic acid of the present invention. The vector used in this invention is not particularly limited as long as it can be used to achieve the intended effects of this invention in plant cells, and for example, pBI vectors, pBluescript vectors, and pUC vectors can be used. Examples of pBI vectors include, but are not limited to, pBI121, pBI101, pBI101.2, pBI101.3, and pBI221. Binary vectors such as pBI vectors are preferable in that they can introduce an intended nucleic acid to a plant via *Agrobacterium*. Examples of pBluescript vectors include, but are not limited to, pBluescript SK(+), pBluescript SK(−), pBluescript II KS(+), pBluescript II KS(−), pBluescript II SK(+), and pBluescript II SK(−). Examples of pUC vectors include, but are not limited to, pUC19 and pUC119. pBluescript and pUC vectors are preferable in that they can directly introduce a nucleic acid to a plant. Further, binary vectors such as pGreen series (www.pgreen.ac.uk) and pCAMBIA series (www.cambia.org), and superbinary vectors such as pSB11 (Komari, et al., 1996, *Plant J*, 10: 165-174) and pSB200 (Komori, et al., 2004, *Plant J*, 37: 315-325) can be preferably used.

It is preferred that the above-described vector comprise a transcription terminator sequence containing a polyadenylation site required for stabilization of a transcript. Those skilled in the art can select an appropriate transcription terminator sequence.

The transcription terminator sequence is not particularly limited as long as it functions as a transcription termination site, and the transcription terminator sequence can be a known one. The transcription terminator sequence can be selected depending on the promoter to be used, and for example, cauliflower mosaic virus 35S transcription termination region (CaMV35S terminator) and nopaline synthase gene transcription termination region (Nos terminator) can be used. By locating the transcription terminator sequence at an appropriate position in the above-described recombinant expression vector, the occurrence of a phenomenon in which an unnecessarily long transcript is synthesized after the vector is introduced in a plant cell can be prevented.

The above-described recombinant expression vector may also contain other nucleic acid segments. Such other nucleic acid segments are not particularly limited and can be exemplified by transformant selection markers, enhancers, and nucleotide sequences for enhancing translation efficiency. The aforementioned recombinant expression vector may further have a T-DNA region. The T-DNA region is capable of enhancing gene introduction efficiency particularly when the aforementioned recombinant expression vector is introduced into a plant using *Agrobacterium*.

As the transformant selection markers, drug resistance genes, for example, can be used. Specific examples of such drug resistance genes include, but are not limited to, drug resistance genes against hygromycin, bleomycin, kanamycin, gentamicin, or chloramphenicol (e.g., neomycin phosphotransferase gene which is resistant to the antibiotic kanamycin or gentamicin; hygromycin phosphotransferase gene which is resistant to hygromycin). Also, phosphinothricin acetyltransferase gene which is resistant to the herbicide phosphinothricin can be used. Thus, by selecting a plant that grows in a medium containing any of the aforementioned antibiotics or herbicide, a transformed plant can be easily picked up.

The nucleotide sequences for enhancing translation efficiency can be exemplified by the omega sequence derived from tobacco mosaic virus. By locating the omega sequence in an untranslated region (5'UTR) of a promoter, translation efficiency of the aforementioned fusion genes can be enhanced.

The enhancers can be exemplified by enhancer regions comprising an upstream sequence of the CaMV35S promoter. As described above, various nucleic acid segments can be included in the aforementioned recombinant expression vector depending on the purpose.

Also, a method for constructing the recombinant expression vector is not particularly limited, and it is only sufficient to introduce the nucleic acid, promoter, and terminator sequence of the present invention, and optionally other DNA segments, in a prescribed order in a vector appropriately selected as a matrix. Insertion of a nucleic acid into a vector as a matrix is performed by using, for example, a method in which a purified nucleic acid is cleaved with an appropriate restriction enzyme and the cleaved nucleic acid is inserted into a restriction enzyme site or multicloning site in an appropriate vector according to a common procedure (e.g., *Molecular Cloning*, 5.61-5.63).

Those skilled in the art can appropriately prepare a vector harboring a desired gene according to a common genetic engineering technique. Such a vector can generally be prepared easily by using various types of commercially available vectors.

(4) Host Cell

The present invention provides a host cell comprising the above-described vector (or in other words, a host cell having introduced therein the nucleic acid of this invention).

The host cell of the present invention is not particularly limited but is preferably a plant cell. Examples of the host cell include various forms of plant cells, such as suspension-cultured cells, protoplasts, and cells in plants.

The plant cell is not particularly limited, and cells derived from a dicotyledonous plant or a monocotyledonous plant can be used. Examples of the dicotyledonous plant include, but are not limited to, *Arabidopsis thaliana, Glycine max, Gossypium arboretum, Brassica napus, Beta vulgaris, Nicotiana tabacum, Solanum lycopersicum, Raphanus sativus, Vitis vinifera*, and *Populus trichocarpa*. Among them, *A. thaliana, G. max, G. arboretum, B. napus, N. tabacum*, and *S. lycopersicum* are preferred, with *A. thaliana, G. max, G. arboretum*, and *B. napus* being more preferred. Examples of the monocotyledonous plant include, but are not limited to, *Oryza sativa, Zea mays, Triticum aestivum, Hordeum vulgare, Sorghum bicolor, Saccharum officinarum*, and *Allium cepa*. Among them, *O. sativa, Z. mays, T. aestivum*, and *Sorghum bicolor* are preferred, with *O. sativa* and *Z. mays* being more preferred.

Likewise, as for the nucleic acid of the present invention, nucleic acids derived from various plant species can be used. In this invention, the plant species from which the nucleic acid is derived may be the same or different from that from which the host cell (plant cell) is derived. In other words, this invention can provide both of a host cell (plant cell) having introduced therein either a nucleic acid derived from the same plant species as that from which said host cell is derived or a vector comprising said nucleic acid, and a host cell (plant cell) having introduced therein either a nucleic acid derived from a different plant species from that from which said host cell is derived or a vector comprising said nucleic acid. Also, in this invention, when the plant from which the nucleic acid is derived is a dicotyledonous plant, a host cell from a dicotyledonous plant may be selected, or when the plant from which the nucleic acid is derived is a monocotyledonous plant, a host cell from a monocotyledonous plant may be selected.

A method for expressing a nucleic acid of interest in the host cell can be exemplified by methods in which the nucleic acid is incorporated in an appropriate vector and the vector is introduced into a living organism by a method known to those skilled in the art, such as polyethylene glycol method, *Agrobacterium* method, liposome method, cationic liposome method, calcium phosphate precipitation method, electric pulse perforation method (electroporation) (*Current Protocols in Molecular Biology*, edit. Ausubel, et al., (1987), Publish. John Wiley & Sons., Sections 9.1 to 9.9), lipofection method (GIBCO-BRL), microinjection method, or particle gun method. In the present invention, the *Agrobacterium* method can be preferably used. When a nucleic acid is introduced into a plant cell, the nucleic acid may be directly introduced using the microinjection method, the electroporation method, the polyethylene glycol method, or the like, or may be indirectly introduced into the plant cell through a virus or bacterium having an ability to infect plants, by incorporating the nucleic acid in a plasmid for gene introduction in plants and using the plasmid as a vector. Typical examples of such a virus include, but are not limited to, cauliflower mosaic virus, tobacco mosaic virus, and geminivirus, and examples of such a bacterium include, but are not limited to, *Agrobacterium*. When gene introduction into a plant is performed by the *Agrobacterium* method, a commercially available plasmid can be used.

(5) Transformed Plant

The present invention provides a plant having the above-described vector introduced therein (or in other words, a plant having the nucleic acid of this invention introduced therein). When the host cell of this invention is a plant cell, the plant cell is included by the plant (transformed plant) of this invention. The plant of this invention includes not only such a plant cell, but also the whole of a plant, plant organs (e.g., root, stem, leaf, petal, seed, fruit, mature embryo, immature embryo, ovule, ovary, shoot apex, anther, pollen), plant tissues (e.g., epidermis, pholoem, parenchyma, xylem, vascular bundle), segments thereof, callus, shoot primordia, seedling, multiple shoot, hairy root, cultured root, and the like.

The plant of the present invention is a dicotyledonous plant or a monocotyledonous plant. Examples of the dicotyledonous plant include, but are not limited to, *Arabidopsis thaliana, Glycine max, Gossypium arboretum, Brassica napus, Beta vulgaris, Nicotiana tabacum, Solanum lycopersicum, Raphanus sativus, Vitis vinifera*, and *Populus trichocarpa*. Among them, *A. thaliana, G. max, G. arboretum, B. napus, N. tabacum, and S. lycopersicum* are preferred, with *A. thaliana, G. max, G. arboretum*, and *B. napus* being more preferred. Examples of the monocotyledonous plant include, but are not limited to, *Oryza sativa, Zea mays, Triticum aestivum, Hordeum vulgare, Sorghum bicolor, Saccharum officinarum*, and *Allium cepa*. Among them, *O. sativa, Z. mays, T. aestivum*, and *S. bicolor* are preferred, with *O. sativa* and *Z. mays* being more preferred.

As in the case of the host cell described above, the species of the plant of the present invention may be the same as or different from the plant species from which an introduced nucleic acid is derived. In other words, this invention can provide both of a plant having introduced therein either a nucleic acid derived from the same species of plant or a vector comprising said nucleic acid (i.e., a plant having introduced therein a nucleic acid or a vector comprising said nucleic acid, wherein the species of said plant is the same as the plant species from which said nucleic acid is derived), and a plant having introduced therein either a nucleic acid derived from a different species of plant or a vector comprising said nucleic acid (i.e., a plant having introduced therein a nucleic acid or a vector comprising said nucleic acid, wherein the species of said plant is different from the plant species from which said nucleic acid is derived). Also, in this invention, when the plant from which the nucleic acid is derived is a dicotyledonous plant, the plant into which the nucleic acid is introduced can be a dicotyledonous plant, or when the plant from which the nucleic acid is derived is a monocotyledonous plant, the plant into which the nucleic acid is introduced can be a monocotyledonous plant.

The present invention can provide the following plants:
(i) a monocotyledonous plant having introduced therein a nucleic acid derived from a monocotyledonous plant or a vector comprising said nucleic acid;
(ii) a monocotyledonous plant having introduced therein a nucleic acid derived from a dicotyledonous plant or a vector comprising said nucleic acid;
(iii) a dicotyledonous plant having introduced therein a nucleic acid derived from a dicotyledonous plant or a vector comprising said nucleic acid;
(iv) a dicotyledonous plant having introduced therein a nucleic acid derived from a monocotyledonous plant or a vector comprising said nucleic acid.

Among them, preferred are:

(i) a monocotyledonous plant having introduced therein a nucleic acid derived from a monocotyledonous plant or a vector comprising said nucleic acid;

(ii) a monocotyledonous plant having introduced therein a nucleic acid derived from a dicotyledonous plant or a vector comprising said nucleic acid; and (iii) a dicotyledonous plant having introduced therein a nucleic acid derived from a dicotyledonous plant or a vector comprising said nucleic acid.

More preferred are:

(i) a monocotyledonous plant having introduced therein a nucleic acid derived from a monocotyledonous plant or a vector comprising said nucleic acid; and (ii) a monocotyledonous plant having introduced therein a nucleic acid derived from a dicotyledonous plant or a vector comprising said nucleic acid.

The plant of the present invention includes a plant obtained by growing a plant cell having introduced therein the nucleic acid of this invention or a vector comprising said nucleic acid, and a plant which is the progeny, offspring or clone of said plant, and their reproductive materials (e.g., seed, fruit, cut panicle, tuber, root tuber, stock, callus, protoplast). Reproduction of a plant from a transformed plant cell can be done by a method known to those skilled in the art depending on the type of the plant cell. The techniques of reproduction have been established and widely used in the technical field of this invention. These techniques can be suitably used in this invention.

A method for regenerating a transformed plant cell to reproduce a plant varies with the type of the plant cell. For example, the method of Fujimura, et al. (*Plant Tissue Culture Lett.* 2:74 (1995)) is used for *Oryza sativa*, and the methods of Shillito, et al. (*Bio/Technology* 7:581 (1989)) and Gorden-Kamm, et al. (*Plant Cell* 2:603 (1990)) are used for *Zea mays*. The presence of a foreign nucleic acid introduced into a transformed plant which is reproduced by such a method as mentioned above and is planted can be determined by the known PCR method or Southern hybridization method, or by analysis of a DNA nucleotide sequence in the plant. In such a case, DNA extraction from the transformed plant can be done by following the known method of J. Sambrook, et al. (*Molecular Cloning,* 2nd ed., Cold Spring Harbor Laboratory Press, 1989).

For example, when a foreign nucleic acid present in a reproduced plant is analyzed by PCR, an amplification reaction is performed using as a temperate a DNA extracted from the reproduced plant in such a manner as above. Alternatively, it is also possible that synthesized oligonucleotides having nucleotide sequences appropriately selected according to the nucleotide sequence of the nucleic acid of the present invention or an altered nucleic acid are used as primers, and an amplification reaction is done in a reaction liquid having a mixture of said primers. In an amplification reaction, an amplified product of a DNA fragment comprising the nucleotide sequence of a nucleic acid of interest can be obtained by repeating a cycle of DNA denaturation, annealing, and extension a few dozen times. When a reaction liquid containing an amplified product is subjected to, for example, agarose electrophoresis, amplified DNA fragments are separated, so that it can be confirmed that the DNA fragments correspond to the genes of this invention.

Once a transformed plant having a nucleic acid of interest introduced in the genome is obtained, an offspring can be produced from the plant by sexual or asexual reproduction. Also, a reproductive material is obtained from the plant or the offspring or clone thereof, and the plant can be mass produced based on said reproductive material. The present invention covers a plant cell having introduced therein either the nucleic acid of this invention or a recombinant expression vector comprising said nucleic acid, a plant comprising said cell, an offspring and clone of said plant, and a reproductive material from said plant and its offspring and clone. In other words, this invention covers "T0 generation" plants which are initial regenerated transgenic plants, and their progeny plants such as "T1 generation" plants which are seeds from T0 generation plants, as well as hybrid plants created by crossing those different generation plants, each of which is used as one parent, and progeny plants from said hybrid plants.

The plant (transformed plant) of the present invention also includes so-called "site-specific transformants" in which the native promoter controlling the bil7 gene of wild-type plants (including plants having no nucleic acid of this invention (e.g., bil7 gene) introduced from the outside) is replaced by any of the aforementioned promoters. Such plants are characterized in that the biomass is increased by enhanced expression of the bil7 gene inherent in the plants caused by the replaced promoter. This invention also covers, in one embodiment, plants in which the specified nucleic acid (e.g., bil7 gene) is eventually strongly expressed (overexpressed); thus, such site-specific transformants can also be included within the scope of this invention. As a method for preparing such plants, various known genome editing techniques such as CRISPR method, ZFN method, and TAL effector nuclease (TALEN) method can be used.

The thus-prepared transformed plants are expected to have an advantageous characteristic in that the biomass is increased relative to ordinary plants. The plant used as a target for transformation in the present invention is not particularly limited, and various species of transformed plants with increased biomass can be prepared by the method of this invention.

(6) Method for Increasing Plant Biomass

The present invention provides a method for increasing plant biomass comprising the step of introducing the above-described nucleic acid into a plant. More specifically, the method of this invention is a method for increasing plant biomass, comprising the steps of: preparing a vector comprising the nucleic acid of this invention and a promoter operably linked to said nucleic acid; introducing said vector into a host cell (plant cell); and reproducing a plant from the plant cell having said nucleic acid introduced therein. The method of this invention can be obtained by utilizing a plant biomass increasing activity of the protein encoded by the nucleic acid of this invention.

In the method of the present invention, the above-described nucleic acid, or instead a vector comprising said nucleic acid can be introduced into a plant. Introduction of the inventive nucleic acid or a vector comprising said nucleic acid into a plant is done by a method as described above; the nucleic acid can be introduced into a plant through introduction of the nucleic acid into a host cell (plant cell). Also, the type of the plant used as a target in the method of this invention, the relationship of said plant with the plant species from which the introduced nucleic acid is derived, and other conditions are as described above. In addition, the terms, materials, techniques and other matters that should be considered in relation to the inventive method are understood in accordance with the descriptions and definitions given hereinabove.

(7) Method for Preparing a Plant with Increased Biomass

The present invention provides a method for preparing a plant with increased biomass, comprising the step of introducing the above-described nucleic acid into a plant. More specifically, the method of this invention is a method for preparing a plant with increased biomass, comprising the steps of: preparing a vector comprising the nucleic acid of this invention and a promoter operably linked to said nucleic acid; introducing said vector into a host cell (plant cell); and reproducing a plant from the plant cell having said nucleic acid introduced therein. The method of this invention can be obtained by utilizing a plant biomass increasing activity of the protein encoded by the nucleic acid of this invention.

In the method of the present invention, the above-described nucleic acid, or instead a vector comprising said nucleic acid can be introduced into a plant. Introduction of the nucleic acid or a vector comprising said nucleic acid into a plant is done by a method as described above; the nucleic acid can be introduced into a plant through introduction of the nucleic acid into a host cell (plant cell). Also, the type of the plant used as a target in the method of this invention, the relationship of said plant with the plant species from which the introduced nucleic acid is derived, and other conditions are as described above. In addition, the terms, materials, techniques and other matters that should be considered in relation to the inventive method are understood in accordance with the descriptions and definitions given hereinabove.

(8) Method for Screening for a Plant with Increased Biomass

The present invention provides a method for screening for a plant with increased biomass using the above-described protein or nucleic acid. This method comprises the following steps:
(1) measuring the expressions levels of the protein of this invention or a nucleic acid encoding said protein in test and wild-type plants;
(2) comparing the expressions levels obtained at step (1); and
(3) selecting the test plant whose expression level is higher than that in the wild-type plant.

As described above, the morphology of the plant used as a target in the screening method of the present invention includes not only a plant cell, but also the whole of a plant, plant organs (e.g., root, stem, leaf, petal, seed, fruit, mature embryo, immature embryo, ovule, ovary, shoot apex, anther, pollen), plant tissues (e.g., epidermis, pholoem, parenchyma, xylem, vascular bundle), segments thereof, callus, shoot primordia, seedling, multiple shoot, hairy root, cultured root, and the like. From the viewpoint of screening, it is particularly preferred that the plant be in a state before growing into maturity or in a juvenile state. Thus, seed (mature seed, immature seed), mature embryo, immature embryo, callus, shoot, seedling, and the like are particularly preferred morphology of the plant in the inventive screening method.

As referred to herein, the "wild-type plant" is a phenotype of line or plant most frequently found among target plants, and mainly refers to a plant species that is not genetically modified at all. The morphology of the wild-type plant can be any of the morphology mentioned above, but is preferably the same as the morphology of a test plant.

Measurement of protein or nucleic acid expression level can be conducted by using a well-known method in the art. For example, the expression level of a protein can be measured by extracting a protein from a plant, preparing or obtaining an antibody against the protein of the present invention (e.g., BIL7 protein from different species of plants), and performing western blotting, immunoassay (e.g., ELISA) or any other methods pursuant thereto using said antibody. The antibody used can be either a monoclonal antibody or a polyclonal antibody. Also, the antibody can be an antibody molecule per se or a fragment thereof, such as Fab, Fab', or F(ab')$_2$. As a label for the antibody, a radioisotope, an enzyme, a fluorescent substance, a luminescent substance, or the like, which are per se known, is used. The expression level of a nucleic acid can be measured by, for example, extracting RNA from a plant, preparing or obtaining primers capable of specifically amplifying the nucleic acid of the present invention, or probes capable of specifically detecting said nucleic acid, based on the nucleotide sequence of said inventive nucleic acid (e.g., BIL7 gene from different species of plants), and performing RT-PCR, Northern blotting, or any other methods pursuant thereto using said primers or probes.

The expression level of a protein or a nucleic acid can be qualitative or quantitative, but is preferably quantified as a numerical value (measured value). The expression levels obtained from test and wild-type plants are mutually compared, and when the expression level in the test plant is higher than that in the wild-type plant, it can be determined that plant biomass is increased. By selecting such a test plant, screening for a plant with increased plant biomass can be done.

(9) Method for Verifying a Plant with Increased Biomass

The present invention provides a method for verifying a plant with increased biomass using the above-described protein or nucleic acid. This method comprises the following steps:
(1) measuring the expressions levels of the protein of this invention or a nucleic acid encoding said protein in test and wild-type plants;
(2) comparing the expressions levels obtained at step (1); and
(3) confirming that the expression level in the test plant is higher than that in the wild-type plant.

The verification method of the present invention is synonymous with the use of the protein or nucleic acid of this invention as a marker (protein marker or nucleic acid marker). In other words, when the protein or nucleic acid of this invention is detected in a plant of interest and also the expression level of the inventive protein or nucleic acid in said plant is higher than that in a wild-type one, said plant of interest is expected to have increased biomass.

The morphology of the plant used as a target in the verification method of the present invention has been described above in relation to the screening method, and all plant parts and the like as listed above are likewise included by the morphology of the plant used in the verification method, but it is particularly preferred that the plant be in a state before growing into maturity or in a juvenile state. Thus, seed (mature seed, immature seed), mature embryo, immature embryo, callus, shoot, seedling, and the like are particularly preferred morphologys of the plant in the inventive verification method.

Measurement of protein or nucleic acid expression level in the inventive verification method can be conducted by using a well-known method in the art. A specific example of such a well-known method has been described above in relation to the screening method. In this invention, the expression level of a protein or a nucleic acid can be qualitative or quantitative, but is preferably quantified as a numerical value (measured value). The expression levels obtained from test and wild-type plants are mutually compared, and when the expression level in the test plant is confirmed to be higher than that in the wild-type plant, it can be determined that plant biomass is increased.

EXAMPLES

Hereunder, the present invention will be specifically described by way of working examples, but these examples are not intended to limit the technical scope of this invention. Those skilled in the art can easily make any alterations or modifications to this invention based on the descriptions in the present specification, and such alterations and modifications are also included in the technical scope of this invention.

Example 1 Selection of a Bil7 Mutant

The FOX hunting system (Full-length cDNA Over-expression Gene Hunting System) is a method for identifying the functions of DNA based on changes in characters caused by introduction and strong expression of a full-length cDNA in a plant (WO 03/018808). In this example, from among about 8,800 Arabidopsis (Arabidopsis thaliana) FOX lines (Ichikawa, et al., 2006), selection was made of plant lines exhibiting a bil (Brz-insensitive-long-hypocotyl) morphology in which hypocotyl elongates relative to wild-type Arabidopsis (A. thaliana) in the presence of the brassinosteroid (BR) biosynthesis inhibitor brassinazole (Brz) in the dark. Plants exhibiting a bil morphology in the presence of Brz in the dark are believed to have Brz resistance. The selection consisted of primary and secondary selections. The selected lines were back-crossed to the wild-type, and the thus-created hybrid F1 generation plants were confirmed to exhibit a bil morphology in the presence of Brz in the dark, thereby it was confirmed that bil mutation is a dominant character. Since FOX lines are gain-of-function mutants, the dominant mutation was considered to indicate that the cause of the mutation originates from FOX.

Figure 1:
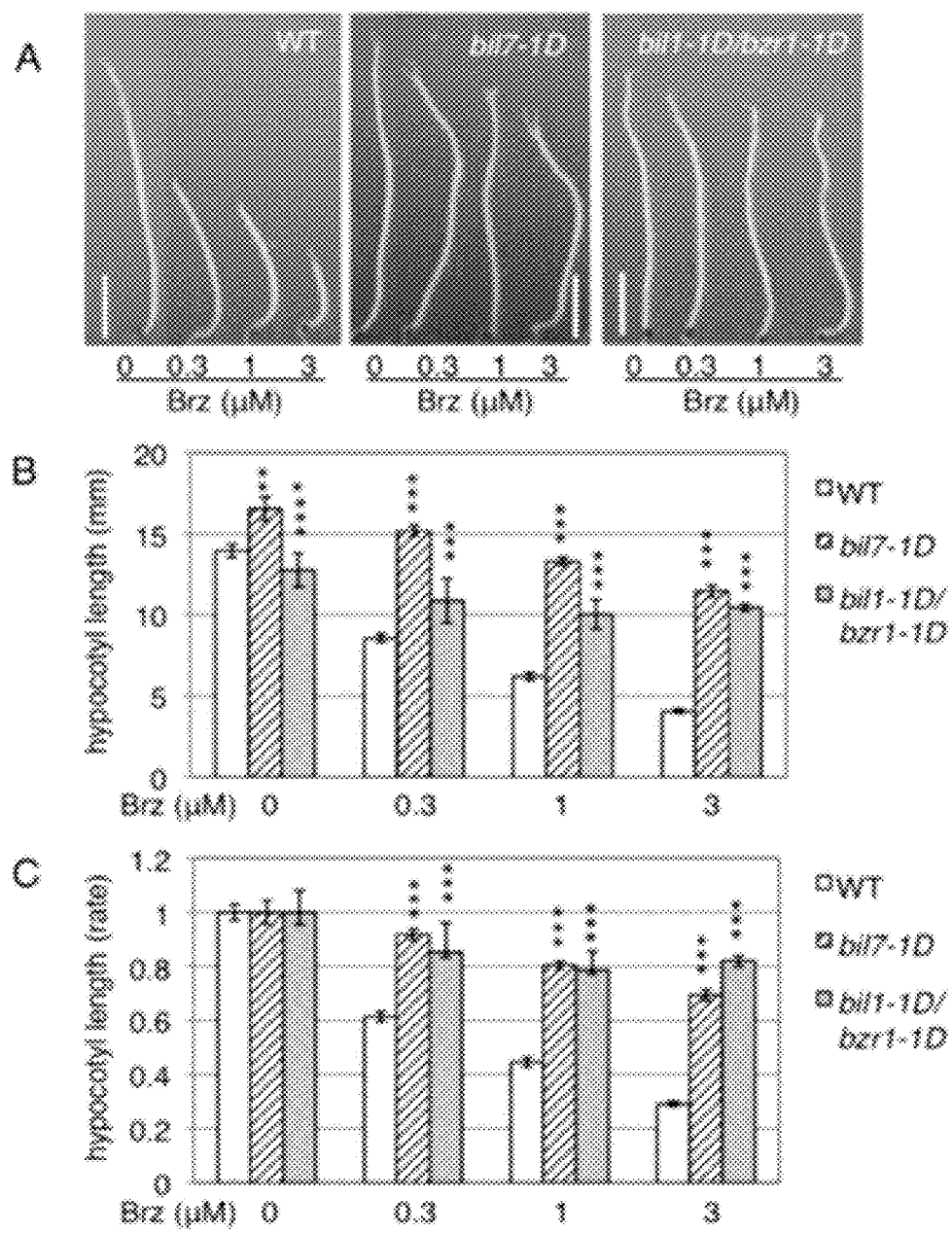

First, seeds of 20 to 40 FOX lines were mixed and grown under the conditions of germination in the presence of 3 µM Brz in the dark, and hypocotyl elongation lines were primarily selected. Then, after the primarily selected plants were grown, the obtained seeds were grown again under the conditions of germination in the presence of 3 µM Brz in the dark and hypocotyl elongation lines were secondarily selected. Additionally, in the secondary selection, the lines divided into one-fourth with a strong bil morphology, two-fourths with a moderate bil morphology, and the other one-fourth with a comparable bil morphology to the wild-type; thus, it was confirmed that bil mutation is a dominant character. As a result of this secondary selection, several lines of candidate mutants apparently exhibiting more significant hypocotyl elongation than wild-type Columbia-0 (Col-0) were obtained. Among them, line No. 72 which exhibited the longest hypocotyl elongation morphology was named as bil7-1D (Brz-insensitive-long-hypocothl 7-1D) and used as a target for analysis. The hypocotyl elongation of bil7-1D in the presence of 3 µM Brz in the dark was about 2.5 times longer than that of the wild-type, and was considered as a strong Brz-resistant mutant character comparable to bil1-1D/bzr1-1D (positive control with Brz resistance) which is a gain-of-function mutant of BIL1/BZR1, a master transcription factor for BR signaling (FIG. 1).

Figure 2:
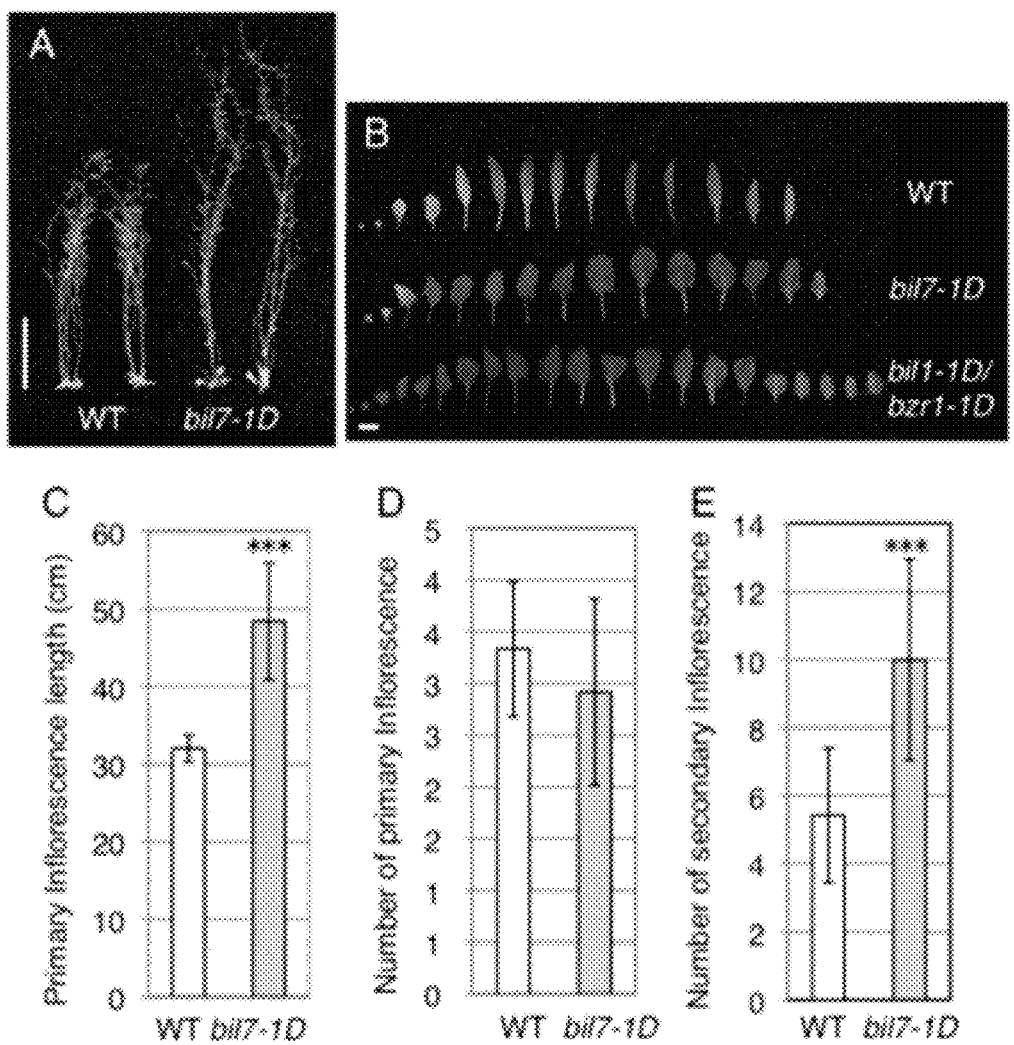

For the purpose of analyzing the morphological features of bil7-1D, morphological observation for maturity was conducted. A mature bil7-1D mutant plant on day 60 which seemed to stop growing was morphologically analyzed, and the results found that the inflorescence of bil7-1D elongated about 1.5 times longer than the wild-type (FIGS. 2A, C). It was also found that the number of primary inflorescences for bil7-1D was similar to that for the wild-type but that the number of secondary inflorescences for bil7-1D increased about twice (FIGS. 2D, E). The rosette leaves of bil7-1D were more rounded than those of the wild-type and similar to those of bil1-1D/bzr1-1D (FIG. 2B).

Figure 3:
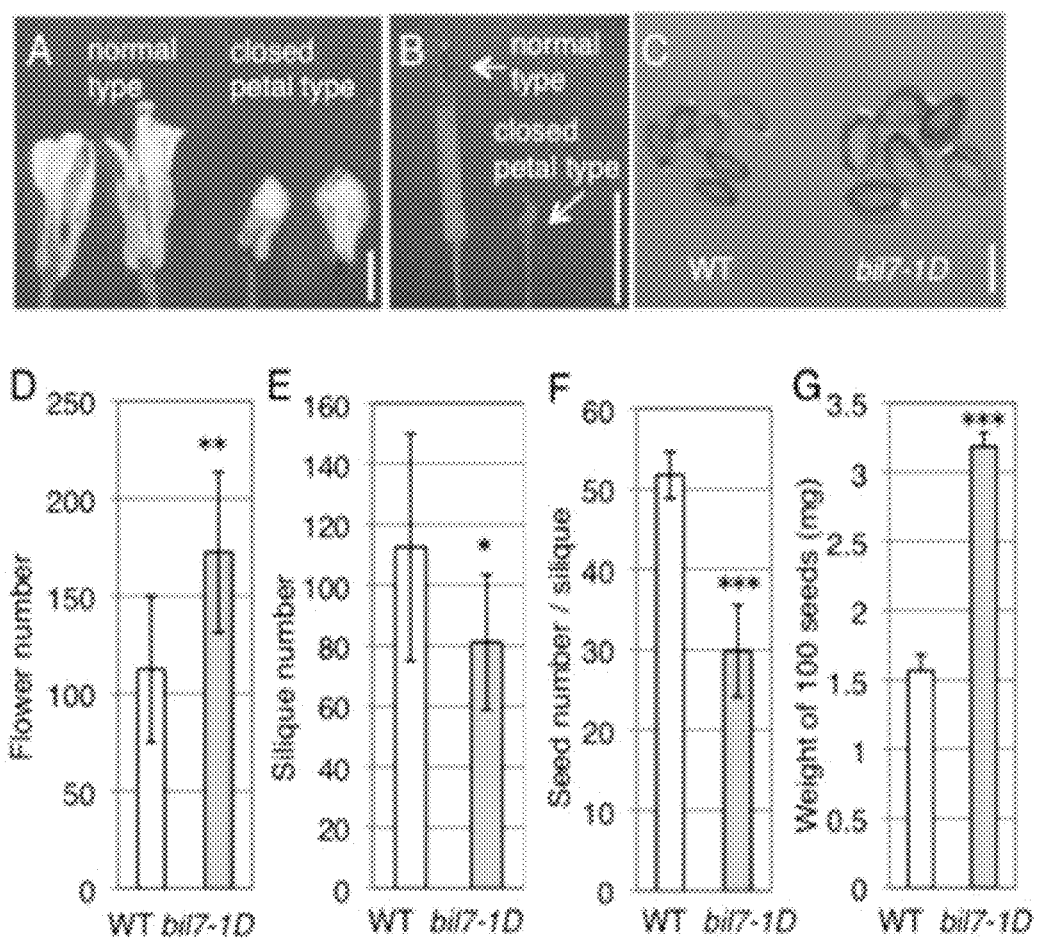

Further, analysis of reproductive organs was conducted. In not all but about 45% of the flowers of bil7-1D, it was observed that flower petals did not open normally (FIG. 3A) and so no normal siliques were produced even after flowers were formed (FIG. 3B). Thus, in bil7-1D, relative to the wild-type, the number of flowers increased but the number of normal siliques decreased (FIGS. 3D, E). Also, the number of seeds per silique in bil7-1D decreased, thereby resulting in a decrease in the total number of seeds (FIG. 3F). The seeds of bil7-1D grew larger than the wild-type ones (FIG. 3C), and the weight of seeds of bil7-1D increased about twice as compared to that of the wild-type (FIG. 3G).

Figure 4:
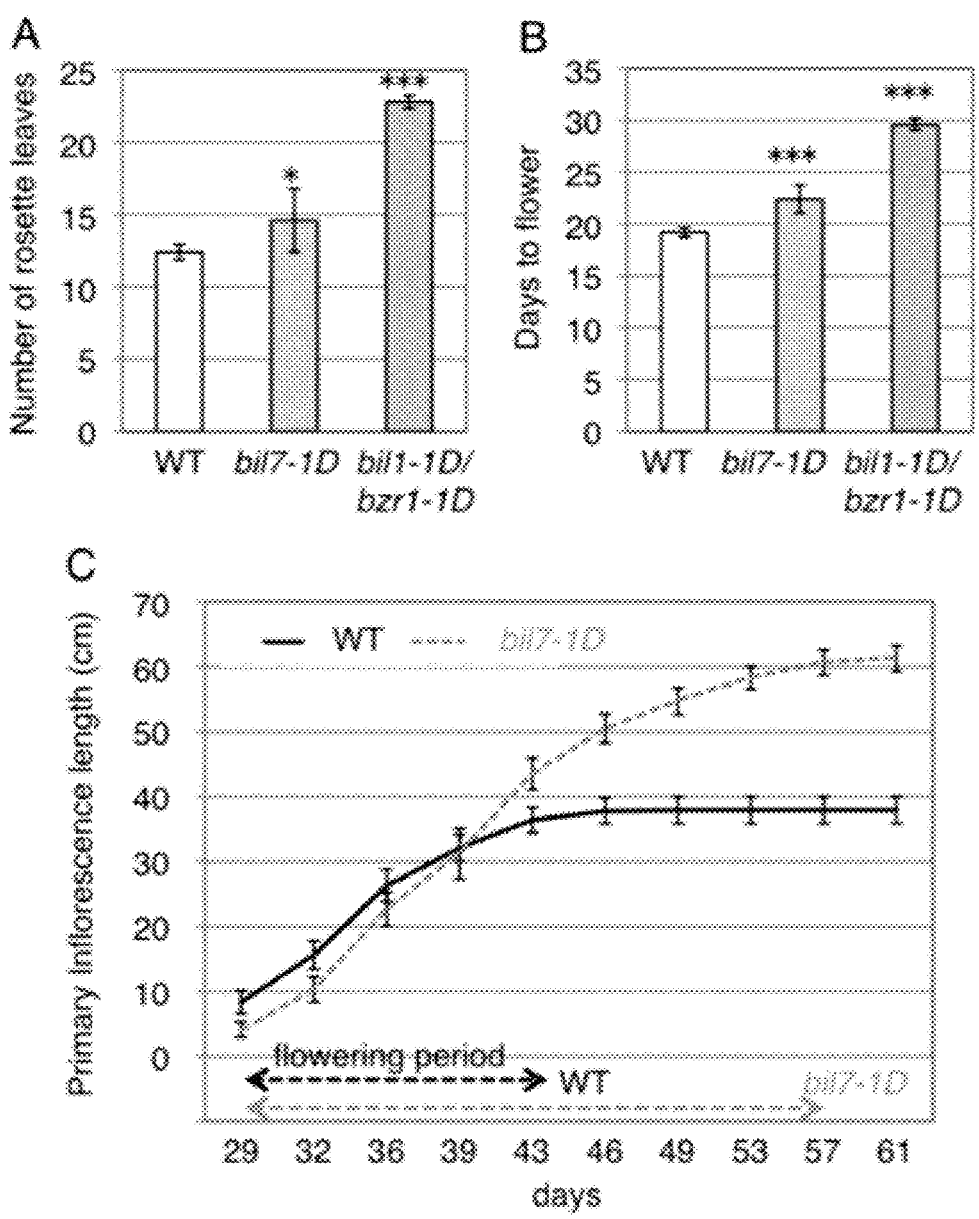

As a result of analysis of the growth process of bil7-1D, it was considered that although bil7-1D tends to be slightly delayed in flowering (FIG. 4A) and growth (FIG. 4B), there is no significant difference between bil7-1D and the wild-type in view of the values for bil1-1D/bzr1-1D which is reported as a delayed-flowering mutant (Zhang, et al., 2013). According to temporal observation, bil7-1D and the wild-type are similar in the rate of inflorescence elongation, but in the wild-type, the flowering period ended and inflorescence elongation ceased on about day 45 after seeding, whereas the flowering period and inflorescence elongation in bil7-1D continued until about day 60 (FIG. 4C). These results revealed that bil7-1D exhibits significant growth-promoting morphological characters related to inflorescence elongation.

Example 2 Isolation and Identification of Bil7-1D Mutant Causative Gene

Based on the morphological analysis of the bil7-1D plant, it was presumed that the mutant causative gene BIL7 is capable of inducing growth-promoting morphological characters such as inflorescence elongation and activating BR signaling. Thus, the bil7-1D mutant causative gene BIL7 was isolated and subjected to homologous protein analysis and functional domain search. Then, it was confirmed that the morphology of bil7-1D was reproduced by preparing a high BIL7-expressing transformant (BIL7-OX) and highly expressing the BIL7 candidate gene; thus, the BIL7 gene was established.

2-1 Isolation of Bil7-1D Mutant Causative Gene

As for the cDNA introduced in the bil7-1D mutant, the genome of the mutant was used as a template, and PCR and sequencing were performed with primers specific for 35S CaMV promoter and NOS terminator to obtain gene fragments.

Rosette leaves were collected from the bil7-1D mutant, and genomic DNA was extracted from the collected leaves using the Nucleon DNA Extraction Kit (Amersham). Then, PCR was performed on the extracted DNA. The PCR solution, reaction conditions, and primers are as mentioned below.

TABLE 3

| | (PCR cycle) | (Components of PCR solution) | |
|---|---|---|---|
| 1 | 95° C. 3 min | DNA template | 1 µL |
| 2 | 94° C. 30 sec | 10 × EX Taq buffer | 3 µL |
| 3 | 63.1° C. 30 sec | dNTP mix | 3 µL |
| 4 | 72° C. 4 min | primerF | 0.2 µL |

TABLE 3-continued

| (PCR cycle) | | (Components of PCR solution) | |
|---|---|---|---|
| | <#2-4 × 40> | primerR | 1 μL |
| 5 | 72° C. 5 min | EX Taq | 1 μL |
| 6 | end | dH₂O | 21.6 μL |
| | | Total | 30 μL |

TABLE 4

Primer set:

| Forward primer (5'-3') | | Reverse primer (5'-3') | |
|---|---|---|---|
| FOX-F1 | GGAAGTTCATTTATTCGGAGAG (SEQ ID NO: 28) | FOX-F2 | GGCAACAGGATTCAATCTTAAG (SEQ ID NO: 29) |

The nucleotide sequence of the thus-obtained PCR product was sequenced, and as a result, a gene encoding a novel protein with unknown function was presented as BIL7 candidate gene.

The expression of the BIL7 candidate gene was analyzed by realtime RT-PCR. Total RNA was extracted from the plant using the RNeasy Plant Mini Kit (QIAGEN). Then, a reaction solution was prepared using the Takara PrimeScript RT Reagent Kit (Perfect Realtime), and cDNA was synthesized in a cDNA reaction (started at 37° C. for 15 min, followed by at 85° C. for 5 sec, and ended at 4° C.). Using the thus-synthesized cDNA as a template, realtime PCR was done under the following conditions.

TABLE 5

| PCR conditions | | Components of PCR solution | |
|---|---|---|---|
| 1 | 95° C. 30 sec | SYBR Premix Ex Taq ™ II | 12.5 μL |
| 2 | 95° C. 5 sec | 100 μl primer F | 0.1 μL |
| 3 | 60° C. 30 sec | 100 μl primer R | 0.1 μL |
| | <#2-3 × 50> | dH₂O | 7.3 μL |
| | | cDNA | 5.0 μL |
| | | total | 30 μL |

TABLE 6

RT-PCR primer sets

| gene | Forward primer (5'-3') | Reverse primer (5'-3') |
|---|---|---|
| ACT2 | CGCCATCCAAGCTGTTCTC (SEQ ID NO: 30) | TCACGTCCAGCAAGGTCAAG (SEQ ID NO: 31) |
| BIL7 | CATTCGTCTCTCGGGTCCA (SEQ ID NO: 32) | TCTTCGGCGAAGCTGATCTA (SEQ ID NO: 33) |
| BIL7 (for RNAi) | CGAGAAAATTCTCAGACTCAAAGCAGCTGCGTTTATAGTA (SEQ ID NO: 34) | (SEQ ID NO: 35) |
| BIL7-homolog 1 | GGTGGTTTCTGAGTAGTAGTAGTCTCAACGCTGTTATTA (SEQ ID NO: 36) | (SEQ ID NO: 37) |
| BIL7-homolog 2 | GTTATTTGATTGTCGTCGTTTTCTAGACTCAGCGGAGAC (SEQ ID NO: 38) | (SEQ ID NO: 39) |
| BIL7-homolog 3 | CTGTTGAAGAAACCCTACTCACCTTTTCCTCTGATCCT (SEQ ID NO: 40) | (SEQ ID NO: 41) |

Figure 5:
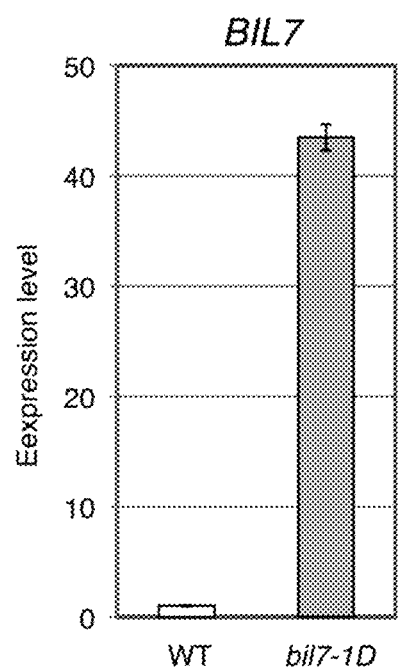
FIG. 5 shows the expression level of the BIL7 candidate gene in bil7-1D on day 7 in the dark. It is evident from this figure that the BIL7 candidate gene is highly expressed in bil7-1D.

As a result, the expression level of the BIL7 candidate gene in bil7-1D increased at least about 40 times as compared to that of the wild-type (FIG. 5). This result, combined with the fact that bil7-1D is a dominant mutant, suggested that overexpression of the BIL7 candidate gene is the cause of bil7-1D phenotype.

2-2 Analysis of the Amino Acid Sequence of the BIL7 Gene

Since the BIL7 candidate gene encodes a protein with unknown function, a motif search against the PROSITE (http://prosite.expasy.org/) and PSORT (http://psort.hgc.jp/form.html) databases and hydrophobicity analysis using GENETYX-MAC were conducted based on the amino acid sequence of BIL7 to estimate the function of the translated product.

The results found that the sequence of BIL7 contains a N-myristoylation predictive site and a N-glycosylation predictive site. No other domain predictive of function was observed. Since no transmembrane domain was found but a nuclear localization signal (NLS) was present, nuclear localization was presumed to occur.

Three different BIL7 homologous proteins were found in Arabidopsis thaliana (thale cress). It was also found that highly homologous proteins are present in other wide variety of plant species, such as Raphanus sativus (radish), Glycine max (soybean), Populus trichocarpa (poplar), Vitis vinifera (grape), Oryza sativa (rice), and Physcomitrella patens. All of these proteins were unreported and novel proteins with unknown function. Further, a particularly highly conservative region was found in these groups of homologous proteins. Based on this region, search for amino acids showing higher homology was conducted, but no protein predictive of function was found. Since the sequence region of the myristoylation predictive site was found to be relatively conservative in other genes, the possibility was suggested that the function of BIL7 may be related to functions shared in common by these proteins.

2-3 Preparation and Morphological Observation of a High BIL7-Expressing Transformant (BIL7-OX)

A construct in which the BIL7 gene was linked downstream of 35S CaMV promoter was transformed into wild-type Arabidopsis (Arabidopsis thaliana) to prepare a high BIL7-expressing transformant (BIL7-OX), which was subjected to morphological observation.

RNA was extracted from rosette leaves of wild-type Arabidopsis (Arabidopsis thaliana) using the RNeasy Plant Mini Kit (QIAGEN). Then, cDNA was synthesized using the SuperScript™ III First-Strand Synthesis System for RT-PCR (Invitrogen) by following the kit protocol. Using this cDNA as a template, PCR was performed with the primers shown below to amplify BIL7.

TABLE 7

Primers for cloning into entry vector (pENTR)

| Sequence | Forward primer | Reverse primer |
| --- | --- | --- |
| BIL7 full length | CCCATGAGAAGCGGTGCTA ATGG (SEQ ID NO: 42) | TTAGCTTAGTGTACCTGAC TG (SEQ ID NO: 43) |

Amplified BIL7 was cloned into an entry vector (pENTR) using the pENTER/D TOPO Cloning Kit (Invitrogen). The prepared pENTR vector was introduced into each of pGWB2 containing a 35S promoter and pGWB80 containing an RNAi construct by Gateway technology using the Gateway LR Clonase II Enzyme Mix (Invitrogen), to obtain BIL7-inserted transformation vectors, pGWB2-BIL7 and pGWB80-BIL7-RNAi.

Then, the prepared vectors were introduced into *Agrobacterium*, which was used to transform wild-type *Arabidopsis* (*Arabidopsis thaliana*) by the flower dipping method.

Two microliters of the prepared vectors were added to 50 μL of *Agrobacterium*-competent cells, and the contents were mixed and left to stand on ice for 30 minutes. After being left in liquid nitrogen for one minute, the mixture was thawed at 37° C. for one minute. 250 μL of a liquid YEP medium was added, and the mixture was cultured at 28° C. for one hour and then spread onto a YEP medium plate supplemented with 50 μg/mL of kanamycin and hygromycin and 100 μg/mL of rifampycin. Colony PCR was performed to determine whether or not the vectors were introduced in *Agrobacterium*.

Figure 6:
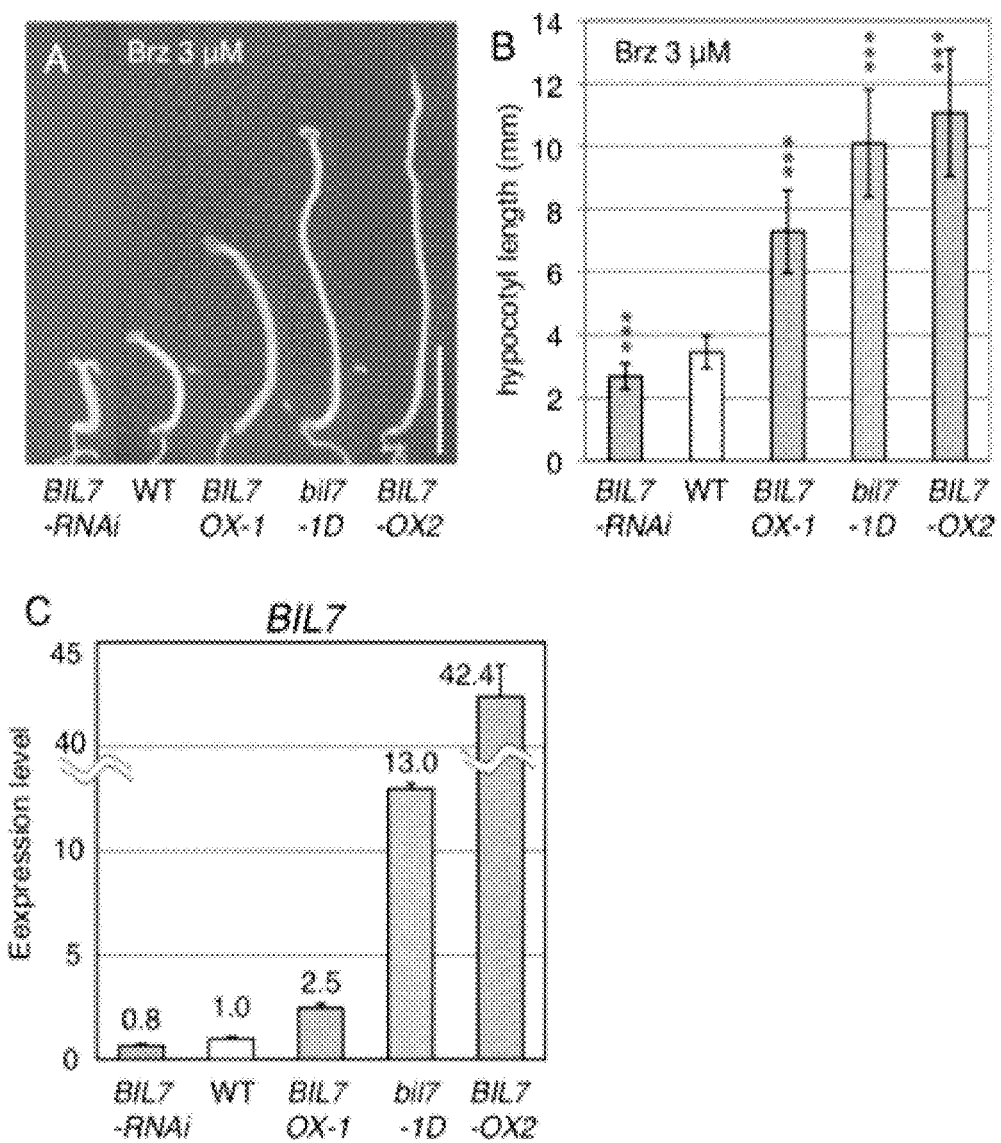
FIG. 6 shows the Brz resistance and BIL7 expression level of a high BIL7-expressing transformant (BIL7-OX)

The *Agrobacterium* colony having the vectors introduced therein was cultured overnight in a liquid YEP medium, and then the culture was scaled up to 500 mL and cultured overnight. The culture was centrifuged at 5000 rpm for 10 minutes to remove the supernatant, and then the remainder was suspended in a MS medium supplemented with 5% (w/v) sucrose. The wild-type with siliques removed was transformed with the suspension by the flower dipping method. The resulting T1 seeds were selected on a MS medium supplemented with 25 μg/mL of kanamycin to obtain a high BIL7-expressing transformant (BIL7-OX) and a BIL7 expression-inhibited transformant (BIL7-RNAi) (FIG. 6).

BIL7-OX lines were examined for the morphological characteristics of bil7-1D as described in Example 1 (FIGS. 7, 8). As a result, the rosette leaf morphology found in bil7-1D was observed not in BIL7-OX1 with low BIL7 expression level but only in BIL7-OX2 with high BIL7 expression level (FIG. 7A). There was a tendency that the length of inflorescence and the number of secondary inflorescences was enhanced in a transformant line with higher BIL7 expression level (FIGS. 7A, B, FIG. 8D). The number of primary inflorescences, which was similar between bil7-1D and the wild-type, tended to slightly decrease with an increase in BIL7 expression (FIG. 8C). With regard to seeds, as the level of BIL7 expression was higher, the number of normal siliques decreased, but the weight of seeds increased as in the case of bil7-1D (FIGS. 8B, E, F).

Hence, all of the mature morphologies observed in bil7-1D were likewise found in the BIL7-OX lines. In view of this, combined with the results of observation of hypocotyl in a Brz-resistant phenotype, it was considered that the morphologies of bil7-1D were reproduced by high expression of the BIL7 candidate gene. From these results, it was established that this gene is a causative gene of bil7-1D.

Example 3 *Oryza sativa* Transformation with OsBIL7, a BIL7 Homologous Gene from *O. sativa*

There was constructed a vector in which the BIL7 homologous gene from *Oryza sativa*, OsBIL7, was ligated downstream of a ubiquitin promoter which is a constitutive expression promoter in *O. sativa*. This vector was used to perform *O. sativa* transformation.

First, the BIL7 homologous gene from *O. sativa*, OsBIL7, was cloned. Total RNA of *O. sativa* Nipponbare wild-type was extracted using Qiagen's RNeasy Plant Kit. Then, from the total RNA, cDNA was synthesized using Invitrogen's SuperScript II Kit. Using this cDNA as a template, PCR was performed with the primers shown below to amplify OsBIL7.

TABLE 8

OsY72-GW-F1:
(SEQ ID NO: 44)
CACCATGCAGAGTGGGAGCGAGAT

OsY72-GW-R1:
(SEQ ID NO: 45)
TTAGCTGACCCCTGGCTGT

Amplified OsBIL7 was cloned using the pENTER/D TOPO Cloning Kit (Invitrogen).

Then, *O. sativa* transformation was performed using the prepared vector. The *O. sativa* variety used was Nipponbare. The above-constructed vector was transformed into *O. sativa* by the high-speed transformation method (Toki, et al., Plant J. 47: 969-76, 2006) via the *Agrobacterium* strain EHA105. The resulting transformed T1 generation and homologous T2 generation were examined for yield characters. As a result, it was found that the number of tillers and seed yield increased in both of T1 generation and homologous T2 generation (FIGS. 9A, B).

Hence, it was confirmed that BIL7 is capable of increasing yield also in *O. sativa*.

Example 4 Biomass Evaluation in Transformants of the *Oryza sativa* Variety Yukihikari in which the OsBIL7 Gene was Overexpressed The vector constructed in Example 3 was transformed into *Oryza sativa* (variety Yukihikari) via the *Agrobacterium* strain LBA4404. At the same time, pSB4 (Komari, et al., 1996, *Plant J.* 10: 165-174) was used as a control and transformed into the plant. The transformation was carried out in accordance with the method of Hiei, et al. (2008, *Plant J.* 6:271-282). The concentration of hygromycin in a selection medium, a regeneration medium, and a rooting medium was 30 μg/mL. An evaluation of the resulting transformants of initial generation (T0 generation) was carried out in a closed greenhouse for genetically modified plants, located in the Plant Innovation Center of Japan Tobacco Inc. The day length was 14.5 hours, and the greenhouse temperature was maintained at 28° C. during the daytime and at 21° C. during the nighttime. After 18 days of transplantation from plant boxes to pots, 36 well-grown seedlings were selected for each transformant, and each one of the 36 seedlings was transplanted to a polypot (12 cm diameter, 830 cc volume). To determine the presence or absence of the introduced genes, PCR assay was made of the OsBIL7 gene and the hygromycin resistance gene. As a result, 4 seedlings were observed to be deficient in the OsBIL7 gene. In contrast, none of the 36 control vector-transformants was deficient in the hygromycin resistance gene. Therefore, data were gathered of the 32 OsBIL7-transformants and the 36 control vector-transformants. The characters measured were culm length, number of tillers, number of panicles, panicle length, number of rough rice per panicle, number of fertile rough rice per panicle, weight of one panicle, panicle weight per plant, upper-ground dry matter weight, and panicle weight per plant. As for culm length, the length of the longest culm was measured. To measure panicle length, number of rough rice per panicle, number of fertile rough rice per panicle, and weight of one panicle, the panicle of the (longest) culm whose length was measured was taken as a sample of measurement. The number of panicles was counted with the exclusion of late-emerging panicles. The harvest was carried out in the order starting with a plant ripened earlier. After completion of the character examination, data were gathered and statistically analyzed. The average values for the different characters are shown in Table 9. FIG. 10 shows seedlings of transformants immediately before being transplanted to polypots. FIG. 11 shows the status of transformants during the maturity period.

TABLE 9

| | Culm length (cm) | Number of tillers | Number of panicles | Panicle length (cm) | Number of rough rice per panicle | Number of rough rice per panicle |
|---|---|---|---|---|---|---|
| OsBIL7 | 65 | 8.9 | 6.9 | 18.4 | 73 | 56 |
| Control vector | 51 | 9.8 | 8.2 | 13.8 | 50 | 36 |

| | Percentage of fertile rough rice (%) | Weight of one panicle (g) | Panicle weight per plant (g) | Upper-ground dry matter weight (g) | Weight of fertile rough rice per plant (g) |
|---|---|---|---|---|---|
| OsBIL7 | 76 | 1.60 | 7.73 | 17.8 | 6.95 |
| Control vector | 73 | 0.94 | 5.73 | 12.8 | 5.15 |

It was found that the OsBIL7 transformants have the following characteristics relative to the control vector-transformed plants. The OsBIL7-transformed plants were higher in culm length by 14 cm, longer in panicle length by 4.6 cm, and larger in number of rough rice per panicle by 23 grains. Since both types of transformants were similar in seed fertility, the number of fertile rough rice per panicle in the OsBIL7-transformants was larger by 20 grains. Also, the OsBIL7-transformants increased in weight of one panicle by 0.66 g (170%) and in panicle weight per plant by 2.00 g (135%). Eventually, said OsBIL7-transformants increased in weight of fertile rough rice per plant, which corresponds to the yield of seeds, by 1.80 g (135%). Further, said OsBIL7-transformants increased in upper-ground dry matter weight by 5.00 g (140%).

To sum up the above, it was found that overexpression of the OsBIL7 gene driven by a ubiquitin promoter in the *O. sativa* variety Yukihikari results in an increase in *O. sativa* upper-ground biomass as well as in the yield of seeds.

Example 5 Biomass Evaluation in *Oryza sativa* Transformants in which *Arabidopsis thaliana* BIL7 Gene was Overexpressed It was examined whether overexpression of *A. thaliana* BIL7 gene in the monocotyledonous plant *O. sativa* leads to an increase in *O. sativa* yield.

The BIL7 gene-cording region of the BIL7 gene cDNA clone (pENTR entry vector) constructed in Example 2 was amplified by PCR and ligated downstream of a ubiquitin promoter in the *O. sativa* transformation binary vector used in Example 3. The primers used in PCR are as shown below.

TABLE 10

| | | |
|---|---|---|
| AtBIL7 GWB1-F1 (SEQ ID NO: 46) | forward | aggatttatcacaagtttgtacaaaaaagcaggctccgc |
| AtBIL7 GWB1-F2 (SEQ ID NO: 47) | forward | gtttggtgttactcctgcaggatttatcacaagtttgtac |
| AtBIL7 GWB1-R1 (SEQ ID NO: 48) | Reverse | caccactttgtacaagaaagctgggtcggcgcgcccaccct tttagcttagtgtacctgactg |
| AtBIL7 GWB1-R2 (SEQ ID NO: 49) | Reverse | ggccgatttggccctgcaggatttatcaccactttgtaca agaaagctgggtc |

The resulting construct Ubi-AtBIL7 was transformed into *O. sativa* (variety Yukihikari) via the *Agrobacterium* strain LBA4404. At the same time, the modified pIG121Hm vector, p121Hm (containing the cassette "CaMV35S promoter-hygromycin resistance gene-NOS terminator" in the T-DNA region) was used as a control and transformed into the plant. The transformation was carried out in accordance with the method of Hiei, et al. (2008, *Plant J.* 6:271-282). The concentration of hygromycin in a selection medium, a regeneration medium, and a rooting medium was 30 μg/mL. An evaluation of the resulting transformants of initial generation (T0 generation) was carried out in a closed greenhouse for genetically modified plants, located in the Plant Innovation Center of Japan Tobacco Inc. The day length was 14.5 hours, and the greenhouse temperature was maintained at 28° C. during the daytime and at 21° C. during the nighttime. After 20 days of transplantation from plant boxes to pots, 36 well-grown seedlings were selected for each transformant, and each one of the 36 seedlings was transplanted to a polypot (12 cm diameter, 830 cc volume). To determine the presence or absence of the introduced genes, all of the 72 transformed plants, including control ones, were subjected to PCR assay of the BIL7 gene and the hygromycin resistance gene. The characters measured were plant length after 5 weeks of transplantation to pots, flag leaf length in the longest culm, culm length, number of panicles, panicle length, number of rough rice per panicle, number of fertile rough rice per panicle, weight of fertile rough rice per panicle, weight of one panicle, panicle weight per plant, upper-ground dry matter weight, and panicle weight per plant. As for culm length, the length of the longest culm was measured. To measure panicle length, number of rough rice per panicle, number of fertile rough rice per panicle, weight of fertile rough rice per panicle, and weight of one panicle, the panicle of the (longest) culm whose length was measured was taken as a sample of measurement. The number of panicles was counted with the exclusion of late-emerging panicles. 1000 fertile rough rice weight was calculated by dividing weight of fertile rough rice per panicle by number of fertile rough rice per panicle and multiplying the resulting quotient by 1000.

The 36 BIL7 transformants were assayed for the presence or absence of the BIL7 gene. As a result, no BIL7 transformant was deficient in the BIL7 gene. Likewise, none of the 36 control vector-transformant was deficient in the hygromycin resistance gene. Therefore, data were gathered of the 36 BIL7 transformants and the 36 control vector transformants. The average values for the different characters are shown in Table 11. FIG. 12 shows the growth status of seedlings immediately before being transplanted to polypots. FIG. 13 shows the status of seedlings during the maturity period.

TABLE 11

| | Plant height (cm) | Flag leaf length (cm) | Culm length (cm) | Number of panicles | Panicle length (cm) | Number of rough rice per panicle | Number of fertile rough rice per panicle |
|---|---|---|---|---|---|---|---|
| BIL7 | 75 | 35 | 62 | 7.4 | 18.6 | 65 | 52 |
| Control vector | 60 | 26 | 49 | 8.0 | 14.4 | 51 | 39 |

| | Percentage of fertile rough rice (%) | 1000-fertile rough rice weight (g) | Weight of one panicle (g) | Panicle weight per plant | Upper-ground dry matter weight (g) | Weight of fertile rough rice per plant (g) |
|---|---|---|---|---|---|---|
| BIL7 | 77 | 26.1 | 1.52 | 7.97 | 17.2 | 7.17 |
| Control vector | 75 | 23.5 | 1.04 | 6.83 | 13.5 | 5.99 |

It was found that the BIL7 transformants have the following characteristics relative to the control vector transformants. After 5 weeks of seeding, the BIL7 transformants were taller in plant length by 15 cm. The BIL7 transformants were longer in flag leaf length by 9 cm, and higher in culm length by 13 cm. Also, said plants were longer in panicle length by 4.2 cm and larger in number of rough rice per panicle by 14 grains. Since both types of plants were similar in seed fertility, the number of fertile rough rice per panicle in the BIL7 transformants was larger by 13 grains. The 1000 fertile rough rice weight of said plants was heavier by 2.6 g. Said plants increased in weight of one panicle by 0.48 g (146%), and in panicle weight per plant by 1.34 g (120%). Eventually, said plants increased in weight of fertile rough rice per plant, which corresponds to the yield of seeds, by 1.18 g (120%). Further, said plants increased in upper-ground dry matter weight by 3.77 g (128%).

To sum up the above, it was found that overexpression of the BIL7 gene driven by a ubiquitin promoter in the *O.* sativa variety Yukihikari results in an increase in *O. sativa* upper-ground biomass as well as in the yield of seeds.

Example 6 Biomass Evaluation in *Zea mays* Transformants in which the OsBIL7 Gene was Overexpressed The vector constructed in Example 3 was transformed into *Zea mays* (inbred line A188) in accordance with the method of Ishida, et al. (2007) via the *Agrobacterium* strain LBA4404. The obtained transformants were planted in a closed greenhouse for genetically modified plants, located in the Plant Innovation Center of Japan Tobacco Inc. The day length was 14.5 hours, and the greenhouse temperature was maintained at 28° C. during the daytime and at 20° C. during the nighttime. The extracted tassels were cut before flowering. Corn silks sufficiently extracted from ears were crossed with pollens collected from non-transgenic *Z. mays* (inbred line A188) to obtain T1 seeds. These seeds were used to conduct evaluation test for biomass-related characters. The evaluation test was conducted on 6 out of the 25 collected plants, in consideration of the results of PCR assay of the OsBIL7 gene and the hygromycin resistance gene in T0 generation plants, as well as plant shape, number of seeds, and seed weight. The evaluation test was conducted in two rounds (on a total of 6 lines consisting of 3 lines in first round and 3 lines in second round). Each one of the grains for each line was seeded into a polypot with a volume of 570 cc (a total of 25 grains per line were seeded in a total of 25 pots). After 17 to 18 days of seeding, portions of leaves were cut away, immersed in hygromycin solution, and examined for hygromycin resistance and sensitivity. Some plants inferior in early growth stage were eliminated, and 16 plants for each line were transplanted to polypots with a volume of 5100 cc and continued to be planted. The characters measured were days to silking, number of leaves, lengths of 9th to 13th leaves, and plant height. As for days to silking, the number of days from seeding to silking was counted, and as for plant height, the final plant height after 84 days of seeding was measured. For each line, comparison was made between hygromycin-resistant plants (i.e., plants regarded as harboring the OsBIL7 gene) and hygromycin-sensitive plants (i.e., plants regarded as deficient in the OsBIL7 gene). The results are shown in Table 12. As a result, no difference in days to silking and total number of leaves was observed between the resistant plants and the sensitive plants. However, the plant height and lengths of 9th to 13th leaves in the resistant plants increased relative to those in the sensitive plants (Table 12).

To sum up the above, it was found that overexpression of the OsBIL7 gene in the *Z. mays* inbred line "A188" results in an increase in *Z. mays* upper-ground biomass.

TABLE 12

| Line name | Hygromycin | Number of plants | days to silking (days) | Total number of leaves (leaves) | Leaf length (cm) | | | | | Plant height (cm) |
|---|---|---|---|---|---|---|---|---|---|---|
| | | | | | 9th leaf | 10th leaf | 11th leaf | 12th leaf | 13th leaf | |
| OsBIL7-01 | Resistant | 12 | 58.5 | 14.9 | 87.1 | 87.3 | 83.3 | 78.7 | 70.1 | 150.7 |
| | Sensitive | 4 | 59.3 | 14.5 | 85.3 | 83.5 | 78.3 | 73.8 | 64.0 | 146.8 |
| OsBIL7-02 | Resistant | 10 | 59.4 | 15.0 | 87.5 | 86.1 | 81.4 | 76.5 | 67.0 | 147.3 |
| | Sensitive | 4 | 59.5 | 15.0 | 86.3 | 85.0 | 79.8 | 75.5 | 67.0 | 146.5 |
| OsBIL7-03 | Resistant | 8 | 58.6 | 14.9 | 87.5 | 86.5 | 82.4 | 77.1 | 68.3 | 149.1 |
| | Sensitive | 8 | 60.0 | 14.5 | 85.5 | 82.8 | 78.0 | 71.3 | 60.4 | 140.8 |
| OsBIL7-04 | Resistant | 8 | 56.6 | 14.9 | 90.8 | 89.8 | 62.5 | 78.0 | 66.4 | 163.6 |
| | Sensitive | 8 | 58.8 | 14.8 | 86.0 | 84.1 | 78.5 | 72.8 | 63.4 | 161.9 |
| OsBIL7-05 | Resistant | 8 | 59.8 | 15.0 | 91.8 | 88.5 | 81.5 | 75.1 | 65.8 | 165.6 |
| | Sensitive | 8 | 59.3 | 15.0 | 86.3 | 83.4 | 77.9 | 72.4 | 63.3 | 162.5 |
| OsBIL7-06 | Resistant | 8 | 58.6 | 14.8 | 89.0 | 85.5 | 80.4 | 74.5 | 63.0 | 161.6 |
| | Sensitive | 8 | 57.6 | 14.8 | 82.5 | 78.8 | 74.3 | 68.3 | 58.4 | 157.5 |

INDUSTRIAL APPLICABILITY

The present invention is useful in industrial fields which can utilize biomass, such as food, energy and environment fields. By using this invention, plant biomass can be effectively increased.

The invention claimed is:

1. A genetically modified transgenic plant comprising a recombinant expression construct which overexpresses a recombinant nucleic acid encoding a protein in said genetically modified transgenic plant, wherein the protein comprises a region comprising the amino acid sequence of SEQ ID NO: 1, wherein said recombinant nucleic acid is operably linked to a heterologous promoter, wherein the protein is a hydroxyproline-rich glycoprotein and has at least 95% amino acid sequence identity to the amino acid sequence of SEQ ID NO: 13, and wherein the overexpression of the recombinant nucleic acid encoding the protein results in an increase in plant biomass in said genetically modified transgenic plant as compared to a control plant of the same species lacking said recombinant expression construct.

2. The genetically modified transgenic plant according to claim 1, wherein the amino acid sequence of SEQ ID NO: 1 is set forth in the amino acid sequence of SEQ ID NO: 2.

3. The genetically modified transgenic plant according to claim 1, wherein the recombinant nucleic acid is obtained from a monocotyledonous plant or a dicotyledonous plant, and wherein the genetically modified transgenic plant is a monocotyledonous plant.

4. A method for increasing plant biomass, comprising the step of transforming a plant with a recombinant expression construct which overexpresses a recombinant nucleic acid encoding a protein into said transformed plant, wherein the protein comprises a region comprising the amino acid sequence of SEQ ID NO: 1, wherein said recombinant nucleic acid is operably linked to a heterologous promoter, wherein the protein is a hydroxyproline-rich glycoprotein and has at least 95% amino acid sequence identity to the amino acid sequence of SEQ ID NO: 13, and wherein the overexpression of the recombinant nucleic acid encoding the protein results in an increase in plant biomass in said transformed plant as compared to a control plant of the same species lacking said recombinant expression construct.

5. The method according to claim 4 wherein the amino acid sequence of SEQ ID NO: 1 is set forth in the amino acid sequence of SEQ ID NO: 2.

6. The method according to claim 4, wherein the recombinant nucleic acid is obtained from a monocotyledonous plant or a dicotyledonous plant, and wherein the transformed plant is a monocotyledonous plant.

7. A recombinant expression construct comprising a recombinant nucleic acid encoding a protein and a heterologous promoter operably linked to the recombinant nucleic acid, wherein the protein comprises a region comprising the amino acid sequence of SEQ ID NO: 1, wherein the protein is a hydroxyproline-rich glycoprotein and has at least 95% amino acid sequence identity to the amino acid sequence of SEQ ID NO: 13, and wherein the overexpression of the recombinant nucleic acid encoding the protein results in an increase in plant biomass in a plant transformed with said recombinant expression construct as compared to a control plant of the same species lacking said recombinant expression construct.

8. The recombinant expression construct according to claim 7, wherein the amino acid sequence of SEQ ID NO: 1 is set forth in the amino acid sequence of SEQ ID NO: 2.

9. A recombinant expression vector comprising the recombinant construct of claim 7.

10. A transgenic host cell comprising the recombinant expression vector of claim 9.

11. A transgenic plant cell comprising the recombinant expression vector of claim 9.

12. The transgenic plant cell according to claim 11, wherein the recombinant nucleic acid is obtained from a monocotyledonous plant or a dicotyledonous plant, and wherein the transgenic plant cell is a monocotyledonous plant cell.

13. The genetically modified transgenic plant of claim 1, wherein said protein has the amino acid sequence of SEQ ID NO: 13.

* * * * *